US006762291B1

(12) United States Patent
Buchman et al.

(10) Patent No.: US 6,762,291 B1
(45) Date of Patent: Jul. 13, 2004

(54) INSECT P53 TUMOR SUPPRESSOR GENES AND PROTEINS

(75) Inventors: Andrew Roy Buchman, Berkeley, CA (US); Darren Mark Platt, San Francisco, CA (US); Michael Martin Ollman, Menlo Park, CA (US); Lynn Marie Young, Redwood City, CA (US); Madelyn Robin Demsky, San Francisco, CA (US); Kevin Patrick Keegan, San Lorenzo, CA (US); Lori Friedman, San Francisco, CA (US); Casey Kopczynski, Belmont, CA (US); Jeffrey S. Larson, Burlingame, CA (US); Stephanie A. Robertson, San Francisco, CA (US)

(73) Assignee: Exelixis, Inc., South San Francisco, CA (US)

( * ) Notice: Subject to any disclaimer, the term of this patent is extended or adjusted under 35 U.S.C. 154(b) by 0 days.

(21) Appl. No.: 09/524,101

(22) Filed: Mar. 13, 2000

Related U.S. Application Data

(63) Continuation-in-part of application No. 09/268,969, filed on Mar. 16, 1999.
(60) Provisional application No. 60/184,373, filed on Feb. 23, 2000.

(51) Int. Cl.[7] .......................... C12Q 1/68; C07H 21/04

(52) U.S. Cl. ............................ 536/23.1; 435/5; 435/6; 435/91.1; 435/91.2; 530/350; 530/351

(58) Field of Search ............................ 536/23.1; 435/5, 435/6, 91.1, 91 R; 530/350, 351

(56) References Cited

PUBLICATIONS

Harvey et al. Genbank Accesion No. AI516383. Drosophilia melanogaster. www.ncbi.nlm.nih.gov. 1997.*
www.ncbi.nlm.nih.gov, GenBank ID No. 16555, Jul. 26, 1993.
www.ncbi.nlm.nih.gov, GenBank ID No. 1244762, Apr. 29, 1996.
www.ncbi.nlm.nih.gov, GenBank ID No. 1244764, Apr. 29, 1996.
www.ncbi.nlm.nih.gov, GenBank ID No. 1310770, Jul. 28, 1995.
www.ncbi.nlm.nih.gov, GenBank ID No. 1310771, Jul. 28, 1995.
www.ncbi.nlm.nih.gov, GenBank ID No. 1310772, Jul. 29, 1995.
www.ncbi.nlm.nih.gov, GenBank ID No. 1310960, Jul. 11, 1995.
www.ncbi.nlm.nih.gov, GenBank ID No. 2370177, Sep. 1, 1997.
www.ncbi.nlm.nih.gov, GenBank ID No. 2781308, Sep. 30, 1996.
www.ncbi.nlm.nih.gov, GenBank ID No. 2828704, Aug. 10, 1998.
www.ncbi.mln.nih.gov, GenBank ID No. 2828706, Aug. 10, 1998.
www.ncbi.nlm.nih.gov, GenBank ID No. 3273745, Jul. 1, 1998.
www.ncbi.nlm.nih.gov, GenBank ID No. 3695080, Oct. 4, 1998.
www.ncbi.nlm.nih.gov, GenBank ID No. 3695096, Oct. 4, 1998.
www.ncbi.nlm.nih.gov, GenBank ID No. 3695098, Oct. 4, 1998.
www.ncbi.nlm.nih.gov, GenBank ID No. 3738114, Oct. 13, 1999.
www.ncbi.nlm.nih.gov, GenBank ID No. 4006838, Dec. 12, 1998.
www.ncbi.nlm.nih.gov, GenBank ID No. 4105775, Jan. 5, 1999.
www.ncbi.nlm.nih.gov, GenBank ID No. 4150930, Dec. 21, 1999.
www.ncbi.nlm.nih.gov, GenBank ID No. 4419333, Mar. 16, 1999.
www.ncbi.nlm.nih.gov, GenBank ID No. 4419483, Mar. 16, 1999.
www.ncbi.nlm.nih.gov, GenBank ID No. 4420516, Mar. 16, 1999.
www.ncbi.nlm.nih.gov, GenBank ID No. 4493931, Feb. 11, 2000.
www.ncbi.nlm.nih.gov, GenBank ID No. 4530684, Mar. 29, 1999.
www.ncbi.nlm.nih.gov, GenBank ID No. 5430686, Jul. 8, 1999.
www.ncbi.nlm.nih.gov, GenBank ID No. 5430689, Jul. 8, 1999.
www.ncbi.nlm.nih.gov, GenBank ID No. 4530690, Mar. 29, 1999.
www.ncbi.nlm.nih.gov, GenBank ID No. 4689085, Jul. 18, 2000.
www.ncbi.nlm.nih.gov, GenBank ID No. 4689086, Jul. 18, 2000.

(List continued on next page.)

*Primary Examiner*—Gary Benzion
*Assistant Examiner*—Jeanine Goldberg
(74) *Attorney, Agent, or Firm*—Laleh Shayesteh; Jan P. Brunelle

(57) ABSTRACT

A family of p53 tumor suppressor nucleic acid and protein isolated from several insect species is described. The p53 nucleic acid and protein can be used to genetically modify metazoan invertebrate organisms, such as insects and worms, or cultured cells, resulting in p53 expression or mis-expression. The genetically modified organisms or cells can be used in screening assays to identify candidate compounds that are potential pesticidal agents or therapeutics that interact with p53 protein. They can also be used in methods for studying p53 activity and identifying other genes that modulate the function of, or interact with, the p53 gene. Nucleic acid and protein sequences for Drosophila p33 and Rb tumor suppressors are also described.

2 Claims, 4 Drawing Sheets

OTHER PUBLICATIONS www.ncbi.nlm.nih.gov, GenBank ID No. 4803651, May 10, 1999.

www.ncbi.nlm.nih.gov, GenBank ID No. 5670498, Aug. 2, 1999.

www.ncbi.nlm.nih.gov, GenBank ID No. 5877734, Sep. 13, 1999.

www.ncbi.nlm.nih.gov, GenBank ID No. 6070492, Oct. 19, 1999.

www.ncbi.nlm.nih.gov, GenBank ID No. 6072079, Oct. 19, 1999.

www.ncbi.nlm.nih.gov, GenBank ID No. 6468070, Nov. 25, 1999.

www.ncbi.nlm.nih.gov, GenBank ID No. 6664917, Jan. 3, 2000.

* cited by examiner

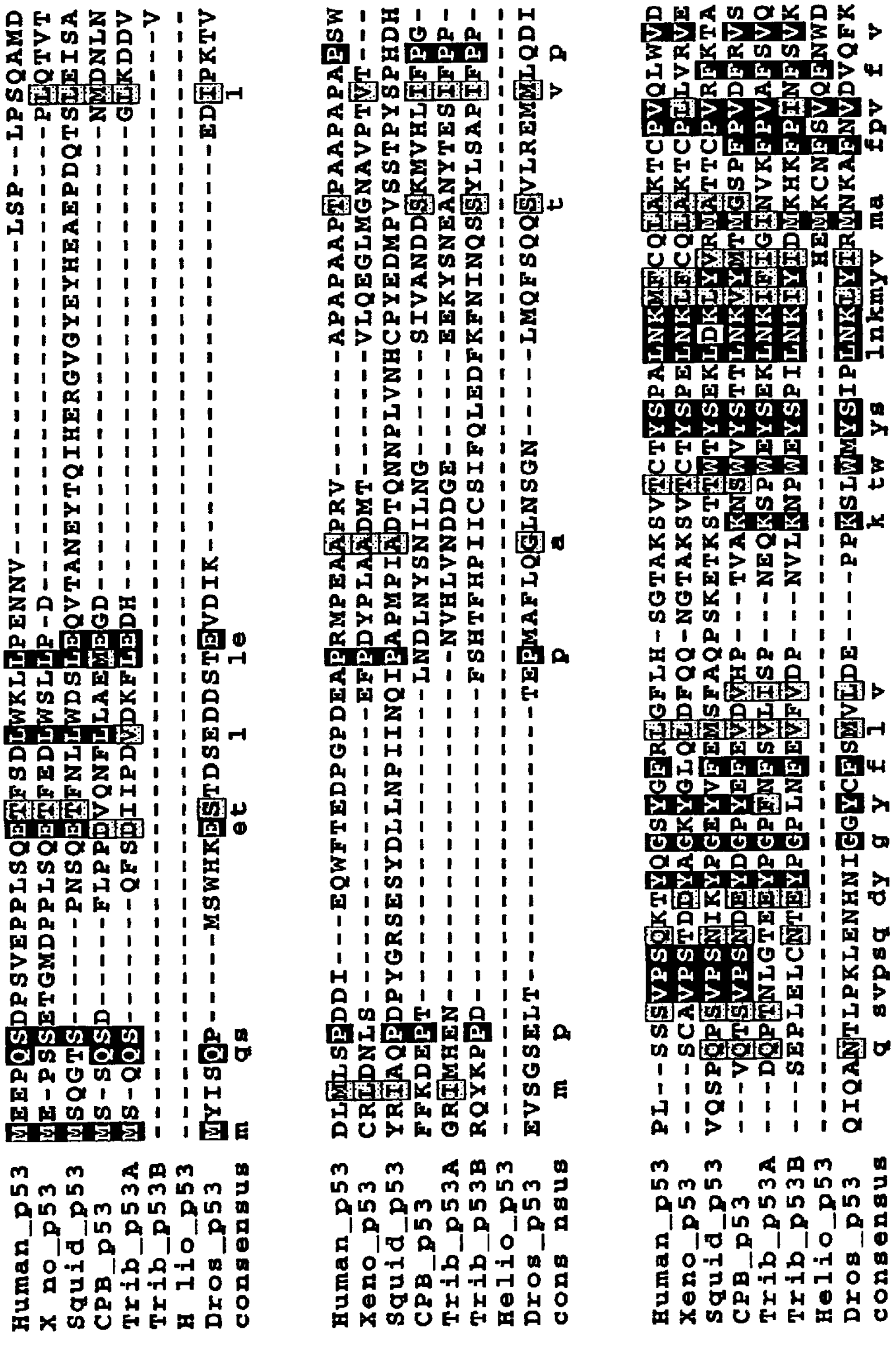
FIG._1A

```
Human_p53  STPP-PGTRVRAMAIYKQSQHMTEVVRRCPHHERCSD-----SDGLAPPQHLIRVEGNLR
Xeno_p53   SPPP-RGSILRATAVYKKSEHVAEVVKRCPHHERSVEP----GEDAAPPSHLMRVEGNLQ
Squid_p53  RPPP-SGCQIRAMPIYMKPEHVQEVVKRCPNHATAKEH----NEKHPAPLHIVRCEHKL-
CPB_p53    HRPP-NPLFIRSTPVYSAPQFAQECVYRCLNHEFSHKES-DGDLKEHIRPHIIRCANQYA
Trib_p53A  NRPQNLPLYIRATPVFSQTQHFQDLVHRCVGHRHPQDQS-NKGVAPHIFQHIIRCTNDNA
Trib_p53B  KADPERRLFVRVMPMFEEDRYVQELVHRCICHEQLTDPT-NHNVSEMVAQHIIRCDNNNA
Helio_p53  YQKA-PHMFVRSTVVFSDETQAEKRVERCVQHFHESSTSGIQTEIAKNVLHSSREIGTQG
Dros_p53   SKMPIQPLNLRVFLCFSND--VSAPVVRCQNHLSVEPLT---ANNAKMRESLLRSENPNS
cons nsus    pp   lfvRatpvys    hvqevV RClnHe   d s    d   i  hiiRcennna

Human_p53  VEYLDDRNT---FRHSVVVPYEP----PEVGSDCTTIHYNYMCNSSCMG-GMNRRPILTI
X no_p53   AYYMEDVNS---GRHSVCVPYEG----PQVGTECTTVLYNYMCNSSCMG-GMNRRPILTI
Squid_p53  AKYHEDKYS---GRQSVLTPHEM----PQAGSEWVVNLYQFMCLGSCVG-GPNRRPIQTV
CPB_p53    AYLGDKSKN---ERLSVVTPFGI----PQTGTESVREIFEFVCKNSCPSPGMNRRAVETI
Trib_p53A  LYFGDKNTG---TRLNTVLPLAH----PQVGEDVVKEFFQFVCKNSCPL-GMNRRPIDVV
Trib_p53B  QYFGDKNAG---KRLS--------------------------------------------
H lio_p53  VYYCGKVDM---ADSWYSVLVEF----MRTSSESCSHAYQFSCKNSCAT-GINRRAIATI
Dros_p53   VYCGNAQGKGISERFSVVVPLNMSRSVTRSGLTRQTLAFKFVCQNSCIG----RKETSLV
cons nsus  vyygdk      r svvvp e      pq gse   t  ynfmc nscmg gmnrrpi li
```

FIG._1B

```
Human_p53   ITLEDSSGNLLGRNSFEVRVCACPGRDRRTEEE-NLRKKG----EPHHELPPGSTKRALP
Xeno_p53    ITLETPQGLLLGRRCFEVRVCACPGRDRRTEED-NYTKK-------RGLKPSG--KRELA
Squid_p53   FTLEK-DNQVLGRRAVEVRICACPGRDRKADEKASLVSK------PPSPKKNGFPQRSLV
CPB_p53     FTLEDNQGTIYGRKTINVRICSCPKRDKEKDEKDNTANT---------NLPHG-KKRKME
Trib_p53A   FTLEDNKGEVFGRRLVGVRVCSCPKRDKDKEEK-DMESA----------VPPRRKKRKLG
Trib_p53B   ------------------------------------------------------------
Helio_p53   FTLEDAMGNIHGRQKVGAR-----------------------------------------
Dros_p53    FCLEKACGDIVGQHVIHVKICTCPKRDRIQDERQLNSKKRKSVPEAAEEDEPSKVRRCIA
cons nsus   ftled   g llgrr  v vrvc cp rdr   eek     k            p g  kr l

Human_p53   NNTSSSP-QPKK---KPLDGEYFTLQIRGRERFEMFRELNEALELKDAQAG---------
Xeno_p53    HPPSSEPPLPKKRLVVDDDEEIFTLRIKGRSRYEMIKKLNDALELQESLDQQ--------
Squid_p53   LTNDITKITPKK---RKIDDECFTLKVRGRENYEILCKLRDIMELAARTPEAERLLYKQE
CPB_p53     KPSKKPMQTQAE---NDTKEFTLTIPLVGRHNEQNVLKYCHDLMAGEILRN---------
Trib_p53A   NDERRVVPQGSS----DNKIFALNIHIPGKKNYLQALKMCQDMLANEILKKQ--------
Trib_p53B   ------------------------------------------------------------
Helio_p53   ------------------------------------------------------------
Dros_p53    IKTEDTESNDSRDCDDSAAEWNVSRTPDGDYRLATTCPNKEWLLQSIEGMIK--------
consensus              k       e    tl i gr    f m   kl e l   d l

Human_p53   -KEPGG---SRAHSSHLKSKKGQ-------------STSRHKKLMFKTEGPDSD-----
Xeno_p53    -KVTIK---CRKCRDEIKPKKG------------------KKLLVKDEQPDSE-----
Squid_p53   RQAPIGRLTSLPSSSSNGSQDGSRSSTAFSTSDSSQVNSSQNNTQMVNGQVPHEEETPVT
CPB_p53     ----IG----NGTEGPYKIALN--------------------KINTLIRESSE----
Trib_p53A   ---EQG----GD-DSADKNCYN------------------EITVLLNGTAAFD------
Trib_p53B   ------------------------------------------------------------
Helio_p53   ------------------------------------------------------------
Dros_p53    --EAAAEVLRNPNQENLRRHAN-------------------KLLSLKKRAYELP-----
consensus        g           k                        lmv     d
```

FIG._1C

```
Human_p53   ------------------------------------------------------------
X no_p53    ------------------------------------------------------------
Squid_p53   KCEPTENTIAQWLTKLGLQAYIDNFQQKGLHNMFQLDEFTLEDLQSMRIGTGHRNKIWKS
CPB_p53     ------------------------------------------------------------
Trib_p53A   ------------------------------------------------------------
Trib_p53B   ------------------------------------------------------------
H lio_p53   ------------------------------------------------------------
Dros_p53    ------------------------------------------------------------
cons nsus

Human_p53   ------------------------------------------------------
Xeno_p53    ------------------------------------------------------
Squid_p53   LLDYRRLLSSGTESQALQHAASNASTLSVGSQNSYCPGFYEVTRYTYKHTISYL
CPB_p53     ------------------------------------------------------
Trib_p53A   ------------------------------------------------------
Trib_p53B   ------------------------------------------------------
Helio_p53   ------------------------------------------------------
Dros_p53    ------------------------------------------------------
consensus
```

FIG._1D

SEQUENCE LISTING

<160> NUMBER OF SEQ ID NOS: 35

<210> SEQ ID NO 1
<211> LENGTH: 1573
<212> TYPE: DNA
<213> ORGANISM: Drosophila melanogaster

<400> SEQUENCE: 1
aaaatccaaa tagtcggtgg ccactacgat tctgtagttt tttgttagcg aatttttaat 60
atttagcctc cttccccaac aagatcgctt gatcagatat agccgactaa gatgtatata 120
tcacagccaa tgtcgtggca caaagaaagc actgattccg aggatgactc cacggaggtc 180
gatatcaagg aggatattcc gaaaacggtg gaggtatcgg gatcggaatt gaccacggaa 240
cccatggcct tcttgcaggg attaaactcc gggaatctga tgcagttcag ccagcaatcc 300
gtgctgcgcg aaatgatgct gcaggacatt cagatccagg cgaacacgct gcccaagcta 360
gagaatcaca acatcggtgg ttattgcttc agcatggttc tggatgagcc gcccaagtct 420
ctttggatgt actcgattcc gctgaacaag ctctacatcc ggatgaacaa ggccttcaac 480
gtggacgttc agttcaagtc taaaatgccc atccaaccac ttaatttgcg tgtgttcctt 540
tgcttctcca atgatgtgag tgctcccgtg gtccgctgtc aaaatcacct tagcgttgag 600
cctttgacgg ccaataacgc aaaaatgcgc gagagcttgc tgcgcagcga gaatcccaac 660
agtgtatatt gtggaaatgc tcagggcaag ggaatttccg agcgtttttc cgttgtagtc 720
cccctgaaca tgagccggtc tgtaacccgc agtgggctca cgcgccagac cctggccttc 780
aagttcgtct gccaaaactc gtgtatcggg cgaaaagaaa cttccttagt cttctgcctg 840
gagaaagcat gcggcgatat cgtgggacag catgttatac atgttaaaat atgtacgtgc 900
cccaagcggg atcgcatcca agacgaacgc cagctcaata gcaagaagcg caagtccgtg 960
ccggaagccg ccgaagaaga tgagccgtcc aaggtgcgtc ggtgcattgc tataaagacg 1020
gaggacacgg agagcaatga tagccgagac tgcgacgact ccgccgcaga gtggaacgtg 1080
tcgcggacac cggatggcga ttaccgtctg gctattacgt gccccaataa ggaatggctg 1140
ctgcagagca tcgagggcat gattaaggag gcggcggctg aagtcctgcg caatcccaac 1200
caagagaatc tacgtcgcca tgccaacaaa ttgctgagcc ttaagaaacg tgcctacgag 1260
ctgccatgac ttctgatctg gtcgacaatc tcccaggtat cagatacctt tgaaatgtgt 1320
tgcatctgtg ggtatacta catagctatt agtatcttaa gtttgtatta gtccttgttc 1380
gtaaggcgtt taacggtgat attccccttt tggcatgttc gatggccgaa aagaaaacat 1440
ttttatattt ttgatagtat actgttgtta actgcagttc tatgtgacta cgtaactttt 1500
gtctaccaca acaaacatac tctgtacaaa aaagccaaaa gtgaatttat taaagagttg 1560
tcatattttg caa 1573

<210> SEQ ID NO 2
<211> LENGTH: 385
<212> TYPE: PRT
<213> ORGANISM: Drosophila melanogaster

<400> SEQUENCE: 2

Met Tyr Ile Ser Gln Pro Met Ser Trp His Lys Glu Ser Thr Asp Ser
1 5 10 15

Glu Asp Asp Ser Thr Glu Val Asp Ile Lys Glu Asp Ile Pro Lys Thr
20 25 30

-continued

```
Val Glu Val Ser Gly Ser Glu Leu Thr Thr Glu Pro Met Ala Phe Leu
        35                  40                  45

Gln Gly Leu Asn Ser Gly Asn Leu Met Gln Phe Ser Gln Gln Ser Val
    50                  55                  60

Leu Arg Glu Met Met Leu Gln Asp Ile Gln Ile Gln Ala Asn Thr Leu
65                  70                  75                  80

Pro Lys Leu Glu Asn His Asn Ile Gly Gly Tyr Cys Phe Ser Met Val
                85                  90                  95

Leu Asp Glu Pro Pro Lys Ser Leu Trp Met Tyr Ser Ile Pro Leu Asn
            100                 105                 110

Lys Leu Tyr Ile Arg Met Asn Lys Ala Phe Asn Val Asp Val Gln Phe
        115                 120                 125

Lys Ser Lys Met Pro Ile Gln Pro Leu Asn Leu Arg Val Phe Leu Cys
    130                 135                 140

Phe Ser Asn Asp Val Ser Ala Pro Val Val Arg Cys Gln Asn His Leu
145                 150                 155                 160

Ser Val Glu Pro Leu Thr Ala Asn Asn Ala Lys Met Arg Glu Ser Leu
                165                 170                 175

Leu Arg Ser Glu Asn Pro Asn Ser Val Tyr Cys Gly Asn Ala Gln Gly
            180                 185                 190

Lys Gly Ile Ser Glu Arg Phe Ser Val Val Val Pro Leu Asn Met Ser
        195                 200                 205

Arg Ser Val Thr Arg Ser Gly Leu Thr Arg Gln Thr Leu Ala Phe Lys
    210                 215                 220

Phe Val Cys Gln Asn Ser Cys Ile Gly Arg Lys Glu Thr Ser Leu Val
225                 230                 235                 240

Phe Cys Leu Glu Lys Ala Cys Gly Asp Ile Val Gly Gln His Val Ile
                245                 250                 255

His Val Lys Ile Cys Thr Cys Pro Lys Arg Asp Arg Ile Gln Asp Glu
            260                 265                 270

Arg Gln Leu Asn Ser Lys Lys Arg Lys Ser Val Pro Glu Ala Ala Glu
        275                 280                 285

Glu Asp Glu Pro Ser Lys Val Arg Arg Cys Ile Ala Ile Lys Thr Glu
    290                 295                 300

Asp Thr Glu Ser Asn Asp Ser Arg Asp Cys Asp Asp Ser Ala Ala Glu
305                 310                 315                 320

Trp Asn Val Ser Arg Thr Pro Asp Gly Asp Tyr Arg Leu Ala Ile Thr
                325                 330                 335

Cys Pro Asn Lys Glu Trp Leu Leu Gln Ser Ile Glu Gly Met Ile Lys
            340                 345                 350

Glu Ala Ala Ala Glu Val Leu Arg Asn Pro Asn Gln Glu Asn Leu Arg
        355                 360                 365

Arg His Ala Asn Lys Leu Leu Ser Leu Lys Lys Arg Ala Tyr Glu Leu
    370                 375                 380

Pro
385


<210> SEQ ID NO 3
<211> LENGTH: 2600
<212> TYPE: DNA
<213> ORGANISM: Leptinotarsa decemlineata

<400> SEQUENCE: 3

gtgtttagtt attgttcggg ggctgttttt ttaattaaaa atttcacggg taaatctttg     60
```

-continued

```
ttgtcttttc tttttctaat tgtatcagaa tagctttttt aactgtgaaa accggaaggg    120
atgtcttctc agtcagactt tttacctcca gatgttcaaa atttcctctt ggcagaaatg    180
gaaggggaca atatggataa tctaaacttt ttcaaggacg aaccaacttt gaatgattta    240
aattattcaa acatcctaaa tggatcaata gttgctaatg atgattcaaa gatggttcat    300
cttatttttc cgggagtaca aacaagtgtc ccatcaaatg atgaatacga tggtccatat    360
gaatttgaag tagatgttca tcccactgtg gcaaaaaatt cgtgggtgta ctctaccacc    420
ctgaataaag tttatatgac aatgggcagt ccatttcctg tagatttcag agtatcacat    480
cgacccccga acccattatt catcaggagc actcccgttt acagtgctcc ccaatttgct    540
caagaatgtg tttaccggtg cctaaaccat gaattctctc ataaagagtc tgatggagat    600
ctcaaggaac acattcgccc tcatatcata agatgtgcca atcagtatgc tgcttactta    660
ggtgacaagt ctaaaaatga acgtctcagc gttgtcatac cattcggtat cccgcagacg    720
ggtactgaaa gtgttagaga aattttcgaa tttgtttgca aaaattcttg cccaagtcct    780
ggaatgaata gaagagctgt ggaaataata ttcactttgg aggataatca aggaactatc    840
tatggacgca aaacattaaa tgtgagaata tgctcttgtc caaaacgtga taaagagaaa    900
gatgaaaagg ataacactgc caacactaat ctgccgcatg gcaaaaagag aaaaatggag    960
aagccatcaa agaaacccat gcagacacag gcagaaaatg ataccaaaga gtttactctg   1020
accataccgc tggtgggtcg acataatgaa caaaatgtgt tgaagtattg ccatgatttg   1080
atggccgggg aaatcctgcg aaatatcggc aatggtactg aagggccgta caaaatagct   1140
ttaaacaaaa taaacacgtt gatacgtgaa agttccgagt gaccttatca attctatgta   1200
tatttcttat acaattccat tttcatattt ccatttgata ataagaaaca ttttagcacc   1260
ttttaatcct acactgcagg gaagtcaata tttctttagt tttttgcatg atattgtttg   1320
ttataacatt ttttttttca acaacaggtg acttgatttt tgtaaggtat ctcattattt   1380
atgtttaaga cctaaaacac gaaaccaaaa acatgaatgg tcattgaatt tggctcgata   1440
atcaatccaa tgttctttaa agtaatatcg acctgttcac aacttttgtg atgcactgaa   1500
tggcttttta ttattattat ttttcagcat tgtacatcat acttgcatag tttcagtttt   1560
aaatttttca aatgtttcat ttattttcat tcttacacct gaacttggat tttggacaca   1620
tggctttcac aatgttctat cacgaacagt atgataagcc aaagtaagag ttgataatag   1680
ttcatattaa tatctattgt aacaccgact attgttatat aaatagtcgt ttttttgtta   1740
cttttcttgc tttattttat acacttgagt caagtgtagt cagtacattg actatgctgg   1800
aaaacctgtt ttgagtttat ttttacttac attcagttct catcattaga aattgtttat   1860
tttttgtgtg caatatttac gaaaaatggt gcaatactat aataggaaca ttaataaagt   1920
aacttgaaag catagaggtg gtgaattttg tttttgatca actttttgaa atttatgcgc   1980
cattctataa gccagttttt tttgataaat tcaaaattca cgaataggta tcaacctgat   2040
tgcatgctta ttctatgttt gtcctaaagc aggtctctat aaaacttctc taaaagttgt   2100
gcagagcaaa taacaaataa ttttttaatg gattatatca attcatgaac tggtttaatt   2160
gaaagagtag attattctat tgggttcaca aaaatataaa taatgtgtta ctatctggat   2220
catttgtttt tttttcattg agctatattt tgtcattgta ttgttgaact ttccctaaat   2280
cccagtgcca tagtcgacga tcggtctcgc tcccatccat caattattcg aaatctcatt   2340
tattttaaag actgaggacg gggtgggact gtcagtgtat ctgtttaatg agaaccatct   2400
```

-continued

```
tgtactagga ttgatatgtg aatctatgag taggtgcatt tttatatata tatctttatg   2460

tttatttagt attattgtac aggttatgta ctctagtgga agaatacata acctaattat   2520

tatatatgtt cgttaatata caaatttttt acgtttttaa aatatatttt ctaaatattc   2580

aacaaaaaaa aaaaaaaaaa                                               2600


<210> SEQ ID NO 4
<211> LENGTH: 354
<212> TYPE: PRT
<213> ORGANISM: Leptinotarsa decemlineata

<400> SEQUENCE: 4

Met Ser Ser Gln Ser Asp Phe Leu Pro Pro Asp Val Gln Asn Phe Leu
1               5                   10                  15

Leu Ala Glu Met Glu Gly Asp Asn Met Asp Asn Leu Asn Phe Phe Lys
            20                  25                  30

Asp Glu Pro Thr Leu Asn Asp Leu Asn Tyr Ser Asn Ile Leu Asn Gly
        35                  40                  45

Ser Ile Val Ala Asn Asp Asp Ser Lys Met Val His Leu Ile Phe Pro
    50                  55                  60

Gly Val Gln Thr Ser Val Pro Ser Asn Asp Glu Tyr Asp Gly Pro Tyr
65                  70                  75                  80

Glu Phe Glu Val Asp Val His Pro Thr Val Ala Lys Asn Ser Trp Val
                85                  90                  95

Tyr Ser Thr Thr Leu Asn Lys Val Tyr Met Thr Met Gly Ser Pro Phe
            100                 105                 110

Pro Val Asp Phe Arg Val Ser His Arg Pro Pro Asn Pro Leu Phe Ile
        115                 120                 125

Arg Ser Thr Pro Val Tyr Ser Ala Pro Gln Phe Ala Gln Glu Cys Val
    130                 135                 140

Tyr Arg Cys Leu Asn His Glu Phe Ser His Lys Glu Ser Asp Gly Asp
145                 150                 155                 160

Leu Lys Glu His Ile Arg Pro His Ile Ile Arg Cys Ala Asn Gln Tyr
                165                 170                 175

Ala Ala Tyr Leu Gly Asp Lys Ser Lys Asn Glu Arg Leu Ser Val Val
            180                 185                 190

Ile Pro Phe Gly Ile Pro Gln Thr Gly Thr Glu Ser Val Arg Glu Ile
        195                 200                 205

Phe Glu Phe Val Cys Lys Asn Ser Cys Pro Ser Pro Gly Met Asn Arg
    210                 215                 220

Arg Ala Val Glu Ile Ile Phe Thr Leu Glu Asp Asn Gln Gly Thr Ile
225                 230                 235                 240

Tyr Gly Arg Lys Thr Leu Asn Val Arg Ile Cys Ser Cys Pro Lys Arg
                245                 250                 255

Asp Lys Glu Lys Asp Glu Lys Asp Asn Thr Ala Asn Thr Asn Leu Pro
            260                 265                 270

His Gly Lys Lys Arg Lys Met Glu Lys Pro Ser Lys Lys Pro Met Gln
        275                 280                 285

Thr Gln Ala Glu Asn Asp Thr Lys Glu Phe Thr Leu Thr Ile Pro Leu
    290                 295                 300

Val Gly Arg His Asn Glu Gln Asn Val Leu Lys Tyr Cys His Asp Leu
305                 310                 315                 320

Met Ala Gly Glu Ile Leu Arg Asn Ile Gly Asn Gly Thr Glu Gly Pro
                325                 330                 335
```

```
Tyr Lys Ile Ala Leu Asn Lys Ile Asn Thr Leu Ile Arg Glu Ser Ser
            340                 345                 350

Glu Trp


<210> SEQ ID NO 5
<211> LENGTH: 1291
<212> TYPE: DNA
<213> ORGANISM: Tribolium castaneum

<400> SEQUENCE: 5

acgcgtccgg ccaacttaac ctaaaaattt gttttcgatg cctactagat ttaaaaacaa      60

ttgattcaaa tcgtggattt ttattattta aatcatgagc caacaaagtc aattttcgga     120

catcattcct gatgttgata aatttttgga agatcatgga ctcaaggacg atgtgggaag     180

aataatgcac gaaaacaacg tccatttagt aaatgacgac ggagaagaag aaaaatactc     240

taatgaagcc aattacactg aatcaatttt cccccccgac cagcccacaa acctaggcac     300

tgaggaatac ccaggccctt ttaatttctc agtcctgatc agccccaacg agcaaaaatc     360

gccctgggag tattcggaaa aactgaacaa aatattcatc ggcatcaacg tgaaattccc     420

cgtggccttc tccgtgcaaa accgccccca gaacctgccc ctctacatcc gcgccacccc     480

cgtgttcagc caaacgcagc acttccaaga cctggtgcac cgctgcgtcg gccaccgcca     540

cccccaagac cagtccaaca aaggcgtcgc cccccacatt ttccagcaca ttattaggtg     600

caccaacgac aacgccctat actttggcga taaaaacaca gggacgagac tcaacatcgt     660

cctgcctttg gcccaccccc aggtggggga ggacgtggtc aaggagtttt tccagtttgt     720

gtgcaaaaac tcctgccctt tggggatgaa tcggcggccg attgatgtcg ttttcaccct     780

ggaggataat aagggggagg ttttcgggag gaggttggtg ggggtgaggg tgtgttcgtg     840

tccgaagcgt gacaaggaca aggaggagaa ggacatggag agtgctgtgc ctccaaggag     900

gaagaagagg aagttgggga atgatgagcg aagggttgtg ccacagggga gctccgataa     960

taaaatattt gcgttaaata ttcatattcc tggcaagaag aattatttac aagccctcaa    1020

gatgtgtcaa gatatgctgg ctaatgaaat tttgaaaaaa caggaacaag gtggcgacga    1080

ttctgctgat aagaactgtt ataatgagat aactgttctc ttgaacggca cggccgcctt    1140

tgattagttt atttctatat ttaattttat actttgtact tatgcaatat tccagtttac    1200

ttttgtaata tttttattaa taaatttcta cgttttaaaa aaaaaaaaaa aaaaaaaaaa    1260

aaaaaaaaaa aaaaaaaaaa aaaaaaaaaa a                                   1291


<210> SEQ ID NO 6
<211> LENGTH: 350
<212> TYPE: PRT
<213> ORGANISM: Tribolium castaneum

<400> SEQUENCE: 6

Met Ser Gln Gln Ser Gln Phe Ser Asp Ile Ile Pro Asp Val Asp Lys
1               5                   10                  15

Phe Leu Glu Asp His Gly Leu Lys Asp Asp Val Gly Arg Ile Met His
            20                  25                  30

Glu Asn Asn Val His Leu Val Asn Asp Asp Gly Glu Glu Glu Lys Tyr
        35                  40                  45

Ser Asn Glu Ala Asn Tyr Thr Glu Ser Ile Phe Pro Pro Asp Gln Pro
    50                  55                  60

Thr Asn Leu Gly Thr Glu Glu Tyr Pro Gly Pro Phe Asn Phe Ser Val
65                  70                  75                  80
```

```
Leu Ile Ser Pro Asn Glu Gln Lys Ser Pro Trp Glu Tyr Ser Glu Lys
                85                  90                  95

Leu Asn Lys Ile Phe Ile Gly Ile Asn Val Lys Phe Pro Val Ala Phe
            100                 105                 110

Ser Val Gln Asn Arg Pro Gln Asn Leu Pro Leu Tyr Ile Arg Ala Thr
        115                 120                 125

Pro Val Phe Ser Gln Thr Gln His Phe Gln Asp Leu Val His Arg Cys
    130                 135                 140

Val Gly His Arg His Pro Gln Asp Gln Ser Asn Lys Gly Val Ala Pro
145                 150                 155                 160

His Ile Phe Gln His Ile Ile Arg Cys Thr Asn Asp Asn Ala Leu Tyr
                165                 170                 175

Phe Gly Asp Lys Asn Thr Gly Thr Arg Leu Asn Ile Val Leu Pro Leu
            180                 185                 190

Ala His Pro Gln Val Gly Glu Asp Val Val Lys Glu Phe Phe Gln Phe
        195                 200                 205

Val Cys Lys Asn Ser Cys Pro Leu Gly Met Asn Arg Arg Pro Ile Asp
    210                 215                 220

Val Val Phe Thr Leu Glu Asp Asn Lys Gly Glu Val Phe Gly Arg Arg
225                 230                 235                 240

Leu Val Gly Val Arg Val Cys Ser Cys Pro Lys Arg Asp Lys Asp Lys
                245                 250                 255

Glu Glu Lys Asp Met Glu Ser Ala Val Pro Pro Arg Arg Lys Lys Arg
            260                 265                 270

Lys Leu Gly Asn Asp Glu Arg Arg Val Val Pro Gln Gly Ser Ser Asp
        275                 280                 285

Asn Lys Ile Phe Ala Leu Asn Ile His Ile Pro Gly Lys Lys Asn Tyr
    290                 295                 300

Leu Gln Ala Leu Lys Met Cys Gln Asp Met Leu Ala Asn Glu Ile Leu
305                 310                 315                 320

Lys Lys Gln Glu Gln Gly Gly Asp Asp Ser Ala Asp Lys Asn Cys Tyr
                325                 330                 335

Asn Glu Ile Thr Val Leu Leu Asn Gly Thr Ala Ala Phe Asp
            340                 345                 350


<210> SEQ ID NO 7
<211> LENGTH: 508
<212> TYPE: DNA
<213> ORGANISM: Tribolium castaneum

<400> SEQUENCE: 7

gtacgacaat acaaaccgcc cgatttttcc cacactttcc acccaataat ttgctcaatt      60

ttccagttgg aagacttcaa attcaacatc aaccaaagct cgtacctctc agcccccatt     120

ttcccccccca gcgagccgct cgagctgtgc aacaccgagt accccggccc cctcaacttc    180

gaggtgtttg tggaccccaa cgtgctcaaa aacccctggg aatactcccc aattctcaac     240

aaaatttaca tcgatatgaa acacaaattc ccgattaatt tcagcgtgaa gaaggccgat     300

cctgagcgca ggctttttgt cagagttatg ccgatgtttg aggaagacag atatgtgcaa     360

gaattggtgc ataggtgcat ctgtcacgaa caattgacag atccgaccaa tcacaacgtt     420

tcggaaatgg tggctcagca catcattcgg tgtgataaca acaatgctca gtatttcggg     480

gataagaacg ctgggaagag actgagta                                        508
```

-continued

<210> SEQ ID NO 8
<211> LENGTH: 169
<212> TYPE: PRT
<213> ORGANISM: Tribolium castaneum

<400> SEQUENCE: 8

```
Val Arg Gln Tyr Lys Pro Pro Asp Phe Ser His Thr Phe His Pro Ile
1               5                   10                  15

Ile Cys Ser Ile Phe Gln Leu Glu Asp Phe Lys Phe Asn Ile Asn Gln
            20                  25                  30

Ser Ser Tyr Leu Ser Ala Pro Ile Phe Pro Pro Ser Glu Pro Leu Glu
        35                  40                  45

Leu Cys Asn Thr Glu Tyr Pro Gly Pro Leu Asn Phe Glu Val Phe Val
    50                  55                  60

Asp Pro Asn Val Leu Lys Asn Pro Trp Glu Tyr Ser Pro Ile Leu Asn
65                  70                  75                  80

Lys Ile Tyr Ile Asp Met Lys His Lys Phe Pro Ile Asn Phe Ser Val
                85                  90                  95

Lys Lys Ala Asp Pro Glu Arg Arg Leu Phe Val Arg Val Met Pro Met
            100                 105                 110

Phe Glu Glu Asp Arg Tyr Val Gln Glu Leu Val His Arg Cys Ile Cys
        115                 120                 125

His Glu Gln Leu Thr Asp Pro Thr Asn His Asn Val Ser Glu Met Val
    130                 135                 140

Ala Gln His Ile Ile Arg Cys Asp Asn Asn Asn Ala Gln Tyr Phe Gly
145                 150                 155                 160

Asp Lys Asn Ala Gly Lys Arg Leu Ser
                165
```

<210> SEQ ID NO 9
<211> LENGTH: 433
<212> TYPE: DNA
<213> ORGANISM: Heliothis virescens

<400> SEQUENCE: 9

```
gcacgagatg aagtgcaact ttagcgtgca attcaactgg gactatcaga aggcgccgca     60

tatgttcgtg cggtctaccg tcgtgttctc cgatgaaacg caggcggaga agcgggtcga    120

acgatgtgtg cagcatttcc atgaaagctc cacttctgga atccaaacag aaattgccaa    180

aaacgtgctc cactcgtccc gggagatcgg tacccagggc gtgtactact gcgggaaggt    240

ggacatggca gactcgtggt actcagtgct ggtggagttt atgaggacca gctcggagtc    300

ctgctcccat gcgtaccagt tctcctgcaa gaactcttgt gcaaccggca ttaataggcg    360

ggctattgcc attattttta cgctggaaga tgctatgggc aacatccacg gccgtcagaa    420

agtaggggcg agg                                                       433
```

<210> SEQ ID NO 10
<211> LENGTH: 144
<212> TYPE: PRT
<213> ORGANISM: Heliothis virescens

<400> SEQUENCE: 10

```
His Glu Met Lys Cys Asn Phe Ser Val Gln Phe Asn Trp Asp Tyr Gln
1               5                   10                  15

Lys Ala Pro His Met Phe Val Arg Ser Thr Val Val Phe Ser Asp Glu
            20                  25                  30

Thr Gln Ala Glu Lys Arg Val Glu Arg Cys Val Gln His Phe His Glu
```

-continued

```
        35                  40                  45

Ser Ser Thr Ser Gly Ile Gln Thr Glu Ile Ala Lys Asn Val Leu His
    50                  55                  60

Ser Ser Arg Glu Ile Gly Thr Gln Gly Val Tyr Tyr Cys Gly Lys Val
65                  70                  75                  80

Asp Met Ala Asp Ser Trp Tyr Ser Val Leu Val Glu Phe Met Arg Thr
                85                  90                  95

Ser Ser Glu Ser Cys Ser His Ala Tyr Gln Phe Ser Cys Lys Asn Ser
            100                 105                 110

Cys Ala Thr Gly Ile Asn Arg Arg Ala Ile Ala Ile Ile Phe Thr Leu
        115                 120                 125

Glu Asp Ala Met Gly Asn Ile His Gly Arg Gln Lys Val Gly Ala Arg
    130                 135                 140


<210> SEQ ID NO 11
<211> LENGTH: 26
<212> TYPE: DNA
<213> ORGANISM: Drosophila melanogaster

<400> SEQUENCE: 11

ccatgctgaa gcaataacca ccgatg                                          26


<210> SEQ ID NO 12
<211> LENGTH: 30
<212> TYPE: DNA
<213> ORGANISM: Drosophila melanogaster

<400> SEQUENCE: 12

ggaacacacg caaattaagt ggttggatgg                                      30


<210> SEQ ID NO 13
<211> LENGTH: 23
<212> TYPE: DNA
<213> ORGANISM: Drosophila melanogaster

<400> SEQUENCE: 13

tgattttgac agcggaccac ggg                                             23


<210> SEQ ID NO 14
<211> LENGTH: 28
<212> TYPE: DNA
<213> ORGANISM: Drosophila melanogaster

<400> SEQUENCE: 14

ggaagtttct tttcgcccga tacacgag                                        28


<210> SEQ ID NO 15
<211> LENGTH: 27
<212> TYPE: DNA
<213> ORGANISM: Drosophila melanogaster

<400> SEQUENCE: 15

ggcacaaaga aagcactgat tccgagg                                         27


<210> SEQ ID NO 16
<211> LENGTH: 28
<212> TYPE: DNA
<213> ORGANISM: Drosophila melanogaster

<400> SEQUENCE: 16

ggaatctgat gcagttcagc cagcaatc                                        28
```

<210> SEQ ID NO 17
<211> LENGTH: 23
<212> TYPE: DNA
<213> ORGANISM: Drosophila melanogaster

<400> SEQUENCE: 17
ggatcgcatc caagacgaac gcc 23

<210> SEQ ID NO 18
<211> LENGTH: 27425
<212> TYPE: DNA
<213> ORGANISM: Drosophila melanogaster

<400> SEQUENCE: 18
tagccactcg ctagtttata gttcaaggtg aacatacgta agagttttgt ggcactggac 60
tggaaatagg ctgctagtcc tttgtgttcg gccatagcgt taaaaattta agccaacgcc 120
agtcgtcctg cgcccatgtt gctgcaacat tctggcttcg tgtcatgcca ctgaatgttt 180
cacattattt aaccccctttt atttttttt tttgtgtggc actggccaaa ggtccaaagg 240
ggcgacatgc tgcaggggcg tggcctgcag ctgcttgcaa cgggcaatta ttgcgcagtt 300
attgcatgtc gtgtgcaatg cctatgaatt attacgtata cacagtgtgt cctcggcaat 360
aacgaaagtc cgggaggggg cggggcggta ttcatgctgc agttgcccat aaattcaacg 420
aaattgctac agtttttatt tgtaatgact gggcatggta agttaatatg attcttcata 480
ctgattaagt gcttttgtta cttttttaat tattcaagta aaaatattaa tttgtgtttc 540
atgggacttt ttgtagtagt taccctacta ctacattaaa cattaatttc aaagaagtag 600
atatacgagt aaatgggcaa tatgaaaatt tgaaaaaggt aaagcttatg atactaacta 660
atgccaaatg aaaactagga gtatgataat aatatgaaga tagcccacca ggctatccca 720
aaatcgtcat caaatccaat ggtgttcatt aaattaggta atcgcatgtg cccttatgtc 780
aaccatatcg ccgctcaacc aagtcatttc ggtcgctgag gcaatcgaga tatggggcgc 840
caccgacctt ggccaacatg ctccacattg ggctccaagt ggcaaccgca aaggtcacgc 900
acagttcgcc attgcgaatc gcatactgcc aatggaaact acattgcgta tctggtggcc 960
ctttgatggc gctctaatta aaggctacct gccactaatt agtgatagac aatcgtcggg 1020
ggagttcggg tggcatcgtt ggcaggcact taacccaaga caggggggcc aactggcatt 1080
ggatggccgt tttgaattc gtatgtcgga agcagtcgat gcagggttgg gggggatgga 1140
aacaaatgtt gtcaacgcca aaaccactga actgttaaaa gtgccattga atccaacaag 1200
gatgctgggc gcaactgtgc aacctaacaa actgtcggaa agacagcagc aacatgggca 1260
tgcatggctt gatactggga gtctgttcga tggatcccac ttgaaccgaa ccgtactgaa 1320
ccgtgccccg gccagatgag gcgcccccacc caacgccact cttgaaaacc ccaagccctt 1380
tgcacgcgct aaatagtttt gtttattgca cattgaaacc gagccagcga gcaattccgg 1440
tggctgctcc gcgcgcgaca cactccagcg atctaatcag caatctcgac gacgaccggg 1500
ctgacatggg gtttctcata cgctcggtta gacgcgacgt cgacgctcga tcgaatattt 1560
tcccaatgca ctggcagaaa atgtgtggaa gtgtgagatt aagctcataa attagtagtg 1620
cacttaatgt ggaaaatatt agaaacaaca gtgaacagtt gattggttct cttataaatt 1680
ttattaatta ttgaacattt gaagaaagat attgattaaa tcaactttgg atgtatacat 1740
atatataaaa aagtatatga tgactttcat gttgagaggt cataactttg taatgatatt 1800

-continued

```
ggttctagtc atcatttcgt gaaacagctg tgcaagcatt cgattatatg tggtatgtaa   1860
tttatttggg ttaatatatt tttcgcagtg tactgcttct gctgcgtcac ttcacattcg   1920
tatcatttac atacgcagca ctgcggagtg agtcgctgag tacctggcgc tctggggtct   1980
ctgggatctc tgggcttggg gatggatctc cactcgatga tctctccgcc tgggagccca   2040
gatcatcgtc tgctatttgc aagtcgagag tcgcgcgagt cggacgtaca atcgccgcag   2100
cggaatcaag tgtgataaaa gtgaacagaa ctttagccaa gtgcatttgg ctaatggaag   2160
tggtggcaaa agtcaaagcc acacgttata ctcgaattta aaaacaaata aataatgcat   2220
aagcaggcga gtttgaagta attagcacaa cgatgatgct ggcggccaac tgacccacat   2280
cgggaaatcg ctctaattca tatttgttgt cgagtgggcc aggataacag gataacagga   2340
tactgctggc tcatttgcat ttgcatatat gcaaatagtt cgatctgcag gcgattgagt   2400
gaccgaaagt gttggactgt gccaaataca taaccagcta acgggcaaaa agccactgaa   2460
taaatggccc ttgttactcg gttcgtgtaa tgcgtctacg agtttagccc gtgttctgac   2520
cgagaatcaa ttaaaattta ttgcacgagc atgccaaaca attcgcggtt gcagccacaa   2580
aaacgcatct gaaaaacaat gccaccactc caatcacttg tgaccgcccc ccggctatgc   2640
aaattagcca ttgcagcgat tttgctaatt ctccagctaa acgctagtgg tgagttctca   2700
gttggctaat atatatatat gtatatatat gaaatatgaa aaatcggaaa accccttttgc  2760
aaacattgct ccgcgcttag ctcatgatga tgccaattcc gagagcgttt tgaagatgca   2820
ctcgccattt gcattcaaaa gccaagcgaa taaatggaga agcaaaacca aaactgcata   2880
gatcaattta caagtcggca aaggggttta ctcgctgcat gtgcatgtca gctgctatta   2940
tagatttatt tattggcaaa caccctgaga acgagtttca ttgggggggcc taagtgggag  3000
aatgacctac acaggaaagt gctcttaact aagcaactaa cttctggaaa agcggaagtg   3060
gagagattaa gtactatctt atagatatgc cagaatatca aaaaagtatc taccagatac   3120
cttgaaagat ctctgcatat ctcaattgca attcatgata agtttgttaa gttacgtttt   3180
ttaatttcca attcaacctt tcaattagtt aataacgcca atctcagaca ttcctaaacc   3240
ccctccctac ttaagggtaa atcccgatga tgcttgattg attttctcat tgctcagcta   3300
tgcataaaaa tatcatatta attgatgagc acgagcttag ctaccagaat tgaaatccat   3360
atgactgctc ggcaatttga aaaatgcgtt ggttcccagt catgcgcatc ccgttggatt   3420
gaaacccaca ttcatggcat tccgttctgc cccccagttg cgctgctgct caagtgtccg   3480
ttgcaccagt tgcagctgca gaagatcgtc ggattccggc caccgctgga gtatctgaat   3540
gcggataatc ggatctacgg accggaaatg gtgagcaact tcaagactcg caacggccaa   3600
caggaacttc cggtcagcca ggtgtgctgg cgcatctgca acgaggatcc cgattgcatt   3660
gcctatgtcc atctgctgga cacggacgag tgccatggct actcgtactt cgagcgaacc   3720
tcgcgctatc tggccatttc gggtgaactg cctctggtgg cagacggcga ggccgtcttc   3780
tacgaaaaga cctgcctccg aggtgagtaa ttctccagcc aaacctccgg aagtggccgt   3840
gatccgcctc taatccattc cgaccttgca gttcccgatg cgtgccgtgg gcgtctctgg   3900
gcactgacca aaatccccgg cagcacgctg gtctaccaca gcaagaagac catttcgacg   3960
ctggtcacgc ggcgtgagtg cgccgagcgc tgcttcttcg aaacccagtt ccgatgcctc   4020
tccgcctcct ttgcgccctc ctatcggaac aatcgtgagc ggtaattgac tatttgttgt   4080
ttgttgtttg ctatttggtt gtttgttgtt gtcggttgtc agtgggtggt tgttgtagtt   4140
gctggtcgcc ggacaaatga atagcttttg ttgtgcattt ttaatgcatg gtcgagactt   4200
```

-continued

```
ttcgccggat tatgacatca ctccgaggat ggtgatggga taggttagga ctattcaaca   4260
atgtgtagca agctaataat atgataatat gatattataa tacgaaagaa agatatatcc   4320
agaagacatc atcttttcga agctatgttc ttttccaaac aaatttttac aaaataagat   4380
aagtattttt gaaaagtgag atcatcagca atcatctaga ttttcttaaa ctcaagtata   4440
tatcgaattc ttctgaaata accgaactga cttggtcata atcgacacat catcgtttag   4500
aagttaataa agcaaccttt aaccctcctc tttcgtagct tccgcggcga ggcgggtcct   4560
ggccagcgtc cgtctccccg cctcggcaga tgtatgctga gcgacaggga caagaccgtc   4620
cagccggacg cctttcgcgc ggctccatac gacgaggagt acatggagaa ccagtgccac   4680
gaacgggcca tcgaaagtga caactgttcc tacgagctgt acgccaacag cagtttcatc   4740
tatgcggagg ccaggtattt gggcctctcc caaaaagagg tgtgtccgcc gcgcttcgga   4800
tgtcgcgcat tatgattgta atcgaaatgg atggggggtc ggatgattga ttgatggctt   4860
ctacctccgt attgcagtgt caggcgatgt gctcccacga ggcgaagttc tactgccagg   4920
gtgtctcctt ctactatgta aaccaactct cgctgtccga gtgtctcctc cactcggagg   4980
acattgtatc cctgggtccg cgaagcctga agctccgtga aaactcggtg tacatgcgga   5040
gggtcaagtg cctggatggt aagatcttct ggggatgtgg tatgctcaat cttaatcgat   5100
tccttattcc gcagtccggg ttttttgcac ccgcgatgag atgaccatta agtacaatcc   5160
caaggactgg ttcgtcggca agatctatgc cagcatgcac tccaaggact gcctggccag   5220
aggatcgggc aatgggagtg ttctgctgac gctccagatc ggcagcgagg taaaggagaa   5280
ccgctgtggc atcctgcgtg cctacgaaat gacacaggaa taccaaaggt aagatgaagt   5340
ccaatgtcca gtccattttt ttaattatat catttgcatt atttagaacg ttcatatctg   5400
ctctggtggt catccaaaac aatccaaatg tgcaaaccca gggcgaccgg ctcatcaagg   5460
ttggctgtat acagagcaat gccaccacat cgctgggcgt ttcggttcgg gacagcagtg   5520
tggatagctc agagcctgtg cccagcgcca ttgcactgga gtcctcattg gagtacacag   5580
aacagtgagt gtattcttaa tagaatccct caaaatgctt aattctatca caatcgatac   5640
ctgcagcatg ttcccacacg agggtgtggt tcactacaac agcagcactg ggccccatcc   5700
gcatcccagc atctcgcttc agattttgga tctatcccac cagcacgaga ccaacgacgt   5760
gcagattgga cagaacctgg aactacagat tgtggcggag tacagcccac agcagttggc   5820
agagcacatg gagttgcagc tggcaccact acccgacttt cgtgctacct cgctggtggc   5880
caagacagcg gacaatgaga actttgtgct gctgatcgac gagcgaggat gtcccacaga   5940
tgccagtgtg tttcccgctt tggaaagggt acacacagcc agcaggagca tgttgcgcgc   6000
tcgcttccat gccttcaagt tctcaggaac ggccaacgta agcttcgatg taaagattcg   6060
cttctgcgtg gagcgctgct cgcccagcaa ttgtattagt tcatcctggc aacggagaag   6120
gcgacaggct gaccaaccag atcgtagacc ggaagaccta cgagttcaga accccgtgta   6180
catctccacg gtggtggatg tggctccgca accagacaac tttaccagat cgcaggagga   6240
attgcccctc aactacaata tccgggtgca cggtccggac cagagcaaca ccaatagtta   6300
tctgtacggc gagcggggag tgctgctcat tgctggcata gacgacccgc tgcacctgga   6360
taacgtttgc atcaaccaga gcctgctgat tgcactgttc atcttctggc tgatctgtca   6420
agttgccctg ctcttcggct gtggaatggt gctgcagcgc taccgccggc tggccaagct   6480
cgaggatgag cgacgcaggc tgcacgagga gtacctggag gcgaggagag tccactgggc   6540
```

-continued

```
ggatcaaggc ggatacacac tctaattgac ggctggaacg caatgcgtat aaaatgcatc   6600
ttaatttaat aaacataaat ctaacataaa tctaacaaat gtttgcaacc gaggataagt   6660
tcaggagttc ttcttgggat ggtagtgctc ccacttgcga tggtttagcg aattgaaatc   6720
cgggcagtgg tgagcgattt tgcgcaaata gtcggacaac ttgagcagct cggtgtccgt   6780
gccacggttg agatgagcct gacggaatgg gcggatcttt aggccggact ttgggttcat   6840
aaggaagttg cgacggatgt catcaaacat gatagtgttg ctcgagttgt attgcttgta   6900
cagggcccag attacaccaa gcggctttac gtccaccaca ccgcgctccg gcacatgaac   6960
tgatatcatg gcggtggagt ccagatagaa catcaccttg tagttatcgt tactggccac   7020
gcccagcagg cgcatctttt cctcgatcca gcgcatgctg gtggcggacc agatgacaat   7080
gtcgtagtcc tcgtaggcgg aagtcagaaa ctcgtgcaga tacggacgca ttagctccgt   7140
gcctgtttca gcaggcgatc ggtgatcgaa tagggtatag tctatgtcca ggacaagcag   7200
cttcttgccc tcacgcggcg gcgctaactc cttgatcttg tagtctcgca cacgacgctg   7260
caccttggcc aaatagacgg cggagtgctc cacggactct tcgcgttcat cggcgtcatc   7320
gaagtcgtcg accacttcgc caatattatc gggcaggctg cacgcatcct cgatatcggc   7380
ctctgtggag cccaccatca taagcttaaa gttgggcttc agctccaaag cgctgatctt   7440
cacattgtcg gctgctgtct ttcctgcaag tcattggatc ttaaaactga aatatcccga   7500
agcctaggag tgtcacgcac ctttgtactt caggttgagc agcttttgac gttccggacg   7560
cacctgtgtc ttgcggaata tctcgtgacg cagcacttcc acggtgtcct ggtcggtgag   7620
gtccaccggg tactccttac cactccattt tacaatcact accacttctt tgacctccat   7680
cttagctggt ttctattccg ctattaattt atcacaccat atatggtaat gtatgtttgt   7740
tggatagaat ccagcaagtg gtttgcaata gtgtacctta aagatattaa ctaatttatt   7800
agaagaccat ataaacagtc gagttgtcag aagtcgatag atactatcga ttgcaacgcc   7860
cggcgttatc gattgcaatc ggcttgcaat aaaaataatg atttttgat tatatttttc   7920
agagattatt aaaaaatatt ttaaattttt taaaattata tatttagcaa ttaaagaaag   7980
tcatgcaaag acatgaggaa tgtccccaag ttgccaatag gcgattgttt cgccagttca   8040
ttggccacac tggtcaccag ctgaaaacac aaaaaccgat cgtacagcat aaatttagct   8100
cgaaaatgga ctaaacaaag acagcgatcc ggaatccgag cggaaacata gtctgcatga   8160
actatctaac gatcctgctg tgcaaccgaa aaccgacgat gctctcgcgc cggaacaagg   8220
agaagtccca gcacaaggag ggcgtggtgg ggaagtacat gaagaaggac accccaccgg   8280
atatttcggt gatcaatgtg tggagcgatc agcgggccaa gaagaaatcg ctgcagcgct   8340
gtgcgagcac ctcgcccagc tgcgagttcc atccgcgcag ctcgagcacc agtcggaaca   8400
cctactcctg cacggactcg cagccggact actaccatgc tcgacgagca cagagccaga   8460
tgcccctgca gcagcactcc cactcgcatc ctcactctct gccccacccc tcccatccgc   8520
atgtgcgtag tcatcctccc ctgccgcccc accagttccg cgccagcagc aatcagttga   8580
gtcagaacag cagcaactac gttaatttcg agcagatcga gcggatgcgc cgtcagcagt   8640
cgtcgccact gctgcagacc acatcatcgc cggcgccggg agccggagga ttccagcgca   8700
gctactccac cacccagcgg cagcatcatc cccatctggg tggtgacagc tacgatgcag   8760
atcagggcct gctaagcgcc tcctatgcca acatgttgca actgccccag cggccacact   8820
cgcccgctca ctacgccgtc ccgccgcagc agcagcagca tccacagatt catcaacagc   8880
acgcctcgac gccgtttggc tccacgctgc ggttcgatcg agctgccatg tccatcaggg   8940
```

-continued

```
agcgacagcc caggtatcag ccaactaggt aaactgcctc ttgaagtact atatttgaat   9000
agatagcgcg cgattgataa agtgggtaga gataatatga gcagctcttg attaaaggaa   9060
taatccgtaa aaactacata ttgtcaaaaa gtgcttaata ttattataac ttttaaacaa   9120
tgacaatgca cgaaatgttt tattttcgaa acatttattg ttcaaagatt ttttatttga   9180
taacagattg ctttatttat ttacaataag aaaagttgat gtacaaaacc ggtttctact   9240
cgccttacaa taattaaaac aataacacaa tatatgattt tctgtacgag gaatataatg   9300
gaatatatat gatatataca acatttttaa acacattttc tcttctgttt ccacagctct   9360
ccgatgcagc agcaacaaca acaacaacaa cagcagcagc agcagctgca gcacacacaa   9420
ctggcagctc acctgggcgg cagctactcc agcgattcgt acccgatcta cgagaatccg   9480
tcccgcgtca tctcgatgcg cgccacgcag tcgcagcgat cggagtcgcc catctacagc   9540
aatacgacgg cctcgtcggc cacgctggcc gtggttccgc agcatcatca tcagggtcac   9600
ctggcggtgc catctggaag cgggggagga tccctgagcg gcagcggtcg tggtggcagt   9660
tctggcagtg ttcgcggcgc ctctacctca gtgcaatcac tgtacgtccc accgcgaact   9720
ccgcccagtg cggttgccgg agcgggaggc agtgccaatg ggtcgctgca gaaggtacca   9780
tcacagcaat cgctcacgga gcccgaggag ctgcctctgc cgcccggctg ggccactcag   9840
tacacgctac acggtcggaa atactatatt gatcacaatg cgcataccac gcactggaat   9900
catccgttgg agcgcgaagg tctgccggtg ggctggcggc gggtggtgtc caagatgcat   9960
ggcacctact atgagaacca gtataccggg cagagccaac gtcagcatcc atgcttgacc  10020
tcctactatg tctacacgac gtctgcggag ccaccgaaag cgattcgacc agaggcgtcg  10080
ctctatgccc cacccacgca cactcacaat gcactggtgc cggccaatcc ctatctgctc  10140
gaggagatcc ccaagtggtt ggccgtctac tcggaggcgg actcgtccaa ggaccacctg  10200
ctgcagttca acatgtttag cctgccggag ctggagggct tcgacagcat gctggtgcgg  10260
ctcttcaagc aggaactggg caccatcgtg ggcttctacg agcgctaccg gtaagtgagc  10320
ggccacatgc cgctgcattc tccgctctcc gaaaagccac tactctcttg ttacaccttt  10380
cagtcgcgct ttgatactcg agaagaatcg acgcgccggc cagaaccaga accaaaacca  10440
gtgacccggt gaccaggtga cgactgactc agaccacata ctcgccagca gctatatgca  10500
catcatagtg ctcctgtaat cgacctttaa cttatttaac catcgactca tcgcgaaatc  10560
agtgccttat acgaaaccag acgagatggt agccaagcag atccatgaca gttcgaatgc  10620
cttgatgaaa cgtagaattg tgctacgttc tatataacct taatgtgatt tgagcttggc  10680
gtttgtttgt aatgtgagca aagaaaatta aactggttta ctgatcatct tacctgccga  10740
gcgcaattgt aatcgatgtg ccacctgaaa ccccacaggt atttaacctg ggagtccgat  10800
tcatcgacgg atgttttgga aattcagcgc cgcgaagtgt aaataaaggg caacagttgg  10860
tggccaagtc ttactcgact tggcttggca catatttccg agttccatgc caagttttcg  10920
attcgcttgc aaaaattatg cattgggcac aagtgaatcg tggccgattc tgtattggca  10980
aaaaaaaaaa cagcgctcca atagaaagtg aatcttatgt ttgttttcgt ttggctatgc  11040
ttatttttag tcgaacctga taattcattc agtcgcctct tatcgaatgc ttataaaact  11100
ttatagtcac tgtttctgca ggtccctcaa aaacagtttc tactgctgat aagaagtttt  11160
cgaagtctgg ggagtattcg gcattggaaa ggccaaaagt tgtgttttat tatattttga  11220
acatattaaa caggatacat aaaacgagag ttttagattg taattacatt tgtcatatct  11280
```

-continued

```
tttgctaaat tgataagtaa acagaaaata tgactcgatg gatattattg actaataata  11340
tatatttagg ggtttggtat gattactttg tactgtgaga tacaagttcg tttgtcccac  11400
agatactttt caattcatag cttatcctac agatacattt caattcatag cttatcccgt  11460
agatacattt ccattcattg cttatcccac agatacattt tagcatattt tttttgaaat  11520
ttgaatttga aaaaaaagtg tttttttttt ttttgttttg agaactactc gtcttgtcaa  11580
aatatttaac tgttcccgac tgaagtgccc accttttcgg ccgccgggtt ctcaagtgca  11640
aaaataatgt ataataaaaa gccaagatac gtcggcggtc cgctctcgcc ccacttgttg  11700
ttgctgctgc cgctggtgcg tcgctgccgc tgccgcagtc gacgtcgact ccatcgctcc  11760
aatatttaaa cggatccatt ggatcgcgca ctcagtcgca ctggagagtc gccatcgcag  11820
ccatcatcat agcattccat tccacttgta gccatcggca gtcgctcaat cgtcagttgg  11880
gacacattat ttaacttcat tcttaacgtg agtgaattga tgtgttgggt ggcgatcatg  11940
catatagcat aggcaaacaa ctgttctaat ccgcattatc ttaatcacaa taatccggcg  12000
gcttatacag atgttttgcg ttagcagttg gcggctaaaa gcctctgctt gcccacatgc  12060
cagtgaaagt tctaatccgg ctcaaacaga cgcacaacaa gcgtatctcg tgcgtggaat  12120
catgaatgaa taaatgggtg ttactgttaa ctaacaatgg accttttac caatcaatcg  12180
tcttatctat caccagaatt gaaacagaat tagtgaataa cttatggtgc atatcagttg  12240
aaacatgaag attcgtgtga acgatcgtga aagatatggt gttcgaactt taaattaccc  12300
ttgtagttta ccactctcat tagttttgat ttatgtagaa ccaaaatttg gatcgtgact  12360
tgcgattagt attgcaatcg cagtgcattg cccaatctat tgattatctg caacttgtgg  12420
cagactgccg caataattcg acggacacta tcagctagct ccattgattg agataagccc  12480
gttctcacgc ggtgttttac acttcttggc aatcgccaag tcacggccct cgccatataa  12540
aaaatatagt atgaacaatc gggaatcttt tggttttacg atcgaccgac aaagcccatg  12600
tatttcctgt tacgtccatt tgggccatat aggcacataa aatgggtgct ccaacgcttg  12660
ccgtgggaaa gtgtgctcca attgcaaagt tgtaacattg agcgacattt gatgaaggtt  12720
accgactttt atctcgacaa aaacacacac gaattccaga tgaagcgagc gtgcgtagtt  12780
tgcactgcaa gttttttttt tggaacaaat agttttatgt ttatatcatt ttatatcata  12840
ttatattcct tattgattga gtgtctgcac gggtcattaa attaagaagc aaaaaaaaaa  12900
aaggtgtcag gaattgcatt ccatactcct acgagtagat atcaatttca cccgatcgtg  12960
gtcaattggt caattgaagt aattcacaat tgaatcaata caataccata tagggcttca  13020
ttgaagaaga tgccagcagg actggatgct catgcatgaa taagttgaac gttgaacgca  13080
agcagaatgg atttcagcac acaccgcctg accactttgc tgctcctcct cctggccaca  13140
ggtgagatat cgcaatccag atattgcgat ctaataatga gggaatttct cctgcccaca  13200
gttgccctgg gaaatgccca aagcagtcag ctcaccgtcg attcccatga catcaccgtt  13260
ctgctgaaca gcaacgagac ttttctggtg ttcgccaagt gagttgccat tgccgggaaa  13320
tccaaatcca aaacatatgg catcgtaaat ctattgtgcc cattacagcg gattgctaga  13380
cagcgacgtg gaagttgcgc tgggaacaga ttcggaggat catttgctcc tcgatcccgc  13440
aacgtttgtg tatccagcgg gcagtactcg aaatcagtcg gtggtgataa ctggcctcaa  13500
agccggcaac gtcaaagtgg tcgcagatag cgatgatgcg aacaaagaga tgtgagtaac  13560
ttcacgggaa tcccaactgt tcccgtacct aattggaaaa ttcacttatt ttccagtgtg  13620
aaggatgtgt tcgtacgcgt gactgtggcc aaatcgagag ctttgatcta cacctccatc  13680
```

```
atctttggct gggtttactt tgtggcctgg tcggtgtcct tctatccgca gatctggagc  13740
aactatcgcc gcaagtccgt cgagggactg aactttgatt tcctggccct caatatcgtg  13800
ggcttcaccc tgtacagcat gttcaactgc ggcctctatt tcatcgagga tctgcagaac  13860
gagtacgagg tgcgatatcc gctgggagtg aatcctgtga tgctcaacga cgtggtcttc  13920
tcactgcatg ccatgttcgc cacctgcatt acgatccttc agtgcttttt ctatcaggta  13980
ataatatata tagcaaatac cattcaatag ccttatcgcc gaagtggcaa cagttgtcgc  14040
attgaacact aattgccatc aatcaaaatg ccaaatcatt tgaatcacag cggatagtta  14100
cgatatgaag agtagataag gttttgactt gtaaaacatc catactttgt taaatttgtc  14160
cagagagcac agcaaagggt gtcgttcatt gcctacggaa tattggccat cttcgccgtg  14220
gtggtcgtcg tgtctgccgg tttggccgga ggatccgtca tccattggct ggactttctg  14280
tactactgca gttacgtcaa gctaaccatt accatcatca agtacgtgcc gcaagctctg  14340
atgaactatc gccggaagag cacctccggc tggagcatcg gcaacattct gctggatttc  14400
acgggaggaa cgctgagcat gctgcaaatg attctgaatg ctcataatta cggtaggata  14460
tagtctatca atttgtgatt ttcgaatgaa atcgtgtctg gtttccagat gattgggtgt  14520
cgattttcgg tgatcccacc aaattcggac tgggtctgtt ttccgtgctc ttcgatgtgt  14580
tcttcatgct gcagcactat gtgttttaca ggtgattgaa acattgtgtg aatatgatac  14640
ttaatctacg attatgtcat ctccactgta cacttatcat tattgctgtg ctgttttcca  14700
tttctcccca ggcattcgag ggaatcctcg agctctgacc tcaccaccgt gaccgatgtt  14760
caaaatcgaa caaatgagtc gccgccgccg agcgaagtga cgactgagaa atattagagc  14820
tgcattatca tatgtctgct gtagagaaag acttttgtgc cagtagcgct ttatgtacat  14880
ttttagaatt gtaaatatat ccgtatgccg tagctgccta agctttgtat aattcgtgcg  14940
ttttaattga aatttagttt gactaaaatt tggaatttca ccattaaata aaacttaatt  15000
ttttgtagga gccagaaatc atacggtaca ttgctcgacc attcaaaggg ctgtgcagtg  15060
aaaccaattt gctgcatacg gcgcgttatt tgcaaactaa taaatagatt gaagtattga  15120
aaaaatttca aaacagaaat tctaacttgc cgcacaatgg gcagcactgt tcgcactcgg  15180
ccaaatcctt atcgatagct tatcgatagc catggatata tgacattaag ttagccaatt  15240
tccggttagt tgacatccct ggagcacgga agattcttgc ggacacaaat cgcaactgct  15300
aaataaaatt tatttatttg agtgcacagc catgagtctt cacaagtccg cgtcgtttag  15360
cttgactttt aaccagtgag cggagatatt ttattcggtc ttacccaaca aaataatgtt  15420
gcgccttttt gcagaaacac ttcgattgtt tcgcgtagca atagtcgcac aatttttgaa  15480
gctttcaagg agttcctgga tttttgggat atcggcaacg aagtttctgc agagtcagca  15540
gttcgggtct ccagcaacgg agctttcaac ttgccgcaga gttttggcaa cgaatccaac  15600
gaatatgccc acctggctac gcctgtggat ccagcctacg gaggcaacaa cacgaacaac  15660
atgatgcagt tcacgaacaa tctggaaatt ttggccaaca ataattccga tggcaataac  15720
aaaattaatg catgcaacaa attcgtctgc cacaaggggt gagcaaattc aaaacacgcg  15780
ctccaatcga taaacattgg ctacggcgat tgttcgcgct gcgtggcgaa tggcaaaatc  15840
caaatagtcg gtggccacta cgattctgta gttttttgtt agcgaatttt taatatttag  15900
cctccttccc caacaagatc gcttgatcag atatagccga ctaagatgta tatatcacag  15960
ccaatgtcgt ggcacaaaga aaggtacagt gcggcaacaa attgatgatc gaacagtaga  16020
```

-continued

```
aaccttgcat gtagcaacac gcttgtactt gcatcattcg cgcggccaac ttgtttgtgt  16080
ttgtttatcc agccaaggcg cagtttgcca ctaagttttt atttcccttt tacactttag  16140
cactgattcc gaggatgact ccacggaggt cgatatcaag gaggatattc cgaaaacggt  16200
ggaggtatcg ggatcggaat tgtgagtacc tggtcacgtg gtcacatgtg gtttgcctgg  16260
ttgctaacta ttattgtttt tattattcca ggaccacgga acccatggcc ttcttgcagg  16320
gattaaacgt gagttgtgct tttaatgtgc aaagctatag cttactaact atttaatatt  16380
attccccgca gtccgggaat ctgatgcagt tcagccaggt gggtaacatc gattagctat  16440
tgcatcttga agcgctggga cagatcggcc tgcacgagga tcagcaggaa gctggccacc  16500
gccgagaaga cattgctgat cagtcgcatg tccagctcgt acaagcccaa gggtttaatt  16560
tggtacttgg tcaccgtgac cagcagagta aagccgtgga ctgcctgacg gtagcggctg  16620
tccgcatgct ggagattcat ctcctggaga atgactgccg atcttcgggt ggccaccaat  16680
aggtggttgc acaaatgcgt gagcaatgtg atctccgcca gcgagatgga gaggaaaacc  16740
agattgatca gcgatccaag accatcgtac ggcttgccca tgattaaggt gtccgctatg  16800
gcatagtaca gactgtagaa acccaccgtt attccgagca ggtggcatat gagcgacaga  16860
atcatggaca aggacattgg ggtcagatac tttcccgaat gcacatatat caacctatag  16920
cgatacgcca gctggtcgag ttcatccgcc aaggcgcaaa atcgctgcat gcggtagtat  16980
ttagtgtaca actttagctg gtccttcctc tgcagcagat tcacctcctg cagctgcgct  17040
tccagccgtc tgttcagagc gtacagaatc tccttcacca ccaccattgc gccaaagtag  17100
cagttattga gaaaattcga aataattaag ggaaacagcc ggtacaaggt ccagatcaag  17160
ctcatctcgg gatgctgccg cctctgttgc agtatgaaag ccacttcaat tgttagagga  17220
aaagccacgg tcttgaccag agccaaaacg atggatatgt acagcgacct gctgtccaga  17280
cggaattctt ttagggtatc aaagaagggc actttgctca acaccttggc cacatggtca  17340
ctgattatca tttgcgacac atagttaata acagccaccg taatgttcat atagctgtac  17400
agagtggtgg cgtccttcag gttgatctga ccctcctggt actccttgta gatttgccgc  17460
ccgtaaacca agctgaatgc aattgcccac agcgaagcaa aggccagatt tgcctttgag  17520
aagcggaatc tttcacgacg gcccgcccga tatcgattgg ccaggagtcc gaagacggtc  17580
ataaagccta tcagtatgat cgtcagaaat ttcaccatac gccgatgcgc gtagtcgctg  17640
gtgaagtcca tttctctcga acaattaata caaactgtga gcgcactttc cacagcatta  17700
atatctgctt aattgttttc caactaccca actgatgcca tctagaggac ctgtcaagta  17760
gccggacact atcgggacac atcgcgaaac gcatgtattt caccggccgt ccagaaacca  17820
actgagcatg cgttgtgcta ctactagcca caaacaaaag agcataagaa gcgtgaggga  17880
agcggcattc cttgcgtgac tcagccgctg cctgcaattt cataagagcg acatgacgtc  17940
aaagtcgctt cgaagttcac tttcagttgg aggacagaac aaaacactct tatctagccg  18000
attagcacgg tgcactcctt cccgtcgtca tcgtttagcg agaatttcaa gcacttgtga  18060
aaaatagaat agaatacaaa acaaatcgcc agtccatttg taactcgagc aagctggaac  18120
atgaagctct atcagctcta tgagcgcaaa gtgtgaaccc ttatatgatt gcgagttaag  18180
ttgacattca aataatatct tgtttttgct tacagcaatc cgtgctgcgc gaaatgatgc  18240
tgcaggacat tcagatccag gcgaacacgc tgcccaagct agagaatcac aacatcggtg  18300
gttattgctt cagcatggtt ctggatgagc cgcccaagtc tctttggatg tactcgattc  18360
cgctgaacaa gctctacatc cggatgaaca aggccttcaa cgtggacgtt cagttcaagt  18420
```

-continued

```
ctaaaatgcc catccaacca cttaatttgc gtgtgttcct ttgcttctcc aatgatgtga  18480
gtgctcccgt ggtccgctgt caaaatcacc ttagcgttga gccttgtaag tgaagataac  18540
aatacagatc gaacaggatt atttaactat catttgtaca aacctttagt gacggccaat  18600
aacgcaaaaa tgcgcgagag cttgctgcgc agcgagaatc ccaacagtgt atattgtgga  18660
aatgctcagg gcaagggaat ttccgagcgt ttttccgttg tagtccccct gaacatgagc  18720
cggtctgtaa cccgcagtgg gctcacgcgc cagaccctgg ccttcaagtt cgtctgccaa  18780
aactcgtgta tcgggcgaaa agaaacttcc ttagtcttct gcctggagaa agcatggtaa  18840
ggtgacagca aaactctaga tggctagaac aaagcttaac gtgttttctt tcttgcagcg  18900
gcgatatcgt gggacagcat gttatacatg ttaaaatatg tacgtgcccc aagcgggatc  18960
gcatccaaga cgaacgccag ctcaatagca agaagcgcaa gtccgtgccg gaagccgccg  19020
aagaagatga gccgtccaag gtgcgtcggt gcattgctat aaagacggag gacacggaga  19080
gcaatgatag ccgagactgc gacgactccg ccgcagagtg gaacgtgtcg cggacaccgg  19140
atggcgatta ccgtctggct attacgtgcc ccaataagga atggctgctg cagagcatcg  19200
agggcatgat taaggaggcg gcggctgaag tcctgcgcaa tcccaaccaa gagaatctac  19260
gtcgccatgc caacaaattg ctgagcctta agagtaagca gtgaatcgga ggacaaagag  19320
attaagcttt acttaccgaa ctttcctttc agaacgtgcc tacgagctgc catgacttct  19380
gatctggtcg acaatctccc aggtatcaga tacctttgaa atgtgttgca tctgtggggt  19440
atactacata gctattagta tcttaagttt gtattagtcc ttgttcgtaa ggcgtttaac  19500
ggtgatattc cccttttggc atgttcgatg gccgaaaaga aaacattttt atatttttga  19560
tagtatactg ttgttaactg cagttctatg tgactacgta acttttgtct accacaacaa  19620
acatactctg tacaaaaaag ccaaaagtga atttattaaa gagttgtcat attttgcaaa  19680
catatcctcg tggtgtacgc caatgcccag agcctactgt acccccaccg tggagcacat  19740
gctatgtgac atgtgtggct tgtgtgcggt caatgcactc aggatgcaac tcagctagct  19800
agctgctaat atgtcaaaat tgctgcgtcg catttacata ctttatttat acccgtatct  19860
gcacgtcttt ggttttagtt ctatgctttc aaaaaaaaaa aaacaacctc aagcagggcg  19920
catgcgttgc gccagcgttg cacatgtgcg aggatgcaaa aaagtgcaac aaacaccaga  19980
tgttgacact gtgccgctgc agctgcaggc gactttagct tttgccacat gcggcagcta  20040
aatgtttact ctagcccacc gatcgctgtt cattgaccta gggcaggggc attaagtgcg  20100
ccctaatcgt aacggaatga tagcctctgt gtccaaaaat tcagccaaag cggatgcact  20160
cacttccatt tggggcctgt ccttcttcga ccggctgcca cttccactac cagtttggca  20220
ccacgaaaat gggtcgttca aagtgctcaa aacccagcgg agcaactcac tcaattctcg  20280
ttggacgagc gcacagaaaa gtggttttgg atacgagttg agttcgagag acctttctgc  20340
actgggaaca tacatgcggc tttgtgtaac agaataataa agtacgcaaa catatctgta  20400
atacttaaag cacaaagaac aaatataaat gtatcataat ttgtttaatt atttattcga  20460
ggtttccaaa caagtcattc tgataacaaa agttgtaaaa ataaaatcca ctaaaattaa  20520
atatcaccca cttctcagaa taagcacagc tgtatatact tcagtatata tttttttcag  20580
tgcacttttc ccaagcgatg caatcgcctt agaagcccaa ttaaatacgt ttctttgatt  20640
ggcgggtgcc aaaaggttga caattcgaaa gtggcgcaca ctgggaggca gtgactcata  20700
atttacataa ttatttcggg aagatattaa gactcatact atattcaagc agttgtttat  20760
```

-continued

```
cattttaaac tggcagatac cccatcttta cggaccagat aaagggaaag caaacacggc  20820
tgggctctta tcggctacga tcttcatccg cagttcccac tgtgcgcgtg gggaaaacaa  20880
tatggcccaa acacataaaa aacaacaaaa aaaggaaaca accacagaaa gccgggctaa  20940
gacgtcaggt gaaacgcagt agcttcactc gcgactcggc gcttccactc aaaggtgcta  21000
ccgctgccca ctcaaatctg cagctcgtag atacgaaaac cagatagcgt cgagcggctg  21060
gcgatcttca ctcaatgggg ggaaatactg ctatagagtc gaaagcttgt acacgtagtt  21120
tggcattcgc agtcgcttgt tggcgttttt agtctgctgc ctgatcttcg acgcgctgca  21180
gctgttttgg agtcgccgcg agtgccatat ttgctttgac cgcgaaaatt tctgggctaa  21240
aaacagagat atttgagata cagatacata tatctcatat cacatattag ccaattgtgg  21300
gtgcaacaag ctgtgagtga tggtggagac ggcaacgaca acgaccataa cccgcaccac  21360
caccgccgtt ccggctggtg cagtaacggt aacaggaccc actgcctcgg ccacgcccac  21420
cgcgacacag gcggccgcgc aggcgcatcg caacgatgag accacccggg ccatcttcaa  21480
tctgaaagtc atcgtctttc tgctcctcct gcctctggtc ctgctggccg tctttctcaa  21540
gcacctgttg gattacctat tcgcgctggg actcaaggag aaggatgtca gtggcaaggt  21600
ggcactggtg agttgcattc gagtgcccat tggggctaac aaatggctgc aatgagcgtc  21660
tggcaaatga gccattaata aggctagtca gatgcacatc agacatggat gcacttagaa  21720
aatgcagtcg catttcatgt taagtactga cattaaaaaa gagatatatg tctgtgttta  21780
gatacatctt tgggtaccaa attaggttca gatacttcgt aaagaaattg gtaatggtat  21840
actttaatcg ttggcttcat gtgaatttgt tttcccagta tccgcttcta agtgatcttg  21900
tatctgacga ctacttagcc aaccagaaac gtcacgcact ttccttttcc agtggctgcc  21960
tccgggtttc caccacgccc acctttggct cacccacctt ttccccttc ccgcttttct  22020
ttgcttttta tttctcctct tttttttttt tttgatgtca ctgccattag ggtgcggtcg  22080
atcgcttagt actgtgttat taatgtaaat atttatgcgt ttggtgccca gcttggttag  22140
ttgttggcca attgtttagt tgtgtccaca gagccgcgtc tttggtgcca cggacagtta  22200
atgtgacata atttcgctgt aagcgctgca atcaaagtga atctccagct gaaatcgtgc  22260
tcatggcaac catatcgcgc tccaataatc acatatgcat cttggggcgt cgaattatgg  22320
agaagtcaat tgccaatggg cgccaatgcc actggacaag gtcaagtgat gatgccgctg  22380
ccgatgctcc atatcgtaaa gaacctgatc gaattcggaa cccattagca tgcttttcag  22440
gctttttata gtgggcgtgt gccggccata agcgtctcac gtagcgtatt aatgattcac  22500
agcggcccga cttttgtttt agtctcagct tttttttcg atcgttccct cagatatcgt  22560
tttctcagat acagatacac atacagatac atttttgttg cggttgcaca gtggtatttt  22620
cgggtggcag ggactggaga attcccatgc caactgttag cagcaactta attataagat  22680
tgactttcgt tgataagttc tattgacatc atggttgcgg aattcgagtt atttcagctc  22740
aaaaataccc ccttttcga caccactggc caacggccaa ctgcaaactg gttttgcgtg  22800
tgtcgctata tttatttcca agatgaacga aaagagcgca aaaatgcaaa cctcagaaag  22860
ttcacttttg ttttcagtct aatgtttgtg tttacaaaca atagagtgta gaatttcgat  22920
gggccaaagt atctgcaagt gtgtagcatg ccgggtatct ctcagatgcg tagataaaac  22980
tcaactactg ttgccgctgt taatttgcat atgatattga aattcttcgg ctgttctata  23040
atcacaacaa ctgcgcattt gttattgttt tccccattgc tagtcgctaa cgtgccaaac  23100
tctgaattga actcattccg gcttacattt cgattcaccc aactaccgca cacccaaaac  23160
```

-continued

```
ggcggctgag gtcacccagt gggcttcaat tacggtcaaa agtcactcaa ttgtgcccca  23220
gagggtcggc ccaccgagcg tatgagtaat gccattcata agtcgcctct gccgctgttg  23280
ctgctgctca cataattgtc cgtaaatgag gtttttgttc aatgcgaagt cacattagct  23340
cgagttgatt gtttgcaaat taagctaatt aatttacttg agtatacgag tgtaatgtga  23400
gtaacctgtg atttaaaccc aggtgaccgg cggaggcagt gggctgggtc gcgagatctg  23460
cttggaactg gcgcggcggg gctgcaagct ggccgtcgtt gatgtcaact ccaagggatg  23520
ttacgaaacg gtggagctgc tctccaagat tccacgctgc gttgccaagg cctacaaggt  23580
gagttcacta gctgcttgga tatttaatgg tttgataaca agaatcttta ttccagaacg  23640
acgtgtcatc gcctcgcgag cttcaactga tggccgccaa ggtggagaag gaactgggtc  23700
ccgtggacat tctggtcaac aatgcctccc tcatgcccat gacttcaaca cccagtctga  23760
agagcgatga aatcgacaca atactgcagc tcaatctggg ctcctacata atggtgagtg  23820
tgtgcttctg aaaatgggac aaatataaaa cttcttgatt ttgcagacca ccaaggagtt  23880
cctgccgaag atgataaacc gcaagtccgg tcatctggtg gcagtaaatg ccttagcggg  23940
taagcttact tggttaaagt gcttaccact tcattgatac ctatgtatat ataactcgca  24000
tttaggtcta gttccactgc caggagcggg catctacacg gccaccaaat acggaatcga  24060
gggcttcatg gaatcgctgc gagctgagct gcgattgtcc gactgtgact acgttcgcac  24120
cacggtggcc aatgcctatc tgatgaggac cagcggagat cttccactgc tcagtgatgc  24180
ggggtaagat tggtttatag tttgggcaga tcacttggtc tcatgcggct actacattta  24240
gcattgccaa gagctatccc ggactgccca caccatatgt ggccgagaag attgtcaagg  24300
gcgtgttgct gaacgagcgc atggtgtatg tgccaaaaat attcgcactc agtgtatggc  24360
tgctcaggtg agaattgaat tagcccaggt aaccagcgat tatttctaac gattattgtt  24420
gtcgccttgc tttagactgt tgcccaccaa gtggcaggat tacatgctgc ttcgcttcta  24480
ccacttcgat gtgcgcagct cccacctgtt ttactggaag tagggcacag gagaaggcac  24540
atccccaccc agaagcattt actcctgttt gtttcccaat tgcagttctt tattcaactg  24600
ttgcttacgc taggtgtaca tgtttagcta tttatacgaa tctttaactt aaattaaatc  24660
tatatcctaa cattagaatt acgtccggtt ggcctttcct attttatttc gtataagccg  24720
aagttgttcg gagtagcaca tcctctcgga ctgctggacg caggacctcc gttcgtagtg  24780
ccaagtgtag ttcaagtggc atcgatggac cagcttggag ccactggagc agtagtagaa  24840
gtaggcgcag ttccgtggat gtggcataaa gccatagact ccctcctggc agttgatgat  24900
attctctcgc gtttgcatgc gattgcagga cactagatga gcaggagtac aggccttggc  24960
cagtccagcc ccctcgtagc agaccatata aggataacat ggtccggcat tgggtaaaag  25020
tcgcagggta atcgccaatg gttccgcttt ctgagctggc ttcttgacca tcgaggggga  25080
tttagtggtt atgcctacgg gatcccggca tctcgacacc aactttcgat ccaaacagcg  25140
ttccaatttt tcgtcgtagt aatgaccatc caagcactcg gcctcaaagg atcctggacc  25200
ggcacaatat atgtatttgg agcaattgct agagctggcg acataaactc ccaattgtgg  25260
agcactggca cactcttcga actccagggc actggatcga tgacccagca aggtcaccaa  25320
aataattgtt aagaaggtta cagctcccat ttcatttatt tttttaacga ccgaaatagc  25380
gggatgactt ctgtagactg acttcatcga tgatgggttg agtatatttt tgcatgtgct  25440
ccaactgata aagaagacaa gttattccat cgattactac gctggttatc gtctggtaga  25500
```

-continued

```
taccgctaat gagcacatgg cagtaactgc cacgcccact ctgggcggtc tcggtaattt  25560

gcattttcgt agcatacttc gcagcagcag caaagcaacc gagtatttaa tgataccaca  25620

ccgcagcata atgctcgact gggcgccggt tcaataaaaa ttgaaaatgc actcaattcg  25680

caattaagtg tcgccacttc cgtacggaca agcggacaaa cggacggaca agcggacaaa  25740

tggacggata aacggacgga tggatggtcg tcgaacgata ccattcaggc cattcaatcc  25800

attcatcgca gtcatcctca ttattatttc catcgtcatc gtggtcgttg ctggtcggag  25860

ttaagcgatg gccatcgatt taatatccga tgagatattc ataacttgca attaggtttg  25920

gtggctctgc gctttacgta aatgattgcg tagccgatta atgaagaatt accagtgcaa  25980

atggctggga tctgtgggca ttatccaatt gaccaactac catgctaccc cactaccatt  26040

accattacca taatgtgcaa tgtgccaatt gggctcaaat taaaagtttt attaattgtc  26100

aattaaacgc tgtcgcccag cagctgcttt gtggcataat ttttgggtca atctgcatat  26160

ctgattaaca ggttataccg ctcagtctac tacatatacc atgcaccaga tgccgcgggg  26220

cacagacaac aagaagtaaa agaaaggacc ccatatggtg ccgacggctc aagtgattaa  26280

gtgcacgacg agatcttcaa atgcagtgca acatgtgcac aaatacaaaa cacacacaca  26340

cacacacaca cacgcatatt gaaaatgtat gtaaattcta attaagattg tggatgaaga  26400

cccccagcac cttgatactt ctgctcaatg cgcattgcgc atgcgcagcc ccgcatccga  26460

agatccataa aaatagctca ctaattattt gtgtgctagg gttacagttc tcataaaaaa  26520

caaacaaact gtcgggcgtt ttatggatct tctgcctcta tggcctcaat gcccccgcga  26580

agttttcgat ccccattcga ttcgaaaccg aagaagagct acgaccaatc acttttcaat  26640

tcctatgagc agttgagcat caattgattt cgatatgaaa ataaaataca tttatttatt  26700

atcacattac gtatcacagc cattcgcccg cctacgccct ggcatctgga tcgccacatc  26760

catcgtgcgg accttgtgcc ggcatttccg agctgattag cctccgaatc tcgaccagaa  26820

cccggtccgt tcgagcctcc aggttgtcga gggcggtgtt taggtcatcc aagctggaat  26880

tgactctggc catcagacgc tccgagttgt tggtcagctc gatgaggtca tcgaaactgc  26940

tggcctggcg actctccatc gatatcctgt ccagatccag ctgcagctgc tcatcggcgc  27000

tgtccatctg ggctttaagg gctggaaaac aactttcgat ttaaatttaa atttttttca  27060

ccctaaatca tgattttcgg tgttattttg tgccatgcga tccgaagtgt aaagcaaatt  27120

tgacttggtt tgttttgcta tcgaacataa ttaaagttgc ttaccataaa ccaatttaat  27180

ttaattgtaa ttgcagctaa ctggcttttg ggtacttttg cttttaacgc caaatgtgaa  27240

atattaagta tattttattt aagcgatggc acctgtaaat tgagatttaa ggggggtatat  27300

taaatgggtg aacttgatga ttttttttt tcatcaaacg tttattaaag tctattgctt  27360

aaaaaaatga aagtaaattg cttgccattt taggaggata tttttgaaaa atcgttacaa  27420

ctttt                                                             27425
```

<210> SEQ ID NO 19
<211> LENGTH: 1781
<212> TYPE: DNA
<213> ORGANISM: Drosophila melanogaster

<400> SEQUENCE: 19

```
gaattcggca cgagacgcca tacaaaaagt tggaactgag tggaatcgga gtactatata     60

gccagccgat cccttccaga gcgccggaag agtagctcac atccgaaccc acgtccccga    120

gccgatgtcg cggcgggaat agagcgattc gcagtccaaa cacgatgata aaccccattg    180
```

-continued

```
catccgagtc ggaggccatc aattcggcca cctatgtgga caactatatc gattcggtgg    240

aaaatctgcc ggacgacgtg cagcgccagt tgtcacgcat ccgcgacata gacgtccagt    300

acagaggcct cattcgcgac gtagaccact actacgacct gtatctgtcc ctgcagaact    360

ccgcggatgc cgggcgacgg tctcgaagca tctccaggat gcaccagagt ctcattcagg    420

cgcaggaact gggcgacgaa aaaatgcaga tcgtcaatca tatgcaggag ataatcgacg    480

gcaagctgcg ccagctggac accgaccagc agaacctgga cctgaaggag gaccgcgatc    540

ggtatgcgct cctggacgat ggcacgcctt cgaagctgca acgcctgcag agcccgatga    600

gggagcaggg caaccaagcg ggcactggca acggtggcct aaatggaaac ggcctgcttt    660

cggccaaaga tctgtacgcc ttgggcggct atgcaggtgg tgttgtgcct ggttctaatg    720

ccatgacctc cggcaacggt ggcggctcaa cgcccaactc ggagcgctcg agccatgtca    780

gtaatggtgg caacagcggc tccaatggca atgccagcgg cggaggaggc ggagaactgc    840

agcgcacagg tagcaagcgg tcgaggaggc gaaacgagag tgttgttaac aacggaagct    900

ctctggagat gggcggcaac gagtccaact cggcaaatga agccagtggc agtggtggtg    960

gcagtggcga gcgcaaatcc tcgttgggcg gtgccagtgg agcgggacag ggacgaaagg   1020

ccagtctgca gtcggcttct ggcagtttgg ctagcggctc tgcagccacg agcagtggag   1080

cagccggagg tggtggtgcc aacggagccg gcgtagttgg tggcaataat tccggcaaga   1140

agaaaaagcg caaggtacgc ggttctgggg cttcaaatgc caatgccagt acgcgagagg   1200

agacgccgcc gccggagacc attgatccgg acgagccgac ctactgtgtc tgcaatcaga   1260

tctcctttgg cgagatgatc ctgtgcgaca atgacctgtg ccccatcgag tggttccatt   1320

tttcgtgcgt ctccctggta ctaaaaccaa aaggcaagtg gttctgcccc aactgccgcg   1380

gagaacggcc aaatgtaatg aaacccaagg cgcagttcct caaagaactg gagcgctaca   1440

acaaggaaaa ggaggagaag acctagtcta ttaggccagc ctatccaacc cattgctctg   1500

tgtctaacac caggctctgt aaaatattcg atcctaagat ttaccttaat gtatatttag   1560

tgactttctt agacccgatc ccttttcgac tttcccctct ttcacccagt ttagatccct   1620

cgcttctatg gttataggtc gtcagttttc atttaaagtt tctgtacaaa caatatcttt   1680

ctcaatgtaa acacacaaaa actcgtataa ttagagtaca cctaaactta atttatggta   1740

ataaacgttg atattcaaaa aaaaaaaaaa aaaaaactcg a                        1781
```

<210> SEQ ID NO 20
<211> LENGTH: 433
<212> TYPE: PRT
<213> ORGANISM: Drosophila melanogaster

<400> SEQUENCE: 20

```
Met Ile Asn Pro Ile Ala Ser Glu Ser Glu Ala Ile Asn Ser Ala Thr
1               5                   10                  15

Tyr Val Asp Asn Tyr Ile Asp Ser Val Glu Asn Leu Pro Asp Asp Val
            20                  25                  30

Gln Arg Gln Leu Ser Arg Ile Arg Asp Ile Asp Val Gln Tyr Arg Gly
        35                  40                  45

Leu Ile Arg Asp Val Asp His Tyr Tyr Asp Leu Tyr Leu Ser Leu Gln
    50                  55                  60

Asn Ser Ala Asp Ala Gly Arg Arg Ser Arg Ser Ile Ser Arg Met His
65                  70                  75                  80

Gln Ser Leu Ile Gln Ala Gln Glu Leu Gly Asp Glu Lys Met Gln Ile
```

-continued

```
                85                  90                  95

Val Asn His Met Gln Glu Ile Ile Asp Gly Lys Leu Arg Gln Leu Asp
            100                 105                 110

Thr Asp Gln Gln Asn Leu Asp Leu Lys Glu Asp Arg Asp Arg Tyr Ala
        115                 120                 125

Leu Leu Asp Asp Gly Thr Pro Ser Lys Leu Gln Arg Leu Gln Ser Pro
    130                 135                 140

Met Arg Glu Gln Gly Asn Gln Ala Gly Thr Gly Asn Gly Gly Leu Asn
145                 150                 155                 160

Gly Asn Gly Leu Leu Ser Ala Lys Asp Leu Tyr Ala Leu Gly Gly Tyr
                165                 170                 175

Ala Gly Gly Val Val Pro Gly Ser Asn Ala Met Thr Ser Gly Asn Gly
            180                 185                 190

Gly Gly Ser Thr Pro Asn Ser Glu Arg Ser Ser His Val Ser Asn Gly
        195                 200                 205

Gly Asn Ser Gly Ser Asn Gly Asn Ala Ser Gly Gly Gly Gly Gly Glu
    210                 215                 220

Leu Gln Arg Thr Gly Ser Lys Arg Ser Arg Arg Arg Asn Glu Ser Val
225                 230                 235                 240

Val Asn Asn Gly Ser Ser Leu Glu Met Gly Gly Asn Glu Ser Asn Ser
                245                 250                 255

Ala Asn Glu Ala Ser Gly Ser Gly Gly Gly Ser Gly Glu Arg Lys Ser
            260                 265                 270

Ser Leu Gly Gly Ala Ser Gly Ala Gly Gln Gly Arg Lys Ala Ser Leu
        275                 280                 285

Gln Ser Ala Ser Gly Ser Leu Ala Ser Gly Ser Ala Ala Thr Ser Ser
    290                 295                 300

Gly Ala Ala Gly Gly Gly Gly Ala Asn Gly Ala Gly Val Val Gly Gly
305                 310                 315                 320

Asn Asn Ser Gly Lys Lys Lys Lys Arg Lys Val Arg Gly Ser Gly Ala
                325                 330                 335

Ser Asn Ala Asn Ala Ser Thr Arg Glu Glu Thr Pro Pro Pro Glu Thr
            340                 345                 350

Ile Asp Pro Asp Glu Pro Thr Tyr Cys Val Cys Asn Gln Ile Ser Phe
        355                 360                 365

Gly Glu Met Ile Leu Cys Asp Asn Asp Leu Cys Pro Ile Glu Trp Phe
    370                 375                 380

His Phe Ser Cys Val Ser Leu Val Leu Lys Pro Lys Gly Lys Trp Phe
385                 390                 395                 400

Cys Pro Asn Cys Arg Gly Glu Arg Pro Asn Val Met Lys Pro Lys Ala
                405                 410                 415

Gln Phe Leu Lys Glu Leu Glu Arg Tyr Asn Lys Glu Lys Glu Glu Lys
            420                 425                 430

Thr
```

<210> SEQ ID NO 21
<211> LENGTH: 2666
<212> TYPE: DNA
<213> ORGANISM: Drosophila melanogaster

<400> SEQUENCE: 21

```
cattttgtac agtctaaacg gggattcgcg taaactacgc agaaatataa acaaacaaaa      60

actagtagac tatagaatat aaacagtttc ctaccaatgg agacttgtga agtggaggga     120
```

-continued

```
gaggcggaga cgctggtgag acgcttctcc gtcagctgcg agcaattgga gctggaagcg    180
agaattcagc aaagcgctct gtccacctac catcgcttgg atgcggtcaa cgggctgtcc    240
accagcgagg cagatgccca ggagtggctg tgttgcgccg tctacagcga actgcagcgc    300
tcgaagatgc gcgatattag ggagtccatc aacgaggcaa acgattcggt ggccaagaac    360
tgctgctgga acgtgtcact aacccgtctg ctgcgcagct ttaagatgaa cgtgtcccag    420
tttctacgcc gcatggagca ctggaattgg ctgacccaaa acgagaacac tttccagctg    480
gaggttgagg aactgcgttg tcgacttggt attacttcga cgctgctgcg gcattataag    540
cacatctttc ggagcctgtt cgttcacccg gcaagggtgc ggacccgggt gccgcgaatc    600
actaccaagc gctgtatgag ttcggttggt tgctcttcct ggtcattcgc aacgagttac    660
ccggttttgc gattacaaac ctgatcaacg gctgtcaggt gctcgtttgc acaatggatc    720
tcctttttcgt gaacgcctta gaggtgcccc gatccgtagt tatccgccgg gagttctctg    780
gagtgcccaa gaattgggac accgaagact tcaatcctat tttgctaaat aaatatagcg    840
tgctagaagc actgggagaa ctgattcccg agctaccagc gaagggagtg gtgcaaatga    900
agaacgcctt tttccacaaa gccttaataa tgctctatat ggaccatagt ctagttggag    960
acgacaccca tatgcgggag atcattaagg agggtatgct agatatcaat ctggaaaact   1020
taaatcgcaa atacaccaat caagtagccg acattagtga gatggacgag cgtgtgctgc   1080
tcagcgtcca gggggcgata gagaccaaag ggactctcc taaaagccca cagctcgcct   1140
tccaaacaag ctcgtcacct tcgcatagga agctgtccac ccatgatcta ccagcaagtc   1200
ttcccctaag cattataaaa gcattcccca agaaggaaga cgcagataaa attgtaaatt   1260
atttagatca aactctggaa gaaatgaatc ggacctttac catggccgtg aaagattttt   1320
tggatgctaa gttgtctgga aaacgattcc gccaggccag aggcctttac tacaaatatt   1380
tgcagaaaat tttgggaccg gagctggttc aaaaaccaca gctgaagatt ggtcagttaa   1440
tgaagcagcg caagcttacc gccgccctgt tagcttgctg cctggaactg gcacttcacg   1500
tccaccacaa actagtggaa ggcctaaggt ttccctttgt cctgcactgc ttttcactgg   1560
acgcctacga ctttcaaaag attctagagt tggtggtgcg ctacgatcat ggttttctgg   1620
gcagagagct gatcaagcac ctggatgtgg tggaggaaat gtgcctggag tcgttgattt   1680
tccgcaagag ctcacagctg tggtgggagc taaatcaaag acttccccgc tacaaggaag   1740
tcgatgcaga aacagaagac aaggagaact tttcaacagg ctcaagcatc tgccttcgaa   1800
agttctacgg actggccaac cggcggctgc tccttctgtg taagagtctt tgcctcgtgg   1860
attcctttcc ccaaatatgg cacctggccg agcactcttt caccttagag agtagccgtc   1920
tgctccgcaa tcgacacctg gaccaactgc tgttgtgcgc catacatctt catgttcggc   1980
tcgagaagct tcacctcact ttcagcatga ttatccagca ctatcgccga cagccgcact   2040
ttcggagaag cgcttaccga gaggttagct tgggcaatgg tcagaccgct gatattatca   2100
ctttctacaa cagtgtgtat gtccaaagta tgggcaacta tggccgccac ctggagtgtg   2160
cgcaaacacg caagtcactg gaagaatcac agagtagcgt tggtattctg acggaaaaca   2220
acttccaacg aattgagcat gagagccaac atcagcatat cttcaccgcc ccctcccagg   2280
gtatgccaaa gtggctcctg ctccagtcat ccaccttcat ctcccgccgc atcaccactt   2340
tccttgcaaa gctcgcccaa cgtaaagcgt gctgcttcga gtaacgactt gatgagagag   2400
atcaagcgac caaacatcct gcggcgtcgc cagctttcag tgatctaata accaatcaaa   2460
aaaggcttaa atacttggct gcattttacg cagctagctt agtatatttc ttaaactcaa   2520
```

-continued

```
aaatggtaat taaataatgt ttaaattata gatattttat taacttgttc aagtaagtta   2580

aaagcttttg cttttgtaaa aataaaggaa taactgccac tcgtagttta aataaatttt   2640

taaaaaaaaa aaaaaaaaaa ctcgag                                          2666


<210> SEQ ID NO 22
<211> LENGTH: 556
<212> TYPE: PRT
<213> ORGANISM: Drosophila melanogaster

<400> SEQUENCE: 22

Met Asp Leu Leu Phe Val Asn Ala Leu Glu Val Pro Arg Ser Val Val
1               5                   10                  15

Ile Arg Arg Glu Phe Ser Gly Val Pro Lys Asn Trp Asp Thr Glu Asp
            20                  25                  30

Phe Asn Pro Ile Leu Leu Asn Lys Tyr Ser Val Leu Glu Ala Leu Gly
        35                  40                  45

Glu Leu Ile Pro Glu Leu Pro Ala Lys Gly Val Val Gln Met Lys Asn
    50                  55                  60

Ala Phe Phe His Lys Ala Leu Ile Met Leu Tyr Met Asp His Ser Leu
65                  70                  75                  80

Val Gly Asp Asp Thr His Met Arg Glu Ile Ile Lys Glu Gly Met Leu
                85                  90                  95

Asp Ile Asn Leu Glu Asn Leu Asn Arg Lys Tyr Thr Asn Gln Val Ala
            100                 105                 110

Asp Ile Ser Glu Met Asp Glu Arg Val Leu Leu Ser Val Gln Gly Ala
        115                 120                 125

Ile Glu Thr Lys Gly Asp Ser Pro Lys Ser Pro Gln Leu Ala Phe Gln
    130                 135                 140

Thr Ser Ser Ser Pro Ser His Arg Lys Leu Ser Thr His Asp Leu Pro
145                 150                 155                 160

Ala Ser Leu Pro Leu Ser Ile Ile Lys Ala Phe Pro Lys Lys Glu Asp
                165                 170                 175

Ala Asp Lys Ile Val Asn Tyr Leu Asp Gln Thr Leu Glu Glu Met Asn
            180                 185                 190

Arg Thr Phe Thr Met Ala Val Lys Asp Phe Leu Asp Ala Lys Leu Ser
        195                 200                 205

Gly Lys Arg Phe Arg Gln Ala Arg Gly Leu Tyr Tyr Lys Tyr Leu Gln
    210                 215                 220

Lys Ile Leu Gly Pro Glu Leu Val Gln Lys Pro Gln Leu Lys Ile Gly
225                 230                 235                 240

Gln Leu Met Lys Gln Arg Lys Leu Thr Ala Ala Leu Leu Ala Cys Cys
                245                 250                 255

Leu Glu Leu Ala Leu His Val His His Lys Leu Val Glu Gly Leu Arg
            260                 265                 270

Phe Pro Phe Val Leu His Cys Phe Ser Leu Asp Ala Tyr Asp Phe Gln
        275                 280                 285

Lys Ile Leu Glu Leu Val Val Arg Tyr Asp His Gly Phe Leu Gly Arg
    290                 295                 300

Glu Leu Ile Lys His Leu Asp Val Val Glu Glu Met Cys Leu Glu Ser
305                 310                 315                 320

Leu Ile Phe Arg Lys Ser Ser Gln Leu Trp Trp Glu Leu Asn Gln Arg
                325                 330                 335

Leu Pro Arg Tyr Lys Glu Val Asp Ala Glu Thr Glu Asp Lys Glu Asn
```

-continued

```
            340                 345                 350

Phe Ser Thr Gly Ser Ser Ile Cys Leu Arg Lys Phe Tyr Gly Leu Ala
        355                 360                 365

Asn Arg Arg Leu Leu Leu Leu Cys Lys Ser Leu Cys Leu Val Asp Ser
    370                 375                 380

Phe Pro Gln Ile Trp His Leu Ala Glu His Ser Phe Thr Leu Glu Ser
385                 390                 395                 400

Ser Arg Leu Leu Arg Asn Arg His Leu Asp Gln Leu Leu Leu Cys Ala
                405                 410                 415

Ile His Leu His Val Arg Leu Glu Lys Leu His Leu Thr Phe Ser Met
            420                 425                 430

Ile Ile Gln His Tyr Arg Arg Gln Pro His Phe Arg Arg Ser Ala Tyr
        435                 440                 445

Arg Glu Val Ser Leu Gly Asn Gly Gln Thr Ala Asp Ile Ile Thr Phe
    450                 455                 460

Tyr Asn Ser Val Tyr Val Gln Ser Met Gly Asn Tyr Gly Arg His Leu
465                 470                 475                 480

Glu Cys Ala Gln Thr Arg Lys Ser Leu Glu Glu Ser Gln Ser Ser Val
                485                 490                 495

Gly Ile Leu Thr Glu Asn Asn Phe Gln Arg Ile Glu His Glu Ser Gln
            500                 505                 510

His Gln His Ile Phe Thr Ala Pro Ser Gln Gly Met Pro Lys Trp Leu
        515                 520                 525

Leu Leu Gln Ser Ser Thr Phe Ile Ser Arg Arg Ile Thr Thr Phe Leu
    530                 535                 540

Ala Lys Leu Ala Gln Arg Lys Ala Cys Cys Phe Glu
545                 550                 555


<210> SEQ ID NO 23
<211> LENGTH: 9
<212> TYPE: PRT
<213> ORGANISM: Any Insect

<400> SEQUENCE: 23

Arg Ile Cys Ser Cys Pro Lys Arg Asp
1               5


<210> SEQ ID NO 24
<211> LENGTH: 9
<212> TYPE: PRT
<213> ORGANISM: Any Insect

<400> SEQUENCE: 24

Lys Ile Cys Ser Cys Pro Lys Arg Asp
1               5


<210> SEQ ID NO 25
<211> LENGTH: 9
<212> TYPE: PRT
<213> ORGANISM: Any Insect

<400> SEQUENCE: 25

Arg Val Cys Ser Cys Pro Lys Arg Asp
1               5


<210> SEQ ID NO 26
<211> LENGTH: 9
<212> TYPE: PRT
<213> ORGANISM: Any Insect
```

-continued

<400> SEQUENCE: 26

Lys Val Cys Ser Cys Pro Lys Arg Asp
1 5

<210> SEQ ID NO 27
<211> LENGTH: 9
<212> TYPE: PRT
<213> ORGANISM: Any Insect

<400> SEQUENCE: 27

Arg Ile Cys Thr Cys Pro Lys Arg Asp
1 5

<210> SEQ ID NO 28
<211> LENGTH: 9
<212> TYPE: PRT
<213> ORGANISM: Any Insect

<400> SEQUENCE: 28

Lys Ile Cys Thr Cys Pro Lys Arg Asp
1 5

<210> SEQ ID NO 29
<211> LENGTH: 9
<212> TYPE: PRT
<213> ORGANISM: Any Insect

<400> SEQUENCE: 29

Arg Val Cys Thr Cys Pro Lys Arg Asp
1 5

<210> SEQ ID NO 30
<211> LENGTH: 9
<212> TYPE: PRT
<213> ORGANISM: Any Insect

<400> SEQUENCE: 30

Lys Val Cys Thr Cys Pro Lys Arg Asp
1 5

<210> SEQ ID NO 31
<211> LENGTH: 7
<212> TYPE: PRT
<213> ORGANISM: Any Insect
<220> FEATURE:
<221> NAME/KEY: misc_feature
<222> LOCATION: (2)..(2)
<223> OTHER INFORMATION: "X" is any amino acid

<400> SEQUENCE: 31

Phe Xaa Cys Lys Asn Ser Cys
1 5

<210> SEQ ID NO 32
<211> LENGTH: 7
<212> TYPE: PRT
<213> ORGANISM: Any Insect
<220> FEATURE:
<221> NAME/KEY: misc_feature
<222> LOCATION: (2)..(2)
<223> OTHER INFORMATION: "X" is any amino acid

<400> SEQUENCE: 32

Phe Xaa Cys Gln Asn Ser Cys
1 5

-continued

<210> SEQ ID NO 33
<211> LENGTH: 393
<212> TYPE: PRT
<213> ORGANISM: Homo sapiens

<400> SEQUENCE: 33

```
Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Arg Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
```

-continued

```
    370                 375                 380

Phe Lys Thr Glu Gly Pro Asp Ser Asp
385                 390


<210> SEQ ID NO 34
<211> LENGTH: 363
<212> TYPE: PRT
<213> ORGANISM: Xenopus laevis

<400> SEQUENCE: 34

Met Glu Pro Ser Ser Glu Thr Gly Met Asp Pro Pro Leu Ser Gln Glu
1               5                   10                  15

Thr Phe Glu Asp Leu Trp Ser Leu Leu Pro Asp Pro Leu Gln Thr Val
            20                  25                  30

Thr Cys Arg Leu Asp Asn Leu Ser Glu Phe Pro Asp Tyr Pro Leu Ala
        35                  40                  45

Ala Asp Met Thr Val Leu Gln Glu Gly Leu Met Gly Asn Ala Val Pro
    50                  55                  60

Thr Val Thr Ser Cys Ala Val Pro Ser Thr Asp Asp Tyr Ala Gly Lys
65                  70                  75                  80

Tyr Gly Leu Gln Leu Asp Phe Gln Gln Asn Gly Thr Ala Lys Ser Val
                85                  90                  95

Thr Cys Thr Tyr Ser Pro Glu Leu Asn Lys Leu Phe Cys Gln Leu Ala
            100                 105                 110

Lys Thr Cys Pro Leu Leu Val Arg Val Glu Ser Pro Pro Pro Arg Gly
        115                 120                 125

Ser Ile Leu Arg Ala Thr Ala Val Tyr Lys Lys Ser Glu His Val Ala
    130                 135                 140

Glu Val Val Lys Arg Cys Pro His His Glu Arg Ser Val Glu Pro Gly
145                 150                 155                 160

Glu Asp Ala Ala Pro Pro Ser His Leu Met Arg Val Glu Gly Asn Leu
                165                 170                 175

Gln Ala Tyr Tyr Met Glu Asp Val Asn Ser Gly Arg His Ser Val Cys
            180                 185                 190

Val Pro Tyr Glu Gly Pro Gln Val Gly Thr Glu Cys Thr Thr Val Leu
        195                 200                 205

Tyr Asn Tyr Met Cys Asn Ser Ser Cys Met Gly Gly Met Asn Arg Arg
    210                 215                 220

Pro Ile Leu Thr Ile Ile Thr Leu Glu Thr Pro Gln Gly Leu Leu Leu
225                 230                 235                 240

Gly Arg Arg Cys Phe Glu Val Arg Val Cys Ala Cys Pro Gly Arg Asp
                245                 250                 255

Arg Arg Thr Glu Glu Asp Asn Tyr Thr Lys Lys Arg Gly Leu Lys Pro
            260                 265                 270

Ser Gly Lys Arg Glu Leu Ala His Pro Pro Ser Ser Glu Pro Pro Leu
        275                 280                 285

Pro Lys Lys Arg Leu Val Val Val Asp Asp Asp Glu Glu Ile Phe Thr
    290                 295                 300

Leu Arg Ile Lys Gly Arg Ser Arg Tyr Glu Met Ile Lys Lys Leu Asn
305                 310                 315                 320

Asp Ala Leu Glu Leu Gln Glu Ser Leu Asp Gln Gln Lys Val Thr Ile
                325                 330                 335

Lys Cys Arg Lys Cys Arg Asp Glu Ile Lys Pro Lys Lys Gly Lys Lys
            340                 345                 350
```

-continued

```
Leu Leu Val Lys Asp Glu Gln Pro Asp Ser Glu
        355                 360


<210> SEQ ID NO 35
<211> LENGTH: 564
<212> TYPE: PRT
<213> ORGANISM: Loligo forbesi

<400> SEQUENCE: 35

Met Ser Gln Gly Thr Ser Pro Asn Ser Gln Glu Thr Phe Asn Leu Leu
1               5                   10                  15

Trp Asp Ser Leu Glu Gln Val Thr Ala Asn Glu Tyr Thr Gln Ile His
            20                  25                  30

Glu Arg Gly Val Gly Tyr Glu Tyr His Glu Ala Glu Pro Asp Gln Thr
        35                  40                  45

Ser Leu Glu Ile Ser Ala Tyr Arg Ile Ala Gln Pro Asp Pro Tyr Gly
    50                  55                  60

Arg Ser Glu Ser Tyr Asp Leu Leu Asn Pro Ile Ile Asn Gln Ile Pro
65                  70                  75                  80

Ala Pro Met Pro Ile Ala Asp Thr Gln Asn Asn Pro Leu Val Asn His
                85                  90                  95

Cys Pro Tyr Glu Asp Met Pro Val Ser Ser Thr Pro Tyr Ser Pro His
            100                 105                 110

Asp His Val Gln Ser Pro Gln Pro Ser Val Pro Ser Asn Ile Lys Tyr
        115                 120                 125

Pro Gly Glu Tyr Val Phe Glu Met Ser Phe Ala Gln Pro Ser Lys Glu
    130                 135                 140

Thr Lys Ser Thr Thr Trp Thr Tyr Ser Glu Lys Leu Asp Lys Leu Tyr
145                 150                 155                 160

Val Arg Met Ala Thr Thr Cys Pro Val Arg Phe Lys Thr Ala Arg Pro
                165                 170                 175

Pro Pro Ser Gly Cys Gln Ile Arg Ala Met Pro Ile Tyr Met Lys Pro
            180                 185                 190

Glu His Val Gln Glu Val Val Lys Arg Cys Pro Asn His Ala Thr Ala
        195                 200                 205

Lys Glu His Asn Glu Lys His Pro Ala Pro Leu His Ile Val Arg Cys
    210                 215                 220

Glu His Lys Leu Ala Lys Tyr His Glu Asp Lys Tyr Ser Gly Arg Gln
225                 230                 235                 240

Ser Val Leu Ile Pro His Glu Met Pro Gln Ala Gly Ser Glu Trp Val
                245                 250                 255

Val Asn Leu Tyr Gln Phe Met Cys Leu Gly Ser Cys Val Gly Gly Pro
            260                 265                 270

Asn Arg Arg Pro Ile Gln Leu Val Phe Thr Leu Glu Lys Asp Asn Gln
        275                 280                 285

Val Leu Gly Arg Arg Ala Val Glu Val Arg Ile Cys Ala Cys Pro Gly
    290                 295                 300

Arg Asp Arg Lys Ala Asp Glu Lys Ala Ser Leu Val Ser Lys Pro Pro
305                 310                 315                 320

Ser Pro Lys Lys Asn Gly Phe Pro Gln Arg Ser Leu Val Leu Thr Asn
                325                 330                 335

Asp Ile Thr Lys Ile Thr Pro Lys Lys Arg Lys Ile Asp Asp Glu Cys
            340                 345                 350

Phe Thr Leu Lys Val Arg Gly Arg Glu Asn Tyr Glu Ile Leu Cys Lys
        355                 360                 365
```

-continued

```
Leu Arg Asp Ile Met Glu Leu Ala Ala Arg Ile Pro Glu Ala Glu Arg
    370                 375                 380

Leu Leu Tyr Lys Gln Glu Arg Gln Ala Pro Ile Gly Arg Leu Thr Ser
385                 390                 395                 400

Leu Pro Ser Ser Ser Ser Asn Gly Ser Gln Asp Gly Ser Arg Ser Ser
                405                 410                 415

Thr Ala Phe Ser Thr Ser Asp Ser Ser Gln Val Asn Ser Ser Gln Asn
            420                 425                 430

Asn Thr Gln Met Val Asn Gly Gln Val Pro His Glu Glu Glu Thr Pro
        435                 440                 445

Val Thr Lys Cys Glu Pro Thr Glu Asn Thr Ile Ala Gln Trp Leu Thr
    450                 455                 460

Lys Leu Gly Leu Gln Ala Tyr Ile Asp Asn Phe Gln Gln Lys Gly Leu
465                 470                 475                 480

His Asn Met Phe Gln Leu Asp Glu Phe Thr Leu Glu Asp Leu Gln Ser
                485                 490                 495

Met Arg Ile Gly Thr Gly His Arg Asn Lys Ile Trp Lys Ser Leu Leu
            500                 505                 510

Asp Tyr Arg Arg Leu Leu Ser Ser Gly Thr Glu Ser Gln Ala Leu Gln
        515                 520                 525

His Ala Ala Ser Asn Ala Ser Thr Leu Ser Val Gly Ser Gln Asn Ser
    530                 535                 540

Tyr Cys Pro Gly Phe Tyr Glu Val Thr Arg Tyr Thr Tyr Lys His Thr
545                 550                 555                 560

Ile Ser Tyr Leu
```

INSECT P53 TUMOR SUPPRESSOR GENES AND PROTEINS

REFERENCE TO RELATED APPLICATION

This application is a continuation-in-part of U.S. application Ser. No. 09/268,969, filed Mar. 16, 1999; and of U.S. application Ser. No. 60/184,373 of same title, filed Feb. 23, 2000. The entire contents of both prior applications are incorporated herein by reference.

BACKGROUND OF THE INVENTION

The p53 gene is mutated in over 50 different types of human cancers, including familial and spontaneous cancers, and is believed to be the most commonly mutated gene in human cancer (Zambetti and Levine, FASEB (1993) 7:855–865; Hollstein, et al., Nucleic Acids Res. (1994) 22:3551–3555). Greater than 90% of mutations in the p53 gene are missense mutations that alter a single amino acid that inactivates p53 function. Aberrant forms of human p53 are associated with poor prognosis, more aggressive tumors, metastasis, and survival rates of less than 5 years (Koshland, Science (1993) 262:1953).

The human p53 protein normally functions as a central integrator of signals arising from different forms of cellular stress, including DNA damage, hypoxia, nucleotide deprivation, and oncogene activation (Prives, Cell (1998) 95:5–8). In response to these signals, p53 protein levels are greatly increased with the result that the accumulated p53 activates pathways of cell cycle arrest or apoptosis depending on the nature and strength of these signals. Indeed, multiple lines of experimental evidence have pointed to a key role for p53 as a tumor suppressor (Levine, Cell (1997) 88:323–331). For example, homozygous p53 "knockout" mice are developmentally normal but exhibit nearly 100% incidence of neoplasia in the first year of life (Donehower et al., Nature (1992) 356:215–221). The biochemical mechanisms and pathways through which p53 functions in normal and cancerous cells are not fully understood, but one clearly important aspect of p53 function is its activity as a gene-specific transcriptional activator. Among the genes with known p53-response elements are several with well-characterized roles in either regulation of the cell cycle or apoptosis, including GADD45, p21/Waf1/Cip1, cyclin G, Bax, IGF-BP3, and MDM2 (Levine, Cell (1997) 88:323–331).

Human p53 is a 393 amino acid phosphoprotein which is divided structurally and functionally into distinct domains joined in the following order from N-terminus to C-terminus of the polypeptide chain: (a) a transcriptional activation domain; (b) a sequence-specific DNA-binding domain; (c) a linker domain; (d) an oligomerization domain; and (e) a basic regulatory domain. Other structural details of the p53 protein are in keeping with its function as a sequence-specific gene activator that responds to a variety of stress signals. For example, the most N-terminal domain of p53 is rich in acidic residues, consistent with structural features of other transcriptional activators (Fields and Jang, Science (1990) 249:1046–49). By contrast, the most C-terminal domain of p53 is rich in basic residues, and has the ability to bind single-stranded DNA, double-stranded DNA ends, and internal deletions loops (Jayaraman and Prives, Cell (1995) 81:1021–1029). The association of the p53 C-terminal basic regulatory domain with these forms of DNA that are generated during DNA repair may trigger conversion of p53 from a latent to an activated state capable of site-specific DNA binding to target genes (Hupp and Lane, Curr. Biol. (1994) 4: 865–875), thereby providing one mechanism to regulate p53 function in response to DNA damage. Importantly, both the N-terminal activation domain and the C-terminal basic regulatory domain of p53 are subject to numerous covalent modifications which correlate with stress-induced signals (Prives, Cell (1998) 95:5–8). For example, the N-terminal activation domain contains residues that are targets for phosphorylation by the DNA-activated protein kinase, the ATM kinase, and the cyclin activated kinase complex. The C-terminal basic regulatory domain contains residues that are targets for phosphorylation by protein kinase-C, cyclin dependent kinase, and casein kinase II, as well as residues that are targets for acetylation by PCAF and p300 acetyl transferases. p53 activity is also modulated by specific non-covalent protein-protein interactions (Ko and Prives, Genes Dev. (1996) 10: 1054–1072). Most notably, the MDM2 protein binds a short, highly conserved protein sequence motif, residues 13–29, in the N-terminal activation domain of p53 (Kussie et al., Science (1996) 274:948–953. As a result of binding p53, MDM2 both represses p53 transcriptional activity and promotes the degradation of p53.

Although several mammalian and vertebrate homologs of the tumor suppressor p53 have been described, only two invertebrate homologs have been identified to date in mollusc and squid. Few lines of evidence, however, have hinted at the existence of a p53 homolog in any other invertebrate species, such as the fruit fly Drosophila. Indeed, numerous direct attempts to isolate a Drosophila p53 gene by either cross-hybridization or PCR have failed to identify a p53-like gene in this species (Soussi et al., Oncogene (1990) 5: 945–952). However, other studies of response to DNA damage in insect cells using nucleic cross-hybridization and antibody cross-reactivity have provided suggestive evidence for existence of p53-, p21-, and MDM2-like genes (Bae et al., Exp Cell Res (1995) 375:105–106; Yakes, 1994, Ph.D. thesis, Wayne State University). Nonetheless, no isolated insect p53 genes or proteins have been reported to date.

Identification of novel p53 orthologues in model organisms such as *Drosophila melanogaster* and other insect species provides important and useful tools for genetic and molecular study and validation of these molecules as potential pharmaceutical and pesticide targets. The present invention discloses insect p53 genes and proteins from a variety of diverse insect species. In addition, Drosophila homologs of p33 and Rb genes, which are also involved in tumor suppression, are described.

SUMMARY OF THE INVENTION

It is an object of the present invention to provide insect p53 nucleic acid and protein sequences that can be used in genetic screening methods to characterize pathways that p53 may be involved in as well as other interacting genetic pathways. It is also an object of the invention to provide methods for screening compounds that interact with p53 such as those that may have utility as therapeutics.

These and other objects are provided by the present invention which concerns the identification and characterization of insect p53 genes and proteins in a variety of insect species. Isolated nucleic acid molecules are provided that comprise nucleic acid sequences encoding p53 polypeptides and derivatives thereof. Vectors and host cells comprising the p53 nucleic acid molecules are also described, as well as metazoan invertebrate organisms (e.g. insects, coelomates and pseudocoelomates) that are genetically modified to express or mis-express a p53 protein.

An important utility of the insect p53 nucleic acids and proteins is that they can be used in screening assays to identify candidate compounds which are potential therapeutics or pesticides that interact with p53 proteins. Such assays typically comprise contacting a p53 polypeptide with one or more candidate molecules, and detecting any interaction between the candidate compound and the p53 polypeptide. The assays may comprise adding the candidate molecules to cultures of cells genetically engineered to express p53 proteins, or alternatively, administering the candidate compound to a metazoan invertebrate organism genetically engineered to express p53 protein.

The genetically engineered metazoan invertebrate animals of the invention can also be used in methods for studying p53 activity, or for validating therapeutic or pesticidal strategies based on manipulation of the p53 pathway. These methods typically involve detecting the phenotype caused by the expression or mis-expression of the p53 protein. The methods may additionally comprise observing a second animal that has the same genetic modification as the first animal and, additionally has a mutation in a gene of interest. Any difference between the phenotypes of the two animals identifies the gene of interest as capable of modifying the function of the gene encoding the p53 protein.

BRIEF DESCRIPTION OF THE FIGURE

FIGS. 1A–1D show a CLUSTALW alignment of the amino acid sequences of the insect p53 proteins identified from Drosophila (Dros p53, SEQ ID NO:2), Leptinotarsa (CPB p53, SEQ ID NO:4), Tribolium (Trib p53A, SEQ ID 1) NO:6; Trib p53B, SEQ ID NO:8), and Hieliothis (Helio p53, SEQ ID NO:10), with p53 sequences previously identified in human (Human p53, SEQ ID NO:33), Xenopus (Xeno p53, SEQ ID NO:34), and squid (Squid p53, SEQ ID NO:35). Identical amino acid residues within the alignment are grouped within solid lines and similar amino acid residues are grouped within dashed lines.

DETAILED DESCRIPTION OF THE INVENTION

The use of invertebrate model organism genetics and related technologies can greatly facilitate the elucidation of biological pathways (Scangos, Nat. Biotechnol. (1997) 15:1220–1221; Margolis and Duyk, Nature Biotech. (1998) 16:311). Of particular use is the insect model organism, *Drosophila melanogaster* (hereinafter referred to generally as “Drosophila”). An extensive search for p53 nucleic acid and its encoded protein in Drosophila was conducted in an attempt to identify new and useful tools for probing the function and regulation of the p53 genes, and for use as targets in drug discovery. p53 nucleic acid has also been identified in the following additional insect species: *Leptinotarsa decemilineata* (Colorado potato beetle, hereinafter referred to as Leptinotarsa), *Tribolium castaneum* (flour beetle, hereinafter referred to as Tribolium), and *Heliothis virescens* (tobacco budworm, hereinafter referred to as Heliothis).

The newly identified insect p53 nucleic acids can be used for the generation of mutant phenotypes in animal models or in living cells that can be used to study regulation of p53, and the use of p53 as a drug or pesticide target. Due to the ability to rapidly carry out large-scale, systematic genetic screens, the use of invertebrate model organisms such as Drosophila has great utility for analyzing the expression and mis-expression of p53 protein. Thus, the invention provides a superior approach for identifying other components involved in the synthesis, activity, and regulation of p53 proteins. Systematic genetic analysis of p53 using invertebrate model organisms can lead to the identification and validation of compound targets directed to components of the p53 pathway. Model organisms or cultured cells that have been genetically engineered to express p53 can be used to screen candidate compounds for their ability to modulate p53 expression or activity, and thus are useful in the identification of new drug targets, therapeutic agents, diagnostics and prognostics useful in the treatment of disorders associated with cell cycle, DNA repair, and apoptosis. The details of the conditions used for the identification and/or isolation of insect p53 nucleic acids and proteins are described in the Examples section below. Various non-limiting embodiments of the invention, applications and uses of the insect p53 genes and proteins are discussed in the following sections. The entire contents of all references, including patent applications, cited herein are incorporated by reference in their entireties for all purposes. Additionally, the citation of a reference in the preceding background section is not an admission of prior art against the claims appended hereto.

p53 Nucleic Acids

The following nucleic acid sequences encoding insect p53 are described herein: SEQ ID NO:1, isolated from Drosophila, and referred to herein as DMp53; SEQ ID NO:3, isolated from Leptinotarsa, and referred to herein as CPBp53; SEQ ID NO:5 and SEQ ID NO:7, isolated from Tribolium, and referred to herein as TRIB-Ap53 and TRIB-Bp53, respectively; and SEQ ID NO:9, isolated from Heliothis, and referred to herein as HELIOp53. The genomic sequence of the DMp53 gene is provided in SEQ ID NO:18.

In addition to the fragments and derivatives of SEQ ID NOs:1, 3, 5, 7, 9, and 18, as described in detail below, the invention includes the reverse complements thereof. Also, the subject nucleic acid sequences, derivatives and fragments thereof may be RNA molecules comprising the nucleotide sequences of SEQ ID NOs:1, 3, 5, 7, 9, and 18 (or derivative or fragment thereof) wherein the base U (uracil) is substituted for the base T (thymine). The DNA and RNA sequences of the invention can be single- or double-stranded. Thus, the term “isolated nucleic acid sequence” or “isolated nucleic acid molecule”, as used herein, includes the reverse complement, RNA equivalent, DNA or RNA single- or double-stranded sequences, and DNA/RNA hybrids of the sequence being described, unless otherwise indicated.

Fragments of the p53 nucleic acid sequences can be used for a variety of purposes. Interfering RNA (RNAi) fragments, particularly double-stranded (ds) RNAi, can be used to generate loss-of-function phenotypes. p53 nucleic acid fragments are also useful as nucleic acid hybridization probes and replication/amplification primers. Certain “antisense” fragments, i.e. that are reverse complements of portions of the coding sequence of any of SEQ ID NO:1, 3, 5, 7, 9, or 18 have utility in inhibiting the function of p53 proteins. The fragments are of length sufficient to specifically hybridize with the corresponding SEQ ID NO:1, 3, 5, 7, 9, or 18. The fragments consist of or comprise at least 12, preferably at least 24, more preferably at least 36, and more preferably at least 96 contiguous nucleotides of any one of SEQ ID NOs:1, 3, 5, 7, 9, and 18. When the fragments are flanked by other nucleic acid sequences, the total length of the combined nucleic acid sequence is less than 15 kb, preferably less than 10 kb or less than 5 kb, more preferably less than 2 kb, and in some cases, preferably less than 500 bases. Preferred p53 nucleic acid fragments comprise regulatory elements that may reside in the 5' UTR and/or encode one or more of the following domains: an activation domain, a DNA binding domain, a linker domain, an oligomerization domain, and a basic regulatory domain. The approximate locations of these regions in SEQ ID Nos 1, 3, and 5, and in the corresponding amino acid sequences of SEQ ID Nos 2, 4, and 6, 8, are provided in Table 1.

TABLE 1

| | SEQ ID NOs | | |
|---|---|---|---|
| Insect Genus | 1/2 Drosophila | 3/4 Leptinotarsa | 5/6 Tribolium |
| 5' UTR | na 1–111 | na 1–120 | na 1–93 |
| Activation Domain | na 112–257 | na 121–300 | na 94–277 |
| | aa 1–48 | aa 1–60 | aa 1–60 |
| DNA Binding Domain | na 366–954 | na 321–936 | na 280–892 |
| | aa 85–280 | aa 67–271 | aa 62–265 |
| Linker Domain | na 999–1056 | na 937–999 | na 893–958 |
| | aa 296–314 | aa 272–292 | aa 266–287 |
| Oligomerization | na 1065–1170 | na 1000–1113 | na 959–1075 |
| Domain | aa 318–352 | aa 293–330 | aa 288–326 |
| Basic Regulatory | na 1179–1269 | na 1114–1182 | na 1076–1147 |
| Domain | aa 356–385 | aa 331–353 | aa 327–350 |

Further preferred are fragments of bases 354–495 of SEQ ID NO:7 and bases 315–414 of SEQ ID NO:9 of at least 12, preferably at least 24, more preferably at least 36, and most preferably at least 96 contiguous nucleotides.

The subject nucleic acid sequences may consist solely of any one of SEQ ID NOs:1, 3, 5, 7, 9, or 18, or fragments thereof. Alternatively, the subject nucleic acid sequences and fragments thereof may be joined to other components such as labels, peptides, agents that facilitate transport across cell membranes, hybridization-triggered cleavage agents or intercalating agents. The subject nucleic acid sequences and fragments thereof may also be joined to other nucleic acid sequences (i.e. they may comprise part of larger sequences) and are of synthetic/non-natural sequences and/or are isolated and/or are purified, i.e. unaccompanied by at least some of the material with which it is associated in its natural state. Preferably, the isolated nucleic acids constitute at least about 0.5%, and more preferably at least about 5% by weight of the total nucleic acid present in a given fraction, and are preferably recombinant, meaning that they comprise a non-natural sequence or a natural sequence joined to nucleotide (s) other than that which it is joined to on a natural chromosome.

Derivative nucleic acid sequences of p53 include sequences that hybridize to the nucleic acid sequence of SEQ ID NOs:1, 3, 5, 7, 9, or 18 under stringency conditions such that the hybridizing derivative nucleic acid is related to the subject nucleic acid by a certain degree of sequence identity. A nucleic acid molecule is "hybridizable" to another nucleic acid molecule, such as a cDNA, genomic DNA, or RNA, when a single stranded form of the nucleic acid molecule can anneal to the other nucleic acid molecule. Stringency of hybridization refers to conditions under which nucleic acids are hybridizable. The degree of stringency can be controlled by temperature, ionic strength, pH, and the presence of denaturing agents such as formamide during hybridization and washing. As used herein, the term "stringent hybridization conditions" are those normally used by one of skill in the art to establish at least about a 90% sequence identity between complementary pieces of DNA or DNA and RNA. "Moderately stringent hybridization conditions" are used to find derivatives having at least about a 70% sequence identity. Finally, "low-stringency hybridization conditions" are used to isolate derivative nucleic acid molecules that share at least about 50% sequence identity with the subject nucleic acid sequence.

The ultimate hybridization stringency reflects both the actual hybridization conditions as well as the washing conditions following the hybridization, and it is well known in the art how to vary the conditions to obtain the desired result. Conditions routinely used are set out in readily available procedure texts, (e.g., Current Protocol in Molecular Biology, Vol. 1, Chap. 2.10, John Wiley & Sons, Publishers (1994); Sambrook et at., Molecular Cloning, Cold Spring Harbor (1989)). A preferred derivative nucleic acid is capable of hybridizing to any one of SEQ ID NOs:1, 3, 5, 7, 9, or 18 under stringent hybridization conditions that comprise: prehybridization of filters containing nucleic acid for 8 hours to overnight at 65° C. in a solution comprising 6× single strength citrate (SSC) (1×SSC is 0.15 M NaCl, 0.015 M Na citrate; pH 7.0), 5×Denhardt's solution, 0.05% sodium pyrophosphate and 100 μg/ml herring sperm DNA; hybridization for 18–20 hours at 65° C. in a solution containing 6×SSC, 1×Denhardt's solution, 100 μg/ml yeast tRNA and 0.05% sodium pyrophosphate; and washing of filters at 65° C. for 1 h in a solution containing 0.2×SSC and 0.1% SDS (sodium dodecyl sulfate).

Derivative nucleic acid sequences that have at least about 70% sequence identity with any one of SEQ ID NOs:1, 3, 5, 7, 9, and 18 are capable of hybridizing to any one of SEQ ID NO:1, 3, 5, 7, 9, and 18 under moderately stringent conditions that comprise: pretreatment of filters containing nucleic acid for 6 h at 40° C. in a solution containing 35% formamide, 5×SSC, 50 mM Tris-HCl (pH 7.5), 5 mM EDTA. 0.1% PVP, 0.1% Ficoll, 1% BSA, and 500 μg/ml denatured salmon sperm DNA; hybridization for 18–20 h at 40° C. in a solution containing 35% formamide, 5×SSC, 50 mM Tris-HCl (pH 7.5), 5 mM EDTA, 0.02% PVP, 0.02% Ficoll, 0.2% BSA, 100 μg/ml salmon sperm DNA, and 10% (wt/vol) dextran sulfate; followed by washing twice for 1 hour at 55° C. in a solution containing 2×SSC and 0.1% SDS.

Other preferred derivative nucleic acid sequences are capable of hybridizing to any one of SEQ ID NOs:1, 3, 5, 7, 9, and 18 under low stringency conditions that comprise: incubation for 8 hours to overnight at 37° C. in a solution comprising 20% formamide, 5×SSC, 50 mM sodium phosphate (pH 7.6), 5×Denhardt's solution, 10% dextran sulfate, and 20 μg/ml denatured sheared salmon sperm DNA; hybridization in the same buffer for 18 to 20 hours; and washing of filters in 1×SSC at about 37° C. for 1 hour.

As used herein, "percent (%) nucleic acid sequence identity" with respect to a subject sequence, or a specified portion of a subject sequence, is defined as the percentage of nucleotides in the candidate derivative nucleic acid sequence identical with the nucleotides in the subject sequence (or specified portion thereof), after aligning the sequences and introducing gaps, if necessary to achieve the maximum percent sequence identity, as generated by the program WU-BLAST-2.0a19 (Altschul et al., J. Mol. Biol. (1997) 215:403–410; hereinafter referred to generally as "BLAST") with all the search parameters set to default values. The HSP S and HSP S2 parameters are dynamic values and are established by the program itself depending upon the composition of the particular sequence and composition of the particular database against which the sequence of interest is being searched. A percent (%) nucleic acid sequence identity value is determined by the number of matching identical nucleotides divided by the sequence length for which the percent identity is being reported.

Derivative p53 nucleic acid sequences usually have at least 50% sequence identity, preferably at least 60%, 70%, or 80% sequence identity, more preferably at least 85% sequence identity, still more preferably at least 90% sequence identity, and most preferably at least 95% sequence identity with any one of SEQ ID NOs:1, 3, 5, 7, 9, or 18, or domain-encoding regions thereof.

In one preferred embodiment, the derivative nucleic acid encodes a polypeptide comprising a p53 amino acid sequence of any one of SEQ ID NOs:2, 4, 6, 8, or 10, or a fragment or derivative thereof as described further below under the subheading "p53 proteins". A derivative p53 nucleic acid sequence, or fragment thereof, may comprise 100% sequence identity with any one of SEQ ID NOs:1, 3, 5, 7, 9, or 18, but be a derivative thereof in the sense that it has one or more modifications at the base or sugar moiety, or phosphate backbone. Examples of modifications are well known in the art (Bailey, Ullmann's Encyclopedia of Industrial Chemistry (1998), 6th ed. Wiley and Sons). Such derivatives may be used to provide modified stability or any other desired property.

Another type of derivative of the subject nucleic acid sequences includes corresponding humanized sequences. A humanized nucleic acid sequence is one in which one or more codons has been substituted with a codon that is more commonly used in human genes. Preferably, a sufficient number of codons have been substituted such that a higher level expression is achieved in mammalian cells than what would otherwise be achieved without the substitutions. The following list shows, for each amino acid, the calculated codon frequency (number in parentheses) in humans genes for 1000 codons (Wada et al., Nucleic Acids Research (1990) 18(Suppl.):2367–2411):

Human codon frequency per 1000 codons:

ARG: CGA (5.4), CGC (11.3), CGG (10.4), CGU (4.7), AGA (9.9), AGG (11.1)

LEU: CUA (6.2), CUC (19.9), CUG (42.5), CUU (10.7), UUA (5.3), UUG (11.0)

SER: UCA (9.3), UCC (17.7), UCG (4.2), UCU (13.2), AGC (18.7), AGU (9.4)

THR: ACA (14.4), ACC (23.0), ACG (6.7), ACU (12.7)

PRO: CCA (14.6), CCC (20.0), CCG (6.6), CCU (15.5)

ALA: GCA (14.0), GCC (29.1), GCG (7.2), GCU (19.6)

GLY: GGA (17.1), GGC (25.4), GGG (17.3), GGU (11.2)

VAL: GUA (5.9), GUC (16.3), GUG (30.9), GUU (10.4)

LYS: AAA (22.2), AAG (34.9)

ASN: AAC (22.6), AAU (16.6)

GLN: CAA (11.1), CAG (33.6)

HIS: CAC (14.2), CAU (9.3)

GLU: GAA (26.8), GAG (41.4)

ASP: GAC (29.0), GAU (21.7)

TYR: UAC (18.8), UAU (12.5)

CYS: UGC (14.5), UGU (9.9)

PHE: UUU (22.6), UUC (15.8)

ILE: AUA (5.8), AUC (24.3), AUU (14.9)

MET: AUG (22.3)

TRP: UGG (13.8)

TER: UAA (0.7), AUG (0.5), UGA (1.2)

Thus, a p53 nucleic acid sequence in which the glutamic acid codon, GAA has been replaced with the codon GAG, which is more commonly used in human genes, is an example of a humanized p53 nucleic acid sequence. A detailed discussion of the humanization of nucleic acid sequences is provided in U.S. Pat. No. 5,874,304 to Zolotukhin et al. Similarly, other nucleic acid derivatives can be generated with codon usage optimized for expression in other organisms, such as yeasts, bacteria, and plants, where it is desired to engineer the expression of p53 proteins by using specific codons chosen according to the preferred codons used in highly expressed genes in each organism. More specific embodiments of preferred p53 proteins, fragments, and derivatives are discussed further below in connection under the subheading "p53 proteins".

Nucleic acid encoding the amino acid sequence of any of SEQ ID NOs:2, 4, 6, 8, and 10, or fragment or derivative thereof, may be obtained from an appropriate cDNA library prepared from any eukaryotic species that encodes p53 proteins such as vertebrates, preferably mammalian (e.g. primate, porcine, bovine, feline, equine, and canine species, etc.) and invertebrates, such as arthropods, particularly insects species (preferably Drosophila, Tribolium, Leptinotarsa, and Heliothis), acarids, crustacea, molluscs, nematodes, and other worms. An expression library can be constructed using known methods. For example, mRNA can be isolated to make cDNA which is ligated into a suitable expression vector for expression in a host cell into which it is introduced. Various screening assays can then be used to select for the gene or gene product (e.g. oligonucleotides of at least about 20 to 80 bases designed to identify the gene of interest, or labeled antibodies that specifically bind to the gene product). The gene and/or gene product can then be recovered from the host cell using known techniques.

Polymerase chain reaction (PCR) can also be used to isolate nucleic acids of the p53 genes where oligonucleotide primers representing fragmentary sequences of interest amplify RNA or DNA sequences from a source such as a genomic or cDNA library (as described by Sambrook et al., supra). Additionally, degenerate primers for amplifying homologs from any species of interest may be used. Once a PCR product of appropriate size and sequence is obtained, it may be cloned and sequenced by standard techniques, and utilized as a probe to isolate a complete cDNA or genomic clone.

Fragmentary sequences of p53 nucleic acids and derivatives may be synthesized by known methods. For example, oligonucleotides may be synthesized using an automated DNA synthesizer available from commercial suppliers (e.g. Biosearch, Novato, Calif.; Perkin-Elmer Applied Biosystems, Foster City, Calif.). Antisense RNA sequences can be produced intracellularly by transcription from an exogenous sequence, e.g. from vectors that contain antisense p53 nucleic acid sequences. Newly generated sequences may be identified and isolated using standard methods.

An isolated p53 nucleic acid sequence can be inserted into any appropriate cloning vector, for example bacteriophages such as lambda derivatives, or plasmids such as PBR322, pUC plasmid derivatives and the Bluescript vector (Stratagene, San Diego, Calif.). Recombinant molecules can be introduced into host cells via transformation, transfection, infection, electroporation, etc., or into a transgenic animal such as a fly. The transformed cells can be cultured to generate large quantities of the p53 nucleic acid. Suitable methods for isolating and producing the subject nucleic acid sequences are well-known in the art (Sambrook et al., supra; DNA Cloning: A Practical Approach, Vol. 1, 2, 3, 4, (1995) Glover, ed., MRL Press, Ltd., Oxford, U.K.).

The nucleotide sequence encoding a p53 protein or fragment or derivative thereof, can be inserted into any appropriate expression vector for the transcription and translation of the inserted protein-coding sequence. Alternatively, the necessary transcriptional and translational signals can be supplied by the native p53 gene and/or its flanking regions.

A variety of host-vector systems may be utilized to express the protein-coding sequence such as mammalian cell systems infected with virus (e.g. vaccinia virus, adenovirus, etc.); insect cell systems infected with virus (e.g. baculovirus); microorganisms such as yeast containing yeast vectors, or bacteria transformed with bacteriophage, DNA, plasmid DNA, or cosmid DNA. If expression in plants is desired, a variety of transformation constructs, vectors and methods are known in the art (see U.S. Pat. No. 6,002,068 for review). Expression of a p53 protein may be controlled by a suitable promoter/enhancer element. In addition, a host cell stain may be selected which modulates the expression of the inserted sequences, or modifies and processes the gene product in the specific fashion desired.

To detect expression of the p53 gene product, the expression vector can comprise a promoter operably linked to a p53 gene nucleic acid, one or more origins of replication, and, one or more selectable markers (e.g. thymidine kinase activity, resistance to antibiotics, etc.). Alternatively, recombinant expression vectors can be identified by assaying for the expression of the p53 gene product based on the physical or functional properties of the p53 protein in in vitro assay systems (e.g. immunoassays or cell cycle assays). The p53 protein, fragment, or derivative may be optionally expressed as a fusion, or chimeric protein product as described above.

Once a recombinant that expresses the p53 gene sequence is identified, the gene product can be isolated and purified using standard methods (e.g. ion exchange, affinity, and gel exclusion chromatography; centrifugation; differential solubility; electrophoresis). The amino acid sequence of the protein can be deduced from the nucleotide sequence of the chimeric gene contained in the recombinant and can thus be synthesized by standard chemical methods (Hunkapiller et al., Nature (1984) 310:105–111). Alternatively, native p53 proteins can be purified from natural sources, by standard methods (e.g. immunoaffinity purification).

p33 and Rb Nucleic Acids

The invention also provides nucleic acid sequences for Drosophila p33 (SEQ ID NO:19), and Rb (SEQ ID NO:21) tumor suppressors. Derivatives and fragments of these sequences can be prepared as described above for the p53 sequences. Preferred fragments and derivatives comprise the same number of contiguous nucleotides or same degrees of percent identity as described above for p53 nucleic acid sequences. The disclosure below regarding various uses of p53 tumor suppressor nucleic acids and proteins (e.g. transgenic animals, tumor suppressor assays, etc.) also applies to the p33 and Rb tumor suppressor sequences disclosed herein.

p53 Proteins

The CLUSTALW program (Thompson, et al., Nucleic Acids Research (1994) 22(22):4673–4680) was used to align the insect p53 proteins described herein with p53 proteins from human (Zakut-Houri et al., EMBO J. (1985) 4:1251–1255; GenBank gi:129369), Xenopus (Sousi et al., Oncogene (1987) 1:71–78; GenBank gi:129374), and squid (GenBank gi:1244762). The alignment generated is shown in FIG. 1 and reveals a number of features in the insect p53 proteins that are characteristic of the previously-identified p53 proteins. With respect to general areas of structural similarity, the DMp53, CPBp53, and TRIB-Ap53 proteins can be roughly divided into three regions: a central region which exhibits a high degree of sequence homology with other known p53 family proteins and which roughly corresponds to the DNA binding domain of this protein family (Cho et al., Science (1994)265:346–355), and flanking N-terminal and C-terminal regions which exhibit significantly less homology but which correspond in overall size to other p53 family proteins. The fragmentary polypeptide sequences encoded by the TRIB-Bp53 and HELIOp53 cDNAs are shown by the multiple sequence alignment to be derived from the central region—the conserved DNA-binding domain. Significantly, the protein sequence alignment allowed the assignment of the domains in the DMp53, CPBp53, and TRIB-A p53 proteins listed in Table 1 above, based on sequence homology with previously characterized domains of human p53 (Sousi and May, J. Mol Biol (1996) 260:623–637; Levine, supra; Prives, Cell (1998) 95:5–8).

Importantly, the most conserved central regions of the DMp53, CPBp53, and TRIB-A p53 proteins correspond almost precisely to the known functional boundaries of the DNA binding domain of human p53, indicating that these proteins are likely to exhibit similar DNA binding properties to those of human p53. A detailed examination of the conserved residues in this domain further emphasizes the likely structural and functional similarities between human p53 and the insect p53 proteins. First, residues of the human p53 known to be involved in direct DNA contacts (K120, S241, R248, R273, C277, and R280) correspond to identical or similar residues in the DMp53 protein (K113, S230, R234, K259, C263, and R266), and identical residues in the CPBp53 protein (K92, S216, R224, R249, C253, and R256), and the TRIB-Ap53 protein (K88, S213, R220, R245, C249, and R252). Also, with regard to the overall folding of this domain, it was notable that four key residues that coordinate the zinc ligand in the DNA binding domain of human p53 (C176, H179, C238, and C242) are precisely conserved in the DMp53 protein (C156, H159, C227, and C231), the CPBp53 protein (C147, H150, C213, and C217), and the TRIB-A p53 protein (C144, H147, C210, C214). Furthermore, it was striking that the mutational hot spots in human p53 most frequently altered in cancer (R175, G245, R248, R249, R273, and R282), are either identical or conserved amino acid residues in the corresponding positions of the DMp53 protein (R155, G233, R234, K235, K259, and R268), the CPBp53 protein (R146, G221, R224, R225, R249, and K258), and the TRIB-Ap53 protein (R143, G217, R220, R221, R245, and K254).

Interestingly, the insect p53s also have distinct differences from the Human, Xenopus, and squid p53s. Specifically, insect p53s contain a unique amino acid sequence within the DNA recognition domain that has the following sequence: (R or K)(I or V)C(S or T)CPKRD. Specifically, amino acid residues 259 to 267 of DMp53 have the sequence: KICTCPKRD; residues 249 to 257 of CPBp53 have the sequence: RICSCPKRD; and residues 245–253 of TRIB-Ap53 have the sequence: RVCSCPKRD. This is in distinct contrast to the Human, Xenopus, and squid p53s which have the following corresponding sequence: R(I or V)CACPGRD.

Another region of insect p53s that distinctly differs from previously identified p53s lies in the zinc coordination region of the DNA binding domain. The following sequence is conserved within the insect p53s: FXC(K or Q)NSC (where X=any amino acid). Specifically, residues 225–231 of DMp53 have the sequence: FVCQNSC; residues 211–217 of CPBp53 and residues 208–214 of TRIB-Ap53 have the sequence FVCKNSC; and the corresponding residues in Helio-p53, as shown in FIG. 1, have the sequence: FSCKNSC. In contrast, the corresponding sequence in Human and Xenopus p53 is YMCNSSC, and in squid it is FMCLGSC.

The high degree of structural homology in the presumptive DNA binding domain of the insect p53 proteins has important implications for engineering derivative (e.g.

mutant) forms of these p53 genes for tests of function in vitro and in vivo, and for genetic dissection or manipulation of the p53 pathway in transgenic insects or insect cell lines. Dominant negative forms of human p53 have been generated by creating altered proteins which have a defective DNA binding domain, but which retain a functional oligomerization domain (Brachman et al., Proc Natl Acad Sci USA (1996) 93:4091–4095). Such dominant negative mutant forms are extremely useful for determining the effects of loss-of-function of p53 in assays of interest. Thus, mutations in highly conserved positions within the DNA binding domain of the insect p53 proteins, which correspond to residues known to be important for the structure and function of human p53 (such as R175H, H179N, and R280T of human p53), are likely to result in dominant negative forms of insect p53 proteins. For example, specific mutations in the DMp53 protein to create dominant negative mutant forms of the protein include R155H, H159N, and R266T and for the TRIB-A p53 protein include R143H, H147N, and R252T.

Although other domains of the insect p53 proteins, aside from the DNA binding domain, exhibit significantly less homology compared to the known p53 family proteins, the sequence alignment provides important information about their structure and potential function. Notably, just as in the human p53 protein, the C-terminal 20–25 amino acids of the protein comprise a putative region that extends beyond the oligomerization domain, suggesting an analogous function for this region of the insect p53 proteins in regulating activity of the protein. Since deletion of the C-terminal regulatory domain in human p53 has been shown to generate constitutively activated forms of the protein (Hupp and Lane, Curr. Biol. (1994) 4:865–875), it is expected that removal of most or all of the corresponding regulatory domain from the insect p53 proteins will generate an activated protein form. Thus preferred truncated forms of the insect p53 proteins lack at least 10 C-terminal amino acids, more preferably at least 15 amino acids, and most preferably at least C-terminal amino acids. For example, a preferred truncated version of DMp53 comprises amino acid residues 1–376, more preferably residues 1–371, and most preferably residues 1–366 of SEQ ID NO:2. Such constitutively activated mutant forms of the protein are very useful for tests of protein function using in vivo and in vitro assays, as well as for genetic analysis.

The oligomerization domain of the insect p53 proteins exhibit very limited skeletal sequence homology with other p53 family proteins, although the length of this region is similar to that of other p53 family proteins. The extent of sequence divergence in this region of the insect proteins raises the possibility that the insect p53 protein may be unable to form hetero-oligomers with p53 proteins from vertebrates or squid. And, although the linker domain located between the DNA binding and oligomerization domains also exhibits relatively little sequence conservation, this region of any of the DMp53, CPBp53, and TRIB-A p53 proteins contains predicted nuclear localization signals similar to those identified in human p53 (Shaulsky et al., Mol Cell Biol (1990) 10:6565–6577).

The activation domain at the N-terminus of the insect p53 proteins also exhibits little sequence identity with other p53 family proteins, although the size of this region is roughly the same as that of human p53. Nonetheless, an important feature of this domain is the relative concentration of acidic residues in the insect p53 proteins. Consequently, it is likely that this N-terminal domain of any of the DMp53, CPBp53, and TRIB-Ap53 proteins will similarly exert the functional activity of a transcriptional activation domain to that of the human p53 domain (Thut et al., Science (1995) 267:100–104). Interestingly, the DMp53, CPBp53 and TRIB-A p53 proteins do not appear to possess a highly conserved sequence motif, FxxLWxL, found at the N-terminus of vertebrate and squid p53 family proteins. In the human p53 gene, these conserved residues in this motif participate in a specific interaction between human p53 proteins and mdm2 (Kussie et al., Science (1996) 274:948–953).

It is important to note that, although there is no sequence similarity between the insect p53s and other p53 family members in the C- and N-termini, these regions of p53 contain secondary structure characteristic of p53-related proteins. For example, the human p53 binds DNA as a homo-tetrameter and self-association is mediated by a β-sheet and amphipathic α-helix located in the C-terminus of the protein. A similar β-sheet-turn-α-helix is predicted in the C-terminus of DMp53. Further, the N-terminus of the human p53 is a region that includes a transactivation domain and residues critical for binding to the mdm-2 protein. The N-terminus of the DMp53 also include acidic amino acids and likely functions as a transactivation domain.

p53 proteins of the invention comprise or consist of an amino acid sequence of any one of SEQ ID NOs:2, 4, 6, 8, and 10 or fragments or derivatives thereof. Compositions comprising these proteins may consist essentially of the p53 protein, fragments, or derivatives, or may comprise additional components (e.g. pharmaceutically acceptable carriers or excipients, culture media, etc.). p53 protein derivatives typically share a certain degree of sequence identity or sequence similarity with any one of SEQ ID NOs:2, 4, 6, 8, and 10 or fragments thereof. As used herein, "percent (%) amino acid sequence identity" with respect to a subject sequence, or a specified portion of a subject sequence, is defined as the percentage of amino acids in the candidate derivative amino acid sequence identical with the amino acid in the subject sequence (or specified portion thereof), after aligning the sequences and introducing gaps, if necessary to achieve the maximum percent sequence identity, as generated by BLAST (Altschul et al., supra) using the same parameters discussed above for derivative nucleic acid sequences. A % amino acid sequence identity value is determined by the number of matching identical amino acids divided by the sequence length for which the percent identity is being reported. "Percent (%) amino acid sequence similarity" is determined by doing the same calculation as for determining % amino acid sequence identity, but including conservative amino acid substitutions in addition to identical amino acids in the computation. A conservative amino acid substitution is one in which an amino acid is substituted for another amino acid having similar properties such that the folding or activity of the protein is not significantly affected. Aromatic amino acids that can be substituted for each other are phenylalanine, tryptophan, and tyrosine; interchangeable hydrophobic amino acids are leucine, isoleucine, methionine, and valine; interchangeable polar amino acids are glutamine and asparagine; interchangeable basic amino acids arginine, lysine and histidine; interchangeable acidic amino acids aspartic acid and glutamic acid; and interchangeable small amino acids alanine, serine, cystine, threonine, and glycine.

In one preferred embodiment, a p53 protein derivative shares at least 50% sequence identity or similarity, preferably at least 60%, 70%, or 80% sequence identity or similarity, more preferably at least 85% sequence similarity or identity, still more preferably at least 90% sequence similarity, or identity, and most preferably at least 95% sequence identity or similarity with a contiguous stretch of at least 10 amino acids, preferably at least 25 amino acids, more preferably at least 40 amino acids, still more preferably at least 50 amino acids, more preferably at least 100 amino acids, and in some cases, the entire length of any one of SEQ ID NOs:2, 4, 6, 8, or 10. Further preferred derivatives share these % sequence identities with the domains of SEQ ID NOs 2, 4 and 6 listed in Table I above. Additional preferred derivatives comprise a sequence that shares 100% similarity with any contiguous stretch of at least 10 amino acids, preferably at least 12, more preferably at least 15, and most preferably at least 20 amino acids of any of SEQ ID NOs 2, 4, 6, 8, and 10, and preferably functional domains thereof. Further preferred fragments comprise at least 7 contiguous amino acids, preferably at least 9, more preferably at least 12, and most preferably at least 17 contiguous amino acids of any of SEQ ID NOs 2,4, 6, 8, and 10, and preferably functional domains thereof.

Other preferred p53 polypeptides, fragments or derivatives consist of or comprise a sequence selected from the group consisting of RICSCPKRD (SEQ ID NO:23), KICSCPKRD (SEQ ID NO:24), RVCSCPKRD (SEQ ID NO:25), KVCSCPKRD (SEQ ID NO:26), RICTCPKRD (SEQ ID NO:27), KICTCPKRD (SEQ ID NO:28), RVCTCPKRD (SEQ ID NO:29), and KVCTCPKRD (SEQ ID NO:30) (i.e. sequences of the formula: (R or K)(I or V)C(S or T)CPKRD). Additional preferred p53 polypeptides, fragments or derivatives, consist of or comprise a sequence selected from the group consisting of FXCKNSC (SEQ ID NO:31) and FXCQNSC (SEQ ID NO:32), where X=any amino acid.

The fragment or derivative of any of the p53 proteins is preferably "functionally active" meaning that the p53 protein derivative or fragment exhibits one or more functional activities associated with a full-length, wild-type p53 protein comprising the amino acid sequence of any of SEQ ID NOs:2, 4, 6, 8, or 10. As one example, a fragment or derivative may have antigenicity such that it can be used in immunoassays, for immunization, for inhibition of p53 activity, etc. as discussed further below regarding generation of antibodies to p53 proteins. Preferably, a functionally active p53 fragment or derivative is one that displays one or more biological activies associated with p53 proteins such as regulation of the cell cycle, or transcription control. The functional activity of p53 proteins, derivatives and fragments can be assayed by various methods known to one skilled in the art (Current Protocols in Protein Science (1998) Coligan et al., eds., John Wiley & Sons, Inc., Somerset, N.J.). Example 12 below describes a variety of suitable assays for assessing p53 function.

P 53 derivatives can be produced by various methods known in the art. The manipulations which result in their production can occur at the gene or protein level. For example, a cloned p53 gene sequence can be cleaved at appropriate sites with restriction endonuclease(s) (Wells et al., Philos. Trans. R. Soc. London SerA (1986) 317:415), followed by further enzymatic modification if desired, isolated, and ligated in vitro, and expressed to produce the desired derivative. Alternatively, a p53 gene can be mutated in vitro or in vivo, to create, and/or destroy translation, initiation, and/or termination sequences, or to create variations in coding regions and/or to form new restriction endonuclease sites or destroy preexisting ones, to facilitate further in vitro modification. A variety of mutagenesis techniques are known in the art such as chemical mutagenesis, in vitro site-directed mutagenesis (Carter et al., Nucl. Acids Res. (1986) 13:4331), use of TAB™ linkers (available from Pharmacia and Upjohn, Kalamazoo, Mich.), etc.

At the protein level, manipulations include post translational modification, e.g. glycosylation, acetylation phosphorylation, amidation, derivatization by known protecting/blocking groups, proteolytic cleavage, linkage to an antibody molecule or other cellular ligand, etc. Any of numerous chemical modifications may be carried out by known technique (e.g. specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc.). Derivative proteins can also be chemically synthesized by use of a peptide synthesizer, for example to introduce nonclassical amino, acids or chemical amino acid analogs as substitutions or additions into the p53 protein sequence.

Chimeric or fusion proteins can be made comprising a p53 protein or fragment thereof (preferably comprising one or more structural or functional domains of the p53 protein) joined at its N- or C-terminus via a peptide bond to an amino acid sequence of a different protein. A chimeric product can be made by ligating the appropriate nucleic acid sequences encoding the desired amino acid sequences to each other in the proper coding frame using standard methods and expressing the chimeric product. A chimeric product may also be made by protein synthetic techniques, e.g. by use of a peptide synthesizer.

p33 and Rb Proteins

The invention also provides amino acid sequences for Drosophila p33 (SEQ ID NO:20), and Rb (SEQ ID NO:22) tumor suppressors. Derivatives and fragments of these sequences can be prepared as described above for the p53 protein sequences. Preferred fragments and derivatives comprise the same number of contiguous amino acids or same degrees of percent identity or similarity as described above for p53 amino acid sequences.

p53 Gene Regulatory Elements p53 gene regulatory DNA elements, such as enhancers or promoters that reside within the 5' UTRs of SEQ ID NOs 1, 3, and 5, as shown in Table I above, or within nucleotides 1–1225 of SEQ ID NO:18, can be used to identify tissues, cells, genes and factors that specifically control p53 protein production. Preferably at least 20, more preferably at least 25, and most preferably at least 50 contiguous nucleotides within the 5' UTRs are used. Analyzing components that are specific to p53 protein function can lead to an understanding of how to manipulate these regulatory processes, for either pesticide or therapeutic applications, as well as an understanding of how to diagnose dysfunction in these processes.

Gene fusions with the p53 regulatory elements can be made. For compact genes that have relatively few and small intervening sequences, such as those described herein for Drosophila, it is typically the case that the regulatory elements that control spatial and temporal expression patterns are found in the DNA immediately upstream of the coding region, extending to the nearest neighboring gene. Regulatory regions can be used to construct gene fusions where the regulatory DNAs are operably fused to a coding region for a reporter protein whose expression is easily detected, and these constructs are introduced as transgenes into the animal of choice. An entire regulatory DNA region can be used; or the regulatory region can be divided into smaller segments to identify sub-elements that might be specific for controlling expression a given cell type or stage of development. One suitable method to decipher regions containing regulatory sequences is by an in vitro CAT assay (Mercer, Crit. Rev. Euk. Gene Exp. (1992) 2:251–263; Sambrook et al., supra; and Gorman et al., Mol. Cell. Biol. (1992) 2:1044–1051). Additional reporter proteins that can be used for construction of these gene fusions include *E. coli* beta-galactosidase and green fluorescent protein (GFP). These can be detected readily in situ, and thus are useful for histological studies and can be used to sort cells that express p53 proteins (O'Kane and Gehring PNAS (1987) 84(24):9123–9127; Chalfie et al., Science (1994) 263:802–805; and Cumberledge and Krasnow (1994) Methods in Cell Biology 44:143–159). Recombinase proteins, such as FLP or cre, can be used in controlling gene expression through site-specific recombination (Golic and Lindquist (1989) Cell 59(3):499–509; White et al., Science (1996) 271:805–807). Toxic proteins such as the reaper and hid cell death proteins, are useful to specifically ablate cells that normally express p53 proteins in order to assess the physiological function of the cells (Kingston, In Current Protocols in Molecular Biology (1998) Ausubel et al., John Wiley & Sons, Inc. sections 12.0.3–12.10) or any other protein where it is desired to examine the function this particular protein specifically in cells that synthesize p53 proteins.

Alternatively, a binary reporter system can be used, similar to that described further below, where the p53 regulatory element is operably fused to the coding region of an exogenous transcriptional activator protein, such as the GAL4 or tTA activators described below, to create a p53 regulatory element "driver gene". For the other half of the binary system the exogenous activator controls a separate "target gene" containing a coding region of a reporter protein operably fused to a cognate regulatory element for the exogenous activator protein, such as $UAS_G$ or a tTA-response element, respectively. An advantage of a binary system is that a single driver gene construct can be used to activate transcription from preconstructed target genes encoding different reporter proteins, each with its own uses as delineated above.

p53 regulatory element-reporter gene fusions are also useful for tests of genetic interactions, where the objective is to identify those genes that have a specific role in controlling the expression of p53 genes, or promoting the growth and differentiation of the tissues that expresses the p53 protein. p53 gene regulatory DNA elements are also useful in protein-DNA binding assays to identify gene regulatory proteins that control the expression of p53 genes. The gene regulatory proteins can be detected using a variety of methods that probe specific protein-DNA interactions well known to those skilled in the art (Kingston, supra) including in vivo footprinting assays based on protection of DNA sequences from chemical and enzymatic modification within living or permeabilized cells; and in vitro footprintinig assays based on protection of DNA sequences from chemical or enzymatic modification using protein extracts, nitrocellulose filter-binding assays and gel electrophoresis mobility shift assays using radioactively labeled regulatory DNA elements mixed with protein extracts. Candidate p53 gene regulatory proteins can be purified using a combination of conventional and DNA-affinity purification techniques. Molecular cloning strategies can also be used to identify proteins that specifically bind p53 gene regulatory DNA elements. For example, a Drosophila cDNA library in an expression vector, can be screened for cDNAs that encode p53 gene regulatory element DNA-binding activity. Similarly, the yeast "one-hybrid" system can be used (Li and Herskowitz, Science (1993) 262:1870–1874; Luo et al., Biotechniques (1996) 20(4):564–568; Vidal et al., PNAS (1996) 93(19):10315–10329).

Assays for Tumor Suppressor Genes

The p53 tumor suppressor gene encodes a transcription factor implicated in regulation of cell proliferation, control of the cell cycle, and induction of apoptosis. Various experimental methods may be used to assess the role of the insect p53 genes in each of these areas.

Transcription Activity Assays

Due to its acidic region, wild type p53 binds both specifically and non-specifically to DNA in order to mediate its function (Zambetti and Levine, supra). Transcriptional regulation by the p53 protein or its fragments may be examined by any method known in the art. An electrophoretic mobility shift assay can be used to characterize DNA sequences to which p53 binds, and thus can assist in the identification of genes regulated by p53. Briefly, cells are grown and transfected with various amounts of wild type or mutated transcription factor of interest (in this case, p53), harvested 48 hr after transfection; and lysed to prepare nuclear extracts. Preparations of Drosophila nuclear extracts for use in mobility shift assays may be done as described in Dignam et al., Nucleic Acids Res. (1983) 11:1475–1489. Additionally, complementary, single-stranded oligonucleotides corresponding to target sequences for binding are synthesized and self-annealed to a final concentration of 10–15 ng/$\mu$l. Double stranded DNA is verified by gel electrophoretic analysis (e.g., on a 7% polyacrylarmide gel, by methods known in the art), and end-labeled with 20 $\mu$Ci [32P] $\gamma$-dATP. The nuclear extracts are mixed with the double stranded target sequences under conditions conducive for binding and the results are analyzed by polyacrylamide gel electrophoresis.

Another suitable method to determine DNA sequences to which p53 binds is by DNA footprinting (Schmitz et al., Nucleic Acids Research (1978) 5:3157–3170).

Apoptosis Assays

A variety of methods may be used to examine apoptosis. One method is the terminal deoxynucleotidyl transferase-mediated digoxigenin-11-dUTP nick end labeling (TUNEL) assay which measures the nuclear DNA fragmentation characteristic of apoptosis (Lazebnik et al., Nature (1994) 371:346–347; White et al., Science (1994) 264:677–683). Additionally, commercial kits can be used for detection of apoptosis (ApoAlert® available from Clontech (Palo Alto, Calif.).

Apoptosis may also be assayed by a variety of staining methods. Acridine orange can be used to detect apoptosis in cultured cells (Lucas et al., Blood (1998) 15:4730–41) and in intact Drosophila tissues, which can also be stained with Nile Blue (Abrams et al., Development (1993) 117:29–43). Another assay that can be used to detect DNA laddering employs ethidium bromide staining and electophoresis of DNA on an agarose gel (Civielli et al., Int. J. Cancer (1995) 27:673–679; Young, J. Biol. Chem. (1998) 273:25198–25202).

Proliferation and Cell Cycle Assays

Proliferating cells may be identified by bromodeoxyuridine (BRDU) incorporation into cells undergoing DNA synthesis and detection by an anti-BRDU antibody (Hoshino et al., Int. J. Cancer (1986),38:369; Campana et al., J. Immunol. Meth. (1988) 107:79). This assay can be used to reproducibly identify S-phase cells in Drosophila embryos (Edgar and O'Farrell, Cell (1990) 62:469–480) and imaginal discs (Secombe et al., Genetics (1998) 149:1867–1882). S-phase DNA syntheses can also be quantified by measuring [$^3$H]-thymidine incorporation using a scintillation counter (Chen, Oncogene (1996) 13:1395–403; Jeoung, J. Biol. Chem. (1995) 270:18367–73). Cell proliferation may be measured by counting samples of a cell population over time, for example using a hemacytometer and Trypan-blue staining.

The DNA content and/or mitotic index of the cells may be measured based on the DNA ploidy value of the cell using a variety of methods known in the art such as a propidum iodide assay (Turner et al., Prostate (1998) 34:175–81) or Feulgen staining using a computerized microdensitometry staining system (Bacus, Am. J. Pathol.(1989) 135:783–92).

The effect of p53 overexpression or loss-of-function on Drosophila cell proliferation can be assayed in vivo using an assay in which clones of cells with altered gene expression are generated in the developing wing disc of Drosophila (Neufeld et al., Cell (1998) 93:1183–93). The clones coexpress GFP, which allows the size and DNA content of the mutant and wild-type cells from dissociated discs to be compared by FACS analysis.

Tumor Formation and Transformation Assays

A variety of in vivo and in vitro tumor formation assays are known in the art that can be used to assay p53 function. Such assays can be used to detect foci formation (Beenken, J. Surg. Res. (1992) 52:401–5), in vitro transformation (Ginsberg, Oncogene. (1991) 6:669–72), tumor formation in nude mice (Endlich, Int. J. Radiat. Biol. (1993) 64:715–26), tumor formation in Drosophila (Tao et al., Nat. Genet. (1999) 21:177–181), and anchorage-independent growth in soft agar (Endlich, supra). Loss of indicia of differentiation may be indicate transformation, including loss of differentiation markers, cell rounding, loss of adhesion, loss of polarity, loss of contact inhibition, loss of anchorage dependence, protease release, increased sugar transport, decreased serum requirement, and expression of fetal antigens.

Generation and Genetic Analysis of Animals and Cell Lines with Altered Expression of p53 Gene Both genetically modified animal models (i.e. in vivo models), such as *C. elegans* and Drosophila, and in vitro models such as genetically engineered cell lines expressing or mis-expressing p53 genes, are useful for the functional analysis of these proteins. Model systems that display detectable phenotypes, can be used for the identification and characterization of p53 genes or other genes of interest and/or phenotypes associated with the mutation or mis-expression of p53. The term "mis-expression" as used herein encompasses mis-expression due to gene mutations. Thus, a mis-expressed p53 protein may be one having an amino acid sequence that differs from wild-type (i.e. it is a derivative of the normal protein). A mis-expressed p53 protein may also be one in which one or more N- or C-terminal amino acids have been deleted, and thus is a "fragment" of the normal protein. As used herein, "mis-expression" also includes ectopic expression (e.g. by altering the normal spatial or temporal expression), over-expression (e.g. by multiple gene copies), underexpression, non-expression (e.g. by gene knockout or blocking expression that would otherwise normally occur), and further, expression in ectopic tissues.

The in vivo and in vitro models may be genetically engineered or modified so that they 1) have deletions and/or insertions of a p53 genes, 2) harbor interfering RNA sequences derived from a p53 gene, 3) have had an endogenous p53 gene mutated (e.g. contain deletions, insertions, rearrangements, or point mutations in the p53 gene), and/or 4) contain transgenes for mis-expression of wild-type or mutant forms of a p53 gene. Such genetically modified in vivo and in vitro models are useful for identification of genes and proteins that are involved in the synthesis, activation, control, etc. of p53, and also downstream effectors of p53 function, genes regulated by p53, etc. The model systems can be used for testing potential pharmaceutical and pesticidal compounds that interact with p53, for example by administering the compound to the model system using any suitable method (e.g. direct contact, ingestion, injection, etc.) and observing any changes in phenotype, for example defective movement, lethality, etc. Various genetic engineering and expression modification methods which can be used are well-known in the art, including chemical mutagenesis, transposon mutagenesis, antisense RNAi, dsRNAi, and, transgene-mediated mis-expression.

Generating Loss-of-function Mutations by Mutagenesis

Loss-of-function mutations in an insect p53 gene can be generated by any of several mutagenesis methods known in the art (Ashburner, In *Drosophila melanogaster*. A Laboratory Manual (1989), Cold Spring Harbor, N.Y., Cold Spring Harbor Laboratory Press: pp. 299–418; Fly pushing: The Theory and Practice of *Drosophila melanogaster Genetics* (1997) Cold Spring Harbor Press, Plainview, N.Y., hereinafter "Fly Pushing"). Techniques for producing mutations in a gene or genome include use of radiation (e.g., X-ray, UV, or gamma ray); chemicals (e.g., EMS, MMS, ENU, formaldehyde, etc.); and insertional mutagenesis by mobile elements including dysgenesis induced by transposon insertions, or transposon-mediated deletions, for example, male recombination, as described below. Other methods of altering expression of genes include use of transposons (e.g. P element, EP-type "overexpression trap" element, mariner element, piggyBac transposon, hermes, minos, sleeping beauty, etc.) to misexpress genes; antisense; double-stranded RNA interference; peptide and RNA aptamers; directed deletions; homologous recombination; dominant negative alleles; and intrabodies.

Transposon insertions lying adjacent to a p53 gene can be used to generate deletions of flanking genomic DNA, which if induced in the germline, are stably propagated in subsequent generations. The utility of this technique in generating deletions has been demonstrated and is well-known in the art. One version of the technique using collections of P element transposon induced recessive lethal mutations (P lethals) is particularly suitable for rapid identification of novel, essential genes in Drosophila (Cooley et al., Science (1988) 239:1121–1128; Spralding et at., PNAS (1995) 92:0824–10830). Since the sequence of the P elements are known, the genomic sequence flanking each transposon insert is determined either by plasmid rescue (Hamilton et al., PNAS (1991) 88:2731–2735) or by inverse polymerase chain reaction. A more recent version of the transposon insertion technique in male Drosophila using P elements is known as P-mediated male recombination (Preston and Engels, Genetics (1996) 144:1611–1638).

Generating Loss-of-function Phenotypes Using RNA-based Methods p53 genes may be identified and/or characterized by generating loss-of-function phenotypes in animals of interest through RNA-based methods, such as antisense RNA (Schubiger and Edgar, Methods in Cell Biology (1994) 44:697–713). One form of the antisense RNA method involves the injection of embryos with an antisense RNA that is partially homologous to the gene of interest (in this case the p53 gene). Another form of the antisense RNA method involves expression of an antisense RNA partially homologous to the gene of interest by operably joining a portion of the gene of interest in the antisense orientation to a powerful promoter that can drive the expression of large quantities of antisense RNA, either generally throughout the animal or in specific tissues. Antisense RNA-generated loss-of-function phenotypes have been reported previously for several Drosophila genes including cactus, pecanex, and Krüppel (LaBonne et al., Dev. Biol. (1989) 136(1):1–16; Schuh and Jackie, Genome (1989) 31(1):422–425; Geisler et al., Cell (1992) 71(4):613–621).

Loss-of-function phenotypes can also be generated by cosuppression methods (Bingham, Cell (1997) 90(3) :385–387; Smyth, Curr. Biol. (1997) 7(12):793–795; Que and Jorgensen, Dev. Genet. (1998) 22(1):100–109). Cosuppression is a phenomenon of reduced gene expression produced by expression or injection of a sense strand RNA corresponding to a partial segment of the gene of interest. Cosuppression effects have been employed extensively in plants and *C. elegans* to generate loss-of-function phenotypes. Cosuppression in Drosophila has been shown, where reduced expression of the Adh gene was induced from a white-Adh transgene (Pal-Bhadra et al., Cell (1997) 90(3) :479–490).

Another method for generating loss-of-function phenotypes is by double-stranded RNA interference (dsRNAi). This method is based on the interfering properties of double-stranded RNA derived from the coding regions of gene, and has proven to be of great utility in genetic studies of *C. elegans* (Fire et al., Nature (1998) 391:806–811), and can also be used to generate loss-of-function phenotypes in Drosophila (Kennerdell and Carthew, Cell (1998) 95:1017–1026; Misquitta and Patterson PNAS (1999) 96:1451–1456). Complementary sense and antisense RNAs derived from a substantial portion of a gene of interest, such as p53 gene, are synthesized in vitro, annealed in an injection buffer, and introduced into animals by injection or other suitable methods such as by feeding, soaking the animals in a buffer containing the RNA, etc. Progeny of the dsRNA treated animals are then inspected for phenotypes of interest (PCT publication no. WO99/32619).

dsRNAi can also be achieved by causing simultaneous expression in vivo of both sense and anti sense RNA from appropriately positioned promoters operably fused to p53 sequences. Alternatively, the living food of an animal can be engineered to express sense and antisense RNA, and then fed to the animal. For example, *C. elegans* can be fed engineered *E. coli*, Drosophila can be fed engineered baker's yeast, and insects such as Leptinotarsa and Heliothis and other plant-eating animals can be fed transgenic plants engineered to produce the dsRNA.

RNAi has also been successfully used in cultured Drosophila cells to inhibit expression of targeted proteins (Dixon lab, University of Michigan. Thus, cell lines in culture can be manipulated using RNAi both to perturb and study the function of p53 pathway components and to validate the efficacy of therapeutic or pesticidal strategies which involve the manipulation of this pathway. A suitable protocol is described in Example 13.

Generating Loss-of-function Phenotypes Using Peptide and RNA Aptamers

Another method for generating loss-of-function phenotypes is by the use of peptide aptamers, which are peptides or small polypeptides that act as dominant inhibitors of protein function. Peptide aptamers specifically bind to target proteins, blocking their function ability (Kolonin and Finley, PNAS (1998) 95:14266–14271). Due to the highly selective nature of peptide aptamers, they may be used not only to target a specific protein, but also to target specific functions of a given protein (e.g. transcription function). Further, peptide aptamers may be expressed in a controlled fashion by use of promoters which regulate expression in a temporal, spatial or inducible manner. Peptide aptamers act dominantly; therefore, they can be used to analyze proteins for which loss-of-function mutants are not available.

Peptide aptamers that bind with high affinity and specificity to a target protein my be isolated by a variety of techniques known in the art. In one method, they are isolated from random peptide libraries by yeast two-hybrid screens (Xu et al., PNAS (1997) 94:12473–12478. They can also be isolated from phage libraries (Hoogenboom et al., Immunotechnology (1998) 4:1–20) or chemically generated peptides/libraries.

RNA aptamers are specific RNA ligands for proteins, that can specifically inhibit protein function of the gene (Good et al., Gene Therapy (1997)4:45–54; Ellington, et al., Biotechnol. Annu. Rev. (1995) 1:185–214). In vitro selection methods can be used to identify RNA aptamers having a selected specificity (Bell et al., J. Biol. Chem. (1998) 273:14309–14314). It has been demonstrated that RNA aptamers can inhibit protein function in Drosophila (Shi et al., Proc. Natl. Acad. Sci USA (19999) 96:10033–10038). Accordingly, RNA aptamers can be used to decrease the expression of p53 protein or derivative thereof, or a protein that interacts with the p53 protein.

Transgenic animals can be generated to test peptide or RNA aptamers in vivo (Kolonin and Finley, supra). For example, transgenic Drosophila lines expressing the desired aptamers may be generated by P element mediated transformation (discussed below). The phenotypes of the progeny expressing the aptamers can then be characterized.

Generating Loss of Function Phenotypes Using Intrabodies

Intracellularly expressed antibodies, or intrabodies, are single-chain antibody molecules designed to specifically bind and inactivate target molecules inside cells. Intrabodies have been used in cell assays and in whole organisms such as Drosophila (Chen et al., Hum. Gen. Ther. (1994) 5:595–601; Hassanzadeh et al., Febs Lett. (1998) 16(1, 2):75–80 and 81–86). Inducible expression vectors can be constructed with intrabodies that react specifically with p53 protein. These vectors can be introduced into model organisms and studied in the same manner as described above for aptamers.

Transgenesis

Typically, transgenic animals are created that contain gene fusions of the coding regions of the p53 gene (from either genomic DNA or cDNA) or genes engineered to encode antisense RNAs, cosuppression RNAs, interfering dsRNA, RNA aptamers, peptide aptamers, or intrabodies operably joined to a specific promoter and transcriptional enhancer whose regulation has been well characterized, preferably heterologous promoters/enhancers (i.e. promoters/enhancers that are non-native to the p53 genes being expressed).

Methods are well known for incorporating exogenous nucleic acid sequences into the genome of animals or cultured cells to create transgenic animals or recombinant cell lines. For invertebrate animal models, the most common methods involve the use of transposable elements. There are several suitable transposable elements that can be used to incorporate nucleic acid sequences into the genome of model organisms. Transposable elements are also particularly useful for inserting sequences into a gene of interest so that the encoded protein is not properly expressed, creating a "knock-out" animal having a loss-of-function phenotype. Techniques are well-established for the use of P element in Drosophila (Rubin and Spradling, Science (1982) 218:348–53; U.S. Pat. No. 4,670,388). Additionally, transposable elements that function in a variety of species, have been identified, such as PiggyBac (Thibault et al., Insect Mol Biol (1999) 8(1): 119–23), hobo, and hermes.

P elements, or marked P elements, are preferred for the isolation of loss-of-function mutations in Drosophila p53 genes because of the precise molecular mapping of these genes, depending on the availability and proximity of preexisting P element insertions for use as a localized transposon source (Hamilton and Zinn, Methods in Cell Biology (1994) 44:81–94; and Wolfner and Goldberg, Methods in Cell Biology (1994) 44:33–80). Typically, modified P elements are used which contain one or more elements that allow detection of animals containing the P element. Most often, marker genes are used that affect the eye color of Drosophila, such as derivatives of the Drosophila white or rosy genes (Rubin and Spradling, supra; and Klemenz et al., Nucleic Acids Res. (1987) 15(10):3947–3959). However; in principle, any gene can be used as a marker that causes a reliable and easily scored phenotypic change in transgenic animals. Various other markers include bacterial plasmid sequences having selectable markers such as ampicillin resistance (Steller and Pirrotta, EMBO. J. (1985) 4:167–171); and lacZ sequences fused to a weak general promoter to detect the presence of enhancers with a developmental expression pattern of interest (Bellen et al., Genes Dev. (1989) 3(9):1288–1300). Other examples of marked P elements useful for mutagenesis have been reported (Nucleic Acids Research (1998) 26:85–88.

A preferred method of transposon mutagenesis in Drosophila employs the "local hopping" method (Tower et al. (Genetics (1993)133:347–359). Each new P insertion-line can be tested molecularly for transposition of the P element into the gene of interest (e.g. p53) by assays based on PCR. For each reaction, one PCR primer is used that is homologous to sequences contained within the P element and a second primer is homologous to the coding region or flanking regions of the gene of interest. Products of the PCR reactions are detected by agarose gel electrophoresis. The sizes of the resulting DNA fragments reveal the site of P element insertion relative to the gene of interest. Alternatively, Southern blotting and restriction mapping using DNA probes derived from genomic DNA or cDNAs of the gene of interest can be used to detect transposition events that rearrange the genomic DNA of the gene. P transposition events that map to the gene of interest can be assessed for phenotypic effects in heterozygous or homozygous mutant Drosophila.

In another embodiment, Drosophila lines carrying P insertions in the gene of interest, can be used to generate localized deletions using known methods (Kaiser, Bioassays (1990) 12(6):297–301; Harnessing the power of Drosophila genetics, In *Drosophila melanogaster*: Practical Uses in Cell and Molecular Biology, Goldstein and Fyrberg, Eds., Academic Press, Inc. San Diego, Calif.). This is particularly useful if no P element transpositions are found that disrupt the gene of interest. Briefly, flies containing P elements inserted near, the gene of interest are exposed to a further round of transposase to induce excision of the element. Progeny in which the transposon has excised are typically identified by loss of the eye color marker associated with the transposable element. The resulting progeny will include flies with either precise or imprecise excision of the P element, where the imprecise excision events often result in deletion of genomic DNA neighboring the site of P insertion. Such progeny are screened by molecular techniques to identify deletion events that remove genomic sequence from the gene of interest, and assessed for phenotypic effects in heterozygous and homozygous mutant Drosophila.

Recently a transgenesis system has been described that may have universal applicability in all eye-bearing animals and which has been proven effective in delivering transgenes to diverse insect species (Berghammer et al., Nature (1999) 402:370–371). This system includes: an artificial promoter active in eye tissue of all animal species, preferably containing three Pax6 binding sites positioned upstream of a TATA box (3xP3; Sheng et al. Genes Devel. (1997) 11:4122–1131); a strong and visually detectable marker gene, such as GFP or or other autofluorescent protein genes (Pasher et al., Gene (1992) 111:229–233; U.S. Pat. No. 5,491,084); and promiscuous vectors capable of delivering transgenes to a broad range of animal species, for example transposon-based vectors derived from Hermes, PiggyBac, or mariner, or vectors based on pantropic $VSV_G$-pseudotyped retroviruses. (Burns et al., In Vitro Cell Dev Biol Anim (1996) 32:78–84; Jordan et al., Insect Mol Biol (1998) 7: 215–222; U.S. Pat. No. 5,670,345). Since the same transgenesis system can be used in a variety of phylogenetically diverse animals, comparative functional studies are greatly facilitated, which is especially helpful in evaluating new applications to pest management.

In addition to creating loss-of-function phenotypes, transposable elements can be used to incorporate p53, or fragments or derivatives thereof, as an additional gene into any region of an animal's genome resulting in mis-expression (including over-expression) of the gene. A preferred vector designed specifically for misexpression of genes in transgenic Drosophila, is derived from pGMR (Hay et al., Development (1994) 120:2121–2129), is 9 Kb long, and contains: an origin of replication for *E. coli*; an ampicillin resistance gene; P element transposon 3' and 5' ends to mobilize the inserted sequences; a White marker gene; an expression unit comprising the TATA region of hsp70 enhancer and the 3'untranslated region of α-tubulin gene. The expression unit contains a first multiple cloning site (MCS) designed for insertion of an enhancer and a second MCS located 500 bases downstream, designed for the insertion of a gene of interest. As an alternative to transposable elements, homologous recombination or gene targeting techniques can be used to substitute a heterologous p53 gene or fragment or derivative for one or both copies of the animal's homologous gene. The transgene can be under the regulation of either an exogenous or an endogenous promoter element, and be inserted as either a minigene or a large genomic fragment. Gene function can be analyzed by ectopic expression, using, for example, Drosophila (Brand et al., Methods in Cell Biology (1994) 44:635–654).

Examples of well-characterized heterologous promoters that may be used to create transgenic Drosophila include heat shock promoters/enhancers such as the hsp70 and hsp83 genes. Eye tissue specific promoters/enhancers include eyeless (Mozer and Benzer, Development (1994) 120:1049–1058), sevenless (Bowtell et al., PNAS (1991) 88(15):6853–6857), and glass-responsive promoters/enhancers (Quiring et al., Science (1994) 265:785–789). Wing tissue specific enhancers/promoters can be derived from the dpp or vestigal genes (Staehling-Hampton et al., Cell Growth Differ. (1994) 5(6):585–593; Kim et al., Nature (1996) 382:133–138). Finally, where it is necessary to restrict the activity of dominant active or dominant negative transgenes to regions where p53 is normally active, it may be useful to use endogenous p53 promoters. The ectopic expression of DMp53 in Drosophila larval eye using glass-responsive enhancer elements is described in Example 12 below.

In Drosophila, binary control systems that employ exogenous DNA are useful when testing the mis-expression of genes in a wide variety of developmental stage-specific and tissue-specific patterns. Two examples of binary exogenous regulatory systems include the UAS/GAL4 system from yeast (Hay et al., PNAS (1997) 94(10):5195–5200; Ellis et al., Development (1993) 119(3):855–865), and the "Tet system" derived from *E. coli* (Bello et al., Development (1998)125:2193–2202). The UAS/GAL4 system is a well-established and powerful method of mis-expression which employs the $UAS_G$ upstream regulatory, sequence for control of promoters by the yeast GAL4 transcriptional activator protein (Brand and Perrimon, Development (1993) 118(2) :401–15). In this approach, transgenic Drosophila, termed "target" lines, are generated where the gene of interest to be mis-expressed is operably fused to an appropriate promoter controlled by $UAS_G$. Other transgenic Drosophila strains, termed "driver" lines, are generated where the GAL4 coding region is operably fused to promoters/enhancers that direct the expression of the GAL4 activator protein in specific tissues, such as the eye, wing, nervous system, gut, or musculature. The gene of interest is not expressed in the target lines for lack of a transcriptional activator to drive transcription from the promoter joined to the gene of interest. However, when the UAS-target line is crossed with a GAL4 driver line, mis-expression of the gene of interest is induced in resulting progeny in a specific pattern that is characteristic for that GAL4 line. The technical simplicity of this approach makes it possible to sample the effects of directed mis-expression of the gene of interest in a wide variety of tissues by generating one transgenic target line with the gene of interest, and crossing that target line with a panel of preexisting driver lines.

In the "Tet" binary control system, transgenic Drosophila driver lines are generated where the coding region for a tetracycline-controlled transcriptional activator (tTA) is operably fused to promoters/enhancers that direct the expression of tTA in a tissue-specific and/or developmental stage-specific manner. The driver lines are crossed with transgenic Drosophila target lines where the coding region for the gene of interest to be mis-expressed is operably fused to a promoter that possesses a tTA-responsive regulatory element. When the resulting progeny are supplied with food supplemented with a sufficient amount of tetracycline, expression of the gene of interest is blocked. Expression of the gene of interest can be induced at will simply by removal of tetracycline from the food Also, the level of expression of the gene of interest can be adjusted by varying the level of tetracycline in the food. Thus, the use of the Tet system as a binary control mechanism for mis-expression has the advantage of providing a means to control the amplitude and timing of mis-expression of the gene of interest, in addition to spatial control. Consequently, if a p53 gene has lethal or deleterious effects when mis-expressed at an early stage in development, such as the embryonic or larval stages, the function of the gene in the adult can still be assessed by adding tetracycline to the food during early stages of development and removing tetracycline later so as to induce mis-expression only at the adult stage.

Dominant negative mutations, by which the mutation causes a protein to interfere with the normal function of a wild-type copy of the protein, and which can result in loss-of-function or reduced-function phenotypes in the presence of a normal copy of the gene, can be made using known methods (Hershkowitz, Nature (1987) 329:219–222). In the case of active monomeric proteins, overexpression of an inactive form, achieved, for example, by linking the mutant gene to a highly active promoter, can cause competition for natural substrates or ligands sufficient to significantly reduce net activity of the normal protein. Alternatively, changes to active site residues can be made to create a virtually irreversible association with a target.

Assays for Change in Gene Expression

Various expression analysis techniques may be used to identify genes which are differentially expressed between a cell line or an animal expressing a wild type p53 gene compared to another cell line or animal expressing a mutant p53 gene. Such expression profiling techniques include differential display, serial analysis of gene expression (SAGE), transcript profiling coupled to a gene database query, nucleic acid array technology, to subtractive hybridization, and proteome analysis (e.g. mass-spectrometry and two-dimensional protein gels). Nucleic acid array technology may be used to determine the genome-wide expression pattern in a normal animal for comparison with an animal having a mutation in the p53 gene. Gene expression profiling can also be used to identify other genes or proteins that may have a functional relation to p53. The genes are identified by detecting changes in their expression levels following mutation, over-expression, under-expression, mis-expression or knock-out, of the p53 gene.

Phenotypes Associated with p53 Gene Mutations

After isolation of model animals carrying mutated or mis-expressed p53 genes or inhibitory RNAs, animals are carefully examined for phenotypes of interest. For analysis of p53 genes that have been mutated, animal models that are both homozygous and heterozygous for the altered p53 gene are analyzed. Examples of specific phenotypes that may be investigated include lethality; sterility; feeding behavior, tumor formation, perturbations in neuromuscular function including alterations in motility, and alterations in sensitivity to pharmaceuticals. Some phenotypes more specific to flies include alterations in: adult behavior such as, flight ability, walking, grooming, phototaxis, mating or egg-laying; alterations in the responses of sensory organs, changes in the morphology, size or number of adult tissues such as, eyes, wings, legs, bristles, antennae, gut, fat body, gonads, and musculature; larval tissues such as mouth parts, cuticles, internal tissues or imaginal discs; or larval behavior such as feeding, molting, crawling, or puparian formation; or developmental defects in any germline or embryonic tissues.

Genomic sequences containing a p53 gene can be used to engineer an existing mutant insect line, using the transgenesis methods previously described, to determine whether the mutation is in the p53 gene. Briefly, germline transformants are crossed for complementation testing to an existing or newly created panel of insect lines whose mutations have been mapped to the vicinity of the gene of interest (Fly Pushing, supra). If a mutant line is discovered to be rescued by the genomic fragment, as judged by complementation of the mutant phenotype, then the mutant line likely harbors a mutation in the p53 gene. This prediction can be further confirmed by sequencing the p53 gene from the mutant line to identify the lesion in the p53-gene.

Identification of Genes That Modify p53 Genes

The characterization of new phenotypes created by mutations or misexpression in p53 genes enables one to test for genetic interactions between p53 genes and other genes that may participate in the same, related, or interacting genetic or biochemical pathway(s). Individual genes can be used as starting points in large-scale genetic modifier screens as described in more detail below. Alternatively, RNAi methods can be used to simulate loss-of-function mutations in the genes being analyzed. It is of particular interest to investigate whether there are any interactions of p53 genes with other well-characterized genes, particularly genes involved in regulation of the cell cycle or apoptosis.

Genetic Modifier Screens

A genetic modifier screen using invertebrate model organisms is a particularly preferred method for identifying genes that interact with p53 genes, because large numbers of animals can be systematically screened making it more possible that interacting genes will be identified. In Drosophila, a screen of up to about 10,000 animals is considered to be a pilot-scale screen. Moderate-scalescreens usually employ about 10,000 to about 50,000 flies, and large-scale screens employ greater than about 50,000 flies. In a genetic modifier screen, animals having a mutant phenotype due to a mutation in or misexpression of the p53 gene are further mutagenized, for example by chemical mutagenesis or transposon mutagenesis.

The procedures involved in typical Drosophila genetic modifier screens are well-known in the art (Wolfner and Goldberg, Methods in Cell Biology (1994) 44:33–80; and Karim et al., Genetics (1996) 143:315–329). The procedures used differ depending upon the precise nature of the mutant allele being modified. If the mutant allele is genetically recessive, as is commonly the situation for a loss-of-function allele, then most typically males, or in some cases females, which carry one copy of the mutant allele are exposed to an effective mutagen, such as EMS, MMS, ENU, triethylamine, diepoxyalkanes, ICR-170, formaldehyde, X-rays, gamma rays, or ultraviolet radiation. The mutagenized animals are crossed to animals of the opposite sex that also carry the mutant allele to be modified. In the case where the mutant allele being modified is genetically dominant, as is commonly the situation for ectopically expressed genes, wild type males are mutagenized and crossed to females carrying the mutant allele to be modified.

The progeny of the mutagenized and crossed flies that exhibit either enhancement or suppression of the original phenotype are presumed to have mutations in other genes, called "modifier genes", that participate in the same phenotype-generating pathway. These progeny are immediately crossed to adults containing balancer chromosomes and used as founders of a stable genetic line. In addition, progeny of the founder adult are retested under the original screening conditions to ensure stability and reproducibility of the phenotype. Additional secondary screens may be employed, as appropriate, to confirm the suitability of each new modifier mutant line for further analysis.

Standard techniques used for the mapping of modifiers that come from a genetic screen in Drosophila include meiotic mapping with visible or molecular genetic markers; male-specific recombination mapping relative to P-element insertions; complementation analysis with deficiencies, duplications, and lethal P-element insertions; and cytological analysis of chromosomal aberrations (Fly Pushing, supra). Genes corresponding to modifier mutations that fail to complement a lethal P-element may be cloned by plasmid rescue of the genomic sequence surrounding that P-element. Alternatively, modifier genes may be mapped by phenotype rescue and positional cloning (Sambrook et al., supra).

Newly identified modifier mutations can be tested directly for interaction with other genes of interest known to be involved or implicated with p53 genes using methods described above. Also, the new modifier mutations can be tested for interactions with, genes in other pathways that are not believed to be related to regulation of cell cycle or apoptosis. New modifier mutations that exhibit specific genetic interactions with other genes implicated in cell cycle regulation or apoptosis, and not with genes in unrelated pathways, are of particular interest.

The modifier mutations may also be used to identify "complementation groups". Two modifier mutations are considered to fall within the same complementation group if animals carrying both mutations in trans exhibit essentially the same phenotype as animals that are homozygous for each mutation individually and, generally are lethal when in trans to each other (Fly Pushing, supra). Generally, individual complementation groups defined in this way correspond to individual genes.

When p53 modifier genes are identified, homologous genes in other species can be isolated using procedures based on cross-hybridization with modifier gene DNA probes, PCR-based strategies with primer sequences derived from the modifier genes, and/or computer searches of sequence databases. For therapeutic applications related to the function of p53 genes, human and rodent homologs of the modifier genes are of particular interest.

Although the above-described Drosophila genetic modifier screens are quite powerful and sensitive, some genes that interact with p53 genes may be missed in this approach, particularly if there is functional redundancy of those genes. This is because the vast majority of the mutations generated in the standard mutagenesis methods will be loss-of-function mutations, whereas gain-of-function mutations that could reveal genes with functional redundancy will be relatively rare. Another method of genetic screening in Drosophila has been developed that focuses specifically on systematic gain-of-function genetic screens (Rorth et al., Development (1998) 125:1049–1057). This method is based on a modular mis-expression system utilizing components of the GAL4/UAS system (described above) where a modified P element, termed an "enhanced P" (EP) element, is genetically engineered to contain a GAL4-responsive UAS element and promoter. Any other transposons can also be used for this system. The resulting transposon is used to randomly tag genes by insertional mutagenesis (similar to the method of P element mutagenesis described above). Thousands of transgenic Drosophila strains, termed EP lines, can be generated, each containing a specific UAS-tagged gene. This approach takes advantage of the preference of P elements to insert at the 5'-ends of genes. Consequently, many of the genes that are tagged by insertion of EP elements become operably fused to a GAL4-regulated promoter, and increased expression or mis-expression of the randomly tagged gene can be induced by crossing in a GAL4 driver gene.

Systematic gain-of-function genetic screens for modifiers of phenotypes induced by mutation or mis-expression of a p53 gene can be performed by crossing several thousand Drosophila EP lines individually into a genetic background containing a mutant or mis-expressed p53 gene, and further containing an appropriate GAL4 driver transgene. It is also possible to remobilize the EP elements to obtain novel insertions. The progeny of these crosses are then analyzed for enhancement or suppression of the original mutant phenotype as described above. Those identified as having mutations that interact with the p53 gene can be tested further to verify the reproducibility and specificity of this genetic interaction. EP insertions that demonstrate a specific genetic interaction with a mutant or mis-expressed p53 gene, have a physically tagged new gene which can be identified and sequenced using PCR or hybridization screening methods, allowing the isolation of the genomic DNA adjacent to the position of the EP element insertion.

Identification of Molecules that Interact with p53

A variety of methods can be used to identify or screen for molecules, such as proteins or other molecules, that interact with p53 protein, or derivatives or fragments thereof. The assays may employ purified p53 protein, or cell lines or a model organism such as Drosophila that has been genetically engineered to express p53 protein. Suitable screening methodologies are well known in the art to test for proteins and other molecules that interact with a gene/protein of interest (see e.g., PCT International Publication No. WO 96/34099). The newly identified interacting molecules may provide new targets for pharmaceutical agents. Any of a variety of exogenous molecules, both naturally occurring and/or synthetic (e.g., libraries of small molecules or peptides, or phage display libraries), may be screened for binding capacity. In a typical binding experiment, the p53 protein or fragment is mixed with candidate molecules under conditions conducive to binding, sufficient time is allowed for any binding to occur, and assays are performed to test for bound complexes. A variety of assays to find interacting proteins are known in the art, for example, immunoprecipitation with an antibody that binds to the protein in a complex followed by analysis by size fractionation of the immunoprecipitated proteins (e.g. by denaturing or nondenaturing polyacrylamide gel electrophoresis), Western analysis, non-denaturing gel electrophoresis, etc.

Two-hybrid Assay Systems

A preferred method for identifying interacting proteins is a two-hybrid assay system or variation thereof (Fields and Song, Nature (1989) 340:245–246; U.S. Pat. No. 5,283,173; for review see Brent and Finley, Annu. Rev. Genet. (1997) 31:663–704). The most commonly used two-hybrid screen system is performed using yeast. All systems share three elements: 1) a gene that directs the synthesis of a "bait" protein fused to a DNA binding domain; 2) one or more "reporter" genes having an upstream binding site for the bait, and 3) a gene that directs the synthesis of a "prey" protein fused to an activation domain that activates transcription of the reporter gene. For the screening of proteins that interact with p53 protein, the "bait" is preferably a p53 protein, expressed as a fusion protein to a DNA binding domain; and the "prey" protein is a protein to be tested for ability to interact with the bait, and is expressed as a fusion protein to a transcription activation domain. The prey proteins can be obtained from recombinant biological libraries expressing random peptides.

The bait fusion protein can be constructed using any suitable DNA binding domain, such as the *E. coli* LexA repressor protein, or the yeast GAL4 protein (Bartel et al., BioTechniques (1993) 14:920–924, Chasman et al., Mol. Cell. Biol. (1989) 9:4746–4749; Ma et al., Cell (1987) 48:847–853; Ptashne et al., Nature (1990) 346:329–331). The prey fusion protein can be constructed using any suitable activation domain such as GAL4, VP-16, etc. The preys may contain useful moieties such as nuclear localization signals (Ylikomi et al., EMBO J. (1992) 11:3681–3694; Dingwall and Laskey, Trends Biochem. Sci. Trends Biochem. Sci. (1991) 16:479–481) or epitope tags (Allen et al., Trends Biochem. Sci. Trends Biochem. Sci. (1995) 20:511–516) to facilitate isolation of the encoded proteins. Any reporter gene can be used that has a detectable phenotype such as reporter genes that allow cells expressing them to be selected by growth on appropriate medium (e.g. HIS3, LEU2 described by Chien et al., PNAS (1991) 88:9572–9582; and Gyuris et al., Cell (1993) 75:791–803). Other reporter genes, such as LacZ and GFP, allow cells expressing them to be visually screened (Chien et al., supra).

Although the preferred host for two-hybrid screening is the yeast, the host cell in which the interaction assay and transcription of the reporter gene occurs can be any cell, such as mammalian (e.g. monkey, mouse, rat, human, bovine), chicken, bacterial, or insect cells. Various vectors and host strains for expression of the two fusion protein populations in yeast can be used (U.S. Pat. No. 5,468,614; Bartel et al., Cellular Interactions in Development (1993) Hartley, ed., Practical Approach Series xviii, IRL Press at Oxford University Press, New York, N.Y., pp. 153–179; and Fields and Sternglanz, Trends In Genetics (1994) 10:286–292). As an example of a mammalian system, interaction of activation tagged VP16 derivatives with a GAL4-derived bait drives expression of reporters that direct the synthesis of hygromycin B phosphotransferase, chloramphenicol acetyltransferase, or CD4 cell surface antigen (Fearon et al., PNAS (1992) 89:7958–7962). As another example, interaction of VP16-tagged derivatives with GAL4-derived baits drives the synthesis of SV40 T antigen, which in turn promotes the replication of the prey plasmid, which carries an SV40 origin (Vasavada et al., PNAS (1991) 88:10686–10690).

Typically, the bait p53 gene and the prey library of chimeric genes are combined by mating the two yeast strains on solid or liquid media for a period of approximately 6–8 hours. The resulting diploids contain both kinds of chimeric genes, i.e., the DNA-binding domain fusion and the activation domain fusion. Transcription of the reporter gene can be detected by a linked replication assay in the case of SV40 T antigen (Vasavada et al., supra) or using immunoassay methods (Alam and Cook, Anal. Biochem. (1990) 188:245–254). The activation of other reporter genes like URA3, HIS3, LYS2, or LEU2 enables the cells to grow in the absence of uracil, histidine, lysine, or leucine, respectively, and hence serves as a selectable marker. Other types of reporters are monitored by measuring a detectable signal. For example, GFP and lacZ have gene products that are fluorescent and chromogenic, respectively.

After interacting proteins have been identified, the DNA sequences encoding the proteins can be isolated. In one method, the activation domain sequences or DNA-binding domain sequences (depending on the prey hybrid used) are amplified, for example, by PCR using pairs of oligonucleotides primers specific for the coding region of the DNA binding domain or activation domain. If a shuttle (yeast to *E. coli*) vector is used to express the fusion proteins, the DNA sequences encoding the proteins can be isolated by transformation of *E. coli* using the yeast, DNA and recovering the plasmids from *E. coli*. Alternatively, the yeast vector can be isolated, and the insert encoding the fusion protein subcloned into a bacterial expression vector, for growth of the plasmid in *E. coli*.

Antibodies and Immunoassay p53 proteins encoded by any of SEQ ID NOs:2, 4, 6, 8, or 10 and derivatives and fragments thereof, such as those discussed above, may be used as an immunogen to generate monoclonal or polyclonal antibodies and antibody fragments or derivatives (e.g. chimeric, single chain, Fab fragments). For example, fragments of a p53 protein, preferably those identified as hydrophilic, are used as immunogens for antibody production using art-known methods such as by hybridomas; production of monoclonal antibodies in germ-free animals (PCT/US90/02545); the use of human hybridomas (Cole et al., PNAS (1983) 80:2026–2030; Cole et al., in Monoclonal Antibodies and Cancer Therapy (1985) Alan R. Liss, pp. 77–96), and production of humanized antibodies (Jones et al., Nature (1986) 321:522–525; U.S. Pat. No. 5,530,101). In a particular embodiment, p53 polypeptide fragments provide specific antigens and/or immunogens, especially when coupled to carrier proteins. For example, peptides are covalently coupled to keyhole limpet antigen (KLH) and the conjugate is emulsified in Freund's complete adjuvant. Laboratory rabbits are immunized according to conventional protocol and bled. The presence of specific antibodies is assayed by solid phase immunosorbent assays using immobilized corresponding polypeptide. Specific activity or function of the antibodies produced may be determined by convenient in vitro, cell-based, or in vivo assays: e.g. in vitro binding assays, etc. Binding affinity may be assayed by determination of equilibrium constants of antigen-antibody association (usually at least about $10^7$ $M^{-1}$, preferably at least about $10^8$ $M^{-1}$, more preferably at least about $10^9$ $M^{-1}$). Example 11 below further describes the generation of anti-DMp53 antibodies.

Immunoassays can be used to identify proteins that interact with or bind to p53 protein. Various assays are available for testing the ability of a protein to bind to or compete with binding to a wild-type p53 protein or for binding to an anti-p53 protein antibody. Suitable assays include radioimmunoassays, ELISA (enzyme linked immunosorbent assay), immunoradiometric assays, gel diffusion precipitin reactions, immunodiffusion assays, in situ immunoassays (e.g., using colloidal gold, enzyme or radioisotope labels), western blots, precipitation reactions, agglutination assays (e.g., gel agglutination assays, hemagglutination assays), complement fixation assays, immunofluorescence assays, protein A assays, immunoelectrophoresis assays, etc.

Identification of Potential Drug Targets

Once new p53 genes or p53 interacting genes are identified, they can be assessed as potential drug or pesticide targets using animal models such as Drosophila or other insects, or using cells that express endogenous p53, or that have been engineered to express p53.

Assays of Compounds on Insects

Potential insecticidal compounds can be administered to insects in a variety of ways, including orally (including addition to synthetic diet, application to plants or prey to be consumed by the test organism), topically (including spraying, direct application of compound to animal, allowing animal to contact a treated surface), or by injection. Insecticides are typically very hydrophobic molecules and must commonly be dissolved in organic solvents, which are allowed to evaporate in the case of methanol or acetone, or at low concentrations can be included to facilitate uptake (ethanol, dimethyl sulfoxide).

The first step in an insect assay is usually the determination of the minimal lethal dose (MLD) on the insects after a chronic exposure to the compounds. The compounds are usually diluted in DMSO, and applied to the food surface bearing 0–48 hour old embryos and larvae. In addition to MLD, this step allows the determination of the fraction of eggs that hatch, behavior of the larvae, such as how they move/feed compared to untreated larvae, the fraction that survive to pupate, and the fraction that eclose (emergence of the adult insect from puparium). Based on these results more detailed assays with shorter exposure times may be designed, and larvae might be dissected to look for obvious morphological defects. Once the MLD is determined, more specific acute and chronic assays can be designed.

In a typical acute assay, compounds are applied to the food surface for embryos, larvae, or adults, and the animals are observed after 2 hours and after an overnight incubation. For application on embryos, defects in development and the percent that survive to adulthood are determined. For larvae, defects in behavior, locomotion, and molting may be observed. For application on adults, behavior and neurological defects are observed, and effects on fertility are noted. Any deleterious effect on insect survival, motility and fertility indicates that the compound has utility in controlling pests.

For a chronic exposure assay, adults are placed on vials containing the compounds for 48 hours, then transferred to a clean container and observed for fertility, neurological defects, and death.

Assay of Compounds using Cell Cultures

Compounds that modulate (e.g. block or enhance) p53 activity may be tested on cells expressing endogenous normal or mutant p53s, and/or on cells transfected with vectors that express p53, or derivatives or fragments of p53. The compounds are added at varying concentration and their ability to modulate the activity of p53 genes is determined using any of the assays for tumor suppressor genes described above (e.g. by measuring transcription activity, apoptosis, proliferation/cell cycle, and/or transformation). Compounds that selectively modulate p53 are identified as potential drug candidates having p53 specificity.

Identification of small molecules and compounds as potential pharmaceutical compounds from large chemical libraries requires high-throughput screening (HTS) methods (Bolger, Drug Discovery Today (1999) 4:251–253). Several of the assays mentioned herein can lend themselves to such screening methods. For example, cells or cell lines expressing wild type or mutant p53 protein or its fragments, and a reporter gene can be subjected to compounds of interest, and depending on the reporter genes, interactions can be measured using a variety of methods such as color detection, fluorescence detection (e.g. GFP), autoradiography, scintillation analysis, etc.

Agricultural Uses of Insect p53 Sequences

Insect p53 genes may be used in controlling agriculturally important pest species. For example, the proteins, genes, and RNAs disclosed herein, or their fragments may have activity in modifying the growth, feeding and/or reproduction of crop-damaging insects, or insect pests of farm animals or of other animals. In general, effective pesticides exert a disabling activity on the target pest such as lethality, sterility, paralysis, blocked development, or cessation of feeding. Such pests include egg, larval, juvenile and adult forms of flies, mosquitos, fleas, moths, beetles, cicadia, grasshoppers, aphids and crickets. The functional analyses of insect p53 genes described herein has revealed roles for these genes and proteins in controlling apoptosis, response to DNA damaging agents, and protection of cells of the germline. Since overexpression of DMp53 induces apoptosis in Drosophila, the insect p53 genes and proteins in an activated form have application as "cell death" genes which if delivered to or expressed in specific target tissues such as the gut, nervous system, or gonad, would have a use in controlling insect pests. Alternatively, since DMp53 plays a role in response to DNA damaging agents such as X-rays, interference with p53 function in insects has application in sensitizing insects to DNA damaging agents for sterilization. For example, current methods for controlling pest populations through the release of irradiated insects into the environment (Knipling, J Econ Ent (1955) 48: 459–462; Knipling (1979) U.S. Dept. Agric. Handbook No. 512) could be improved by causing expression of dominant negative forms of p53 genes, proteins, or RNAs in insects and most preferably germline tissue of insects, or by exposing insects to chemical compounds which block p53 function.

Mutational analysis of insect p53 proteins may also be used in connection with the control of agriculturally-important pests. In this regard, mutational analysis of insect p53 genes provides a rational approach to determine the precise biological function of this class of proteins in invertebrates. Further, mutational analysis coupled with large-scale systematic genetic modifier screens provides a means to identify and validate other potential pesticide targets that might be constituents of the p53 signaling pathway. Tests for pesticidal activities can be any method known in the art. Pesticides comprising the nucleic acids of the insect p53 proteins may be prepared in a suitable vector for delivery to a plant or animal. Such vectors include *Agrobacterium tumefaciens* Ti plasmid-based vectors for the generation of transgenic plants (Horsch et al., Proc Natl Acad Sci U S A. (1986) 83(8):2571–2575; Fraley et al., Proc. Natl. Acad. Sci. USA (1983) 80:4803) or recombinant cauliflower mosaic virus for the incoulation of plant cells or plants (U.S. Pat. No. 4,407,956); retrovirus based vectors for the introduction of genes into vertebrate animals (Burns et al., Proc. Natl. Acad. Sci. USA (1993) 90:8033–37); and vectors based on transposable elements for incorporation into invertebrate animals using vectors and methods already described above. For example, transgenic insects can be generated using a transgene comprising a p53 gene operably fused to an appropriate inducible promoter, such as a tTA-responsive promoter, in order to direct expression of the tumor suppressor protein at an appropriate time in the life cycle of the insect. In this way, one may test efficacy as an insecticide in, for example, the larval phase of the life cycle (e.g., when feeding does the greatest damage to crops).

Recombinant or synthetic p53 proteins, RNAs or their fragments, in wild-type or mutant forms, can be assayed for insecticidal activity by injection of solutions of p53 proteins or RNAs into the hemolymph of insect larvae (Blackburn, et al., Appl. Environ. Microbiol. (1998) 64(8):3036–41; Bowen and Ensign, Appl. Environ. Microbiol. (1998) 64(8):3029–35). Further, transgenic plants that express p53 proteins or RNAs or their fragments can be tested for activity against insect pests (Estruch et al., Nat. Biotechnol. (1997) 15(2):137–41).

Insect p53 genes may be used as insect control agents in the form of recombinant viruses that direct the expression of a tumor suppressor gene in the target pest. A variety of suitable recombinant virus systems for expression of proteins in infected insect cells are well known in the art. A preferred system uses recombinant baculoviruses. The use of recombinant baculoviruses as a means to engineer expression of toxic proteins in insects, and as insect control agents, has a number of specific advantages including host specificity, environmental safety, the availability of vector systems, and the potential use of the recombinant virus directly as a pesticide without the need for purification or formulation of the tumor suppressor protein (Cory and Bishop, Mol. Biotechnol. (1997) 7(3):303–13; and U.S. Pat. Nos. 5,470,735; 5,352,451; 5,770,192; 5,759,809; 5,665,349; and 5,554,592). Thus, recombinant baculoviruses that direct the expression of insect p53 genes can be used for both testing the pesticidal activity of tumor suppressor proteins under controlled laboratory conditions, and as insect control agents in the field. One disadvantage of wild type baculoviruses as insect control agents can be the amount of time between, application of the virus and death of the target insect, typically one to two weeks. During this period, the insect larvae continue to feed and damage crops. Consequently, there is a need to develop improved baculovirus-derived insect control agents which result in a rapid cessation of feeding of infected target insects. The cell cycle and apoptotic regulatory roles of p53 in vertebrates raises the possibility that expression of tumor suppressor proteins from recombinant baculovirus, in infected insects may have a desirable effect in controlling metabolism and limiting feeding of insect pests.

Insect p53 genes, RNAs, proteins or fragments may be formulated with any carrier suitable for agricultural use, such as water, organic solvents and/or inorganic solvents. The pesticide composition may be in the form of a solid or liquid composition and may be prepared by fundamental formulation processes such as dissolving, mixing, milling, granulating, and dispersing. Compositions may contain an insect p53 protein or gene in a mixture with agriculturally acceptable excipients such as vehicles, carriers, binders, UV blockers, adhesives, hemecants, thickeners, dispersing agents, preservatives and insect attractants. Thus the compositions of the invention may, for example, be formulated as a solid comprising the active agent and a finely divided solid carrier. Alternatively, the active agent may be contained in liquid compositions including dispersions, emulsions and suspensions thereof. Any suitable final formulation may be used, including for example, granules, powder, bait pellets (a solid composition containing the active agent and an insect attractant or food substance), microcapsules, water dispersible granules, emulsions and emulsified concentrates. Examples of adjuvant or carriers suitable for use with the present invention include water, organic solvent, inorganic solvent, talc, pyrophyllite, synthetic fine silica, attapugus clay, kieselguhr chalk, diatomaceous earth, lime, calcium carbonate, bontonite, fuller's earth, cottonseed hulls, wheat flour, soybean flour, pumice, tripoli, wood flour, walnut shell flour, redwood flour, and lignin. The compositions may also include conventional insecticidal agents and/or may be applied in conjunction with conventional insecticidal agents.

EXAMPLES

The following examples describe the isolation and cloning of the nucleic acid sequence of SEQ ID NOs:1, 3, 5, 7, 9, and 18, and how these sequences, derivatives and fragments thereof, and gene products can be used for genetic studies to elucidate mechanisms of the p53 pathway as well as the discovery of potential pharmaceutical agents that interact with the pathway.

These Examples are provided merely as illustrative of various aspects of the invention and should not be construed to limit the invention in any way.

Example 1

Preparation of Drosophila cDNA Library

A Drosophila expressed sequence tag (EST) cDNA library was prepared as follows. Tissue from mixed stage embryos (0–20 hour), imaginal disks and adult fly heads were collected and total RNA was prepared. Mitochondrial rRNA was removed from the total RNA by hybridization with biotinylated rRNA specific oligonucleotides and the resulting RNA was selected for polyadenylated mRNA. The resulting material was then used to construct a random primed library. First strand cDNA synthesis was primed using a six nucleotide random primer. The first strand cDNA was then tailed with terminal transferase to add approximately 15 dGTP molecules. The second strand was primed using a primer which contained a Not1 site followed by a 13 nucleotide C-tail to hybridize to the G-tailed first strand cDNA. The double stranded cDNA was ligated with BstX1 adaptors and digested with Not1. The cDNA was then fractionated by size by electrophoresis on an agarose gel and the cDNA greater than 700 bp was purified. The cDNA was ligated with Not1, BstX1 digested pCDNA-sk+ vector (a derivative of pBluescript, Stratagene) and used to transform *E. coli* (XL1blue). The final complexity of the library was $6\times10^6$ independent clones.

The cDNA library was normalized using a modification of the method described by Bonaldo et al. (Genome Research (1996) 6:791–806). Biotinylated driver was prepared from the cDNA by PCR amplification of the inserts and allowed to hybridize with single stranded plasmids of the same library. The resulting double-stranded forms were removed using strepavidin magnetic beads, the remaining single stranded plasmids were converted to double stranded molecules using Sequenase (Amersham, Arlington Hills, Ill.), and the plasmid DNA stored at −20° C., prior to transformation. Aliquots of the normalized plasmid library were used to transform *E. coli* (XL1blue or DH10B), plated at moderate density, and the colonies picked into a 384-well master plate containing bacterial growth media using a Qbot robot (Genetix, Christchurch, UK). The clones were allowed to grow for 24 hours at 37° C. then the master plates were frozen at −80° C. for storage. The total number of colonies picked for sequencing from the normalized library was 240,000. The master plates were used to inoculate media for growth and preparation of DNA for use as template in sequencing reactions. The reactions were primarily carried out with primer that initiated at the 5' end of the cDNA inserts. However, a minor percentage of the clones were also sequenced from the 3' end. Clones were selected for 3' end sequencing based on either further biological interest or the selection of clones that could extend assemblies of contiguous sequences ("contigs") as discussed below. DNA sequencing was carried out using ABI377 automated sequencers and used either ABI FS, dirhodamine or BigDye chemistries (Applied Biosystems, Inc., Foster City, Calif.).

Analysis of sequences was done as follows: the traces generated by the automated sequencers were base-called using the program "Phred" (Gordon, Genome Res. (1998) 8:195–202), which also assigned quality values to each base. The resulting sequences were trimmed for quality in view of the assigned scores. Vector sequences were also removed. Each sequence was compared to all other fly EST sequences using the BLAST program and a filter to identify regions of near 100% identity. Sequences with potential overlap were then assembled into contigs using the programs "Phrap", "Phred" and "Consed" (Phil Green, University of Washington, Seattle, Wash. The resulting assemblies were then compared to existing public databases and homology to known proteins was then used to direct translation of the consensus sequence. Where no BLAST homology was available, the statistically most likely translation based on codon and hexanucleotide preference was used. The Pfam (Bateman et al., Nucleic Acids Res. (1999) 27:260–262) and Prosite (Hofman et al., Nucleic Acids Res. (1999) 27(1) :215–219) collections of protein domains were used to identify motifs in the resulting translations. The contig sequences were archived in an Oracle-based relational database (FlyTag™, Exelixis Pharmaceuticals, Inc., South San Francisco, Calif.).

Example 2

Other cDNA Libraries

A Leptinotarsa (Colorado Potato Beetle) library was prepared using the Lambda ZAP cDNA cloning kit from Stratagene (Stratagene, La Jolla, Calif., cat#200450), following manufacturer's protocols. The original cDNA used to construct the library was oligo-dt primed using mRNA from mixed stage larvae Leptinotarsa.

A Tribolium library was made using pSPORT cDNA library construction system (Life Technologies, Gaithersburg, Md.), following manufacturer's protocols. The original cDNA used to construct the library was oligo-dt primed using mRNA from adult Tribolium.

Example 3

Cloning of the p53 Nucleic Acid from Drosophila (DMp53)

The TBLASTN program (Altschul et al., supra) was used to query the FlyTag™ database with a squid p53 protein sequence (GenBank gi:1244762), chosen because the squid sequence was one of only two members of the p53 family that had been identified previously from an invertebrate. The results revealed a single sequence contig, which was 960 bp in length and which exhibited highly significant homology to squid p53 (score=192, $P=5.1\times10^{-12}$). Further analysis of this sequence with the BLASTX program against GenBank protein sequences demonstrated that this contig exhibited significant homology to the entire known family of p53-like sequences in vertebrates, and that it contained coding sequences homologous to the p53 family that encompassed essentially all of the DNA-binding domain, which is the most conserved region of the p53 protein family. Inspection of this contig indicated that it was an incomplete cDNA, missing coding regions C-terminal to the presumptive DNA-binding domain as well as the 3' untranslated region of the mRNA.

The full-length cDNA clone was produced by Rapid Amplification of cDNA ends (RACE; Frohman et al., PNAS (1988) 85:8998–9002). A RACE-ready library was generated from Clontech (Palo Alto, Calif.) Drosophila embryo poly $A^+$ RNA (Cat#694-1) using Clontech's Marathon cDNA amplification kit (Cat# K1802), and following manufacturer's directions. The following primers were used on the library to retrieve full-length clones:

| | | |
|---|---|---|
| 3'373 | CCATGCTGAAGCAATAACCACCGATG | SEQ ID NO: 11 |
| 3'510 | GGAACACACGCAAATTAAGTGGTTGGATGG | SEQ ID NO: 12 |
| 3'566 | TGATTTTGACAGCGGACCACGGG | SEQ ID NO: 13 |
| 3'799 | GGAAGTTTCTTTTCGCCCGATACACGAG | SEQ ID NO: 14 |
| 5'164 | GGCACAAAGAAAGCACTGATTCCGAGG | SEQ ID NO: 15 |
| 5'300 | GGAATCTGATGCAGTUCAGCCAGCAATC | SEQ ID NO: 16 |
| 5'932 | GGATCGCATCCAAGACGAACGCC | SEQ ID NO: 17 |

RACE reactions to obtain additional 5' and 3' sequence of the Drosophila p53 cDNA were performed as follows. Each RACE reaction contained: 40 μl of $H_2O$, 5 μl of 10×Advantage PCR buffer (Clontech), 1 μl of specific p53 RACE primer at 10 μM, 1 μl of AP1 primer (from Clontech Marathon kit) at 10 μM, 1 μl of cDNA, 1 μl of dNTPs at 5 mM, 1 μl of Advantage DNA polymerase (Clontech). For 5' RACE, the reactions contained either the 3'373, 3'510, 3'566, or 3'799 primers. For 3' RACE, the reactions contained either the 5'164 or 5'300 primers. The reaction mixtures were subjected to the following thermocycling program steps for touchdown PCR: (1) 94° C. 1 min, (2) 94° C. 0.5 min, (3) 72° C. 4 min, (4) repeat steps 2–3 four times, (5) 94° C. 0.5 min, (7) repeat steps 5–6 four times, (8) 94° C. 0.33 min, (9) 68° C. 4 min, (10) repeat steps 8–9 24 times, (11) 68° C. 4 min, (12) remain at 4° C.

Products of the RACE reactions were analyzed by gel electrophoresis. Discrete DNA species of the following sizes were observed in the RACE products produced with each of the following primers: 3'373, approx. 400 bp; 3'510, approx. 550 bp, 3'566, approx. 600 bp; 3'799, approx. 850 bp; 5'164, approx. 1400 bp, 5'300 approx. 1300 bp. The RACE DNA products were cloned directly into the vector pCR2.1 using the TOPO TA cloning kit (Invitrogen Corp., Carlsbad, Calif.) following the manufacturers directions. Colonies of transformed *E. coli* were picked for each construct, and plasmid DNA prepared using a QIAGEN tip 20 kit (QIAGEN, Valencia, Calif.). Sequences of the RACE cDNA inserts in within each clone were determined using standard protocols for the BigDye sequencing reagents (Applied Biosystems, Inc. Foster City, Calif.) and either M13. reverse or BigT7 primers for priming from flanking vector sequences, or 5'932 or 3'373 primers (described above) for priming internally from Drosophila p53 cDNA sequences. The products were analyzed using ABI 377 DNA sequencer. Sequences were assembled into a contig using the Sequencher program (Gene Codes Corporation), and contained a single open reading frame encoding a predicted protein of 385 amino acids, which compared favorably with the known lengths of vertebrate p53 proteins, 363 to 396 amino acids (Soussi et al., Oncogene (1990) 5:945–952). Analysis of the predicted Drosophila p53 protein using the BLASTP homology searching program and the GenBank database confirmed that this protein was a member of the p53 family, since it exhibited highly significant homology to all known p53 related proteins, but no significant homology to other protein families.

Example 4

Cloning of p53 Nucleic Acid Sequences from Other Insects

The PCR conditions used for cloning the p53 nucleic acid sequences comprised a denaturation step of 94° C., 5 min; followed by 35 cycles of: 94° C. 1 min, 55° C. 1 min 72° C. 1 min; then, a final extension at 72° C. 10 min. All DNA sequencing reactions were performed using standard protocols for the BigDye sequencing reagents (Applied Biosystems, Inc.) and products were analyzed using ABI 377 DNA sequencers. Trace data obtained from the ABI 377 DNA sequencers was analyzed and assembled into contigs using the Phred-Phrap programs.

The DMp53 DNA and protein sequences were used to query sequences from Tribolium, Leptinotarsa, and Heliothis cDNA libraries using the BLAST computer program, and the results revealed several candidate cDNA clones that might encode p53 related sequences. For each candidate p53 cDNA clone, well-separated, single colonies were streaked on a plate and end-sequenced to verify the clones. Single colonies were picked and the plasmid DNA was purified using Qiagen REAL Preps (Qiagen, Inc., Valencia, Calif.). Samples were then digested with appropriate enzymes to excise insert from vector and determine size. For example, the vector pOT2, can be excised with Xho1/EcoRI; or pBluescript (Stratagene) can be excised with BssH II. Clones were then sequenced using a combination of primer walking and in vitro transposon tagging strategies.

For primer walking, primers were designed to the known DNA sequences in the clones, using the Primer-3 software (Steve Rozen, Helen J. Skaletsky (1998) Primer3. These primers were then used in sequencing reactions to extend the sequence until the full sequence of the insert was determined.

The GPS-1 Genome Priming System in vitro transposon kit (New-England Biolabs, Inc., Beverly, Mass.) was used for transposon-based sequencing, following manufacturer's protocols. Briefly, multiple DNA templates with randomly interspersed primer-binding sites were generated. These clones were prepared by picking 24 colonies/clone into a Qiagen REAL Prep to purify DNA and sequenced by using supplied primers to perform bidirectional sequencing from both ends of transposon insertion.

Sequences were then assembled using Phred/Phrap and analyzed using Consed. Ambiguities in the sequence were resolved by resequencing several clones. This effort resulted in several contiguous nucleotide sequences. For Leptinotarsa, a contig was assembled of 2601 bases in length, encompassing an open reading frame (ORF) of 1059 nucleotides encoding a predicted protein of 353 amino acids. The ORF extends from base 121–1180 of SEQ ID NO:3. For Tribolium, a contig was assembled of 1292 bases in length, encompassing an ORF of 1050 nucleotides, extending from base 95–1145 of SEQ ID NO:5, and encoding a predicted protein of 350 amino acids. The analysis of another candidate Tribolium p53 clone also generated a second contig of 509 bases in length, encompassing a partial ORF of 509 nucleotides (SEQ ID NO: 7), and encoding a partial protein of 170 amino acids. For Heliothis, a contig was assembled of 434 bases in length, encompassing a partial ORF of 434 nucledtides (SEQ ID NO:9), and encoding a partial protein of 145 amino acids.

Example 5

Northern Blot Analysis of DMp53

Northern blot analysis using standard methods was performed using three different poly(A)+ mRNA preparations, 0–12 h embryo, 12–24 h embryo, and adult, which were fractionated on an agarose gel along with size standards and blotted to a nylon membrane. A DNA fragment containing the entire Drosophila p53 coding region was excised by HincII digestion, separated by electrophoresis in an agarose gel, extracted from the gel, and $^{32}$P-labeled by random-priming using the Rediprime labeling system (Amersham, Piscataway, N.J.). Hybridization of the labeled probe to the mRNA blot was performed overnight. The blot was washed at high stringency (0.2×SSC/0.1% SDS at 65° C.) and mRNA species that specifically hybridized to the probe were detected by autoradiography using X-ray film. The results showed a single cross-hybridizing mRNA species of approximately 1.6 kilobases in all three mRNA sources. This data was consistent with the observed sizes of the 5' and 3' RACE products described above.

Example 6

Cytogenetic Mapping of the DMp53 Gene

It was of interest to identify the map location of the DMp53 gene in order to determine whether any existing Drosophila mutants correspond to mutations in the DMp53 gene, as well as for engineering new mutations within this gene. The cytogenetic location of the DMp53 gene was determined by in situ hybridization to polytene chromosomes (Pardue, Meth Cell Biol (1994) 44:333–351) following the protocol outlined below (steps A–C).

(A) Preparation of polytene chromosome squashes: Dissected salivary glands were placed into a drop of 45% acetic acid. Glands were transferred to drop of 1:2:3 mixture of lactic acid:water:acetic acid. Glands were then squashed between a cover slip and a slide and incubated at 4° C. overnight Squashes were frozen in liquid $N_2$ and the coverslip removed. Slides were then immediately immersed in 70% ethanol for 10 min. and then air dried. Slides were then heat treated for 30 min. at 68° C. in 2×SSC buffer. Squashes were then dehydrated by treatment with 70% ethanol for 10 min. followed by 95% ethanol for 5 mm.

(B) Preparation of a biotinylated hybridization probe: a solution was prepared by mixing: 50 $\mu$l of 1 M Tris-HCl pH 7.5, 6.35 $\mu$l of 1 M $MgCl_2$, 0.85 $\mu$l of beta-mercaptoethanol, 0.625 $\mu$l of 100 mM dATP, 0.625 $\mu$l of 100 mM dCTP, 0.625 $\mu$l of 100 mM dGTP, 125 $\mu$l of2 M HEPES pH 6.6, and 75

μl of 10 mg/ml pd(N)$_6$ (Pharmacia, Kalamazoo, Mich.). 10 μl of this solution was then mixed with 2 μl 10 mg/ml bovine serum albumin, 33 μl containing (0.5 μg) DMp53 cDNA fragment denatured by quick boiling, 5 μl of 1 mM biotin-16-dUTP (Boehringer Mannheim, Indianapolis, Ind.), and 1 μl of Klenow DNA polymerase (2 U) (Boehringer Mannheim). The mixture was incubated at room temperature overnight and the following components were then added:1 μl of 1 mg/ml sonicated denatured salmon sperm DNA, 5.5 μl 3 M sodium acetate pH 5.2, and 150 μl ethanol (100%). After mixing the solution was stored at −70° C. for 1–2 hr. DNA precipitate was collected by centrifugation in a microcentrifuge and the pellet was washed once in 70% ethanol, dried in a vacuum, dissolved in 50 μl TE buffer, and stored at −20° C.

(C) Hybridization and staining was performed as follows: 20 μl of the probe added to a hybridization solution (112.5 μl formamide; 25 μl 20×SSC, pH 7.0; 50 μl 50% dextran sulfate; 62.5 μl distilled $H_2O$) was placed on the squash. A coverslip (22 mm$^2$) was placed on the squash and sealed with rubber cement and placed on the airtight moist chamber overnight at 42° C. Rubber cement was removed by pealing off cement, then coverslip removed in 2×SSC buffer at 37° C. Slides were washed twice 15 min each in 2×SSC buffer at 37° C. Slides were then washed twice 15 min each in PBS buffer at room temperature. A mixture of the following "Elite" solution was prepared by mixing: 1 ml of PBT buffer (PBS buffer with 0.1% Tween, 20), 10 μl of Vectastain A (Vector Laboratories, Burlingame, Calif.), and 10 μl of Vectastain B (Vector Laboratories). The mixture was then allowed to incubate for 30 min. 50 μl of the Elite solution was added to the slide then drained off. 75 μl of the Elite solution was added to slide and a coverslip was placed onto the slide. The slide was incubated in moist chamber 1.5–2 hr at 37° C. The coverslip was then removed in PBS buffer, and the slide was washed twice 10 min each in PBS buffer.

A fresh solution of DAB (diaminobenzidine) in PBT buffer was made by mixing 1 μl of 0.3% hydrogen peroxide with 40 μl 0.5 mg/ml DAB solution. 40 μl of the DAB/peroxide solution was then placed onto each slide. A coverslip was placed onto the slide and incubated 2 min. Slides were then examined under a phase microscope and reaction was stopped in PBS buffer when signal was determined to be satisfactory. Slides were then rinsed in running $H_2O$ for 10 min. and air dried. Finally, slides were inspected under a compound microscope to assign a chromosomal location to the hybridization signal. A single clear region of hybridization was observed on the polytene chromosome squashes which was assigned to cytogenetic bands 94D2–6.

Example 7

Isolation and Sequence Analysis of a Genomic Clone for the DMp53 Gene

PCR was used to generate DNA probes for identification of genomic clones containing the DMp53 gene. Each reaction (50 μl total volume) contained 100 ng Drosophila genomic DNA, 2.5 μM each dNTP, 1.5 mM $MgCl_2$, 2 μM of each primer, and 1 μl of TAKARA exTaq DNA polymerase (PanVera Corp., Madison, Wis.). Reactions were set up with primer pair 5'164 & 3'510 (described above), and thermocycling conditions used were as follows (where 0:00 indicates time in minutes:seconds): initial denaturation of 94° C., 2:00; followed by 10 cycles of 94° C., 0:30, 58° C. 0:30, 68° C., 4:00; followed by 20 cycles of 94° C., 0:30, 55° C., 0:30, 68° C., 4:00+0:20 per cycle. PCR products were then fractionated by agarose gel electrophoresis, $^{32}$P-labeled by nick translation, and hybridized to nylon membranes containing high-density arrayed P1 clones from the Berkeley Drosophila Genome Project (University of California Berkeley, and purchased from Genome Systems, Inc., St. Louis, Mo.). Four positive P1 clones were identified: DS01201, DS02942, DS05102, and DS06254, and each clone was verified using a PCR assay with the primer pair described above. To prepare DNA for sequencing, *E. coli* containing each P1 clone was streaked to single colonies on LB agar plates containing 25 μg/ml kanamycin, and grown overnight at 37° C. Well-separated colonies for each P1 clone were picked and used to inoculate 250 ml LB medium containing 25 μg/ml kanamycin and cultures were grown for 16 hours at 37° C. with shaking. Bacterial cells were collected by centrifugation, and DNA purified with a Qiagen Maxi-Prep System kit (QIAGEN; Inc., Valencia, Calif.). Genomic DNA sequence from the P1 clones was obtained using a strategy that combined shotgun and directed sequencing of a small insert plasmid DNA library derived from the P1 clone DNAs (Ruddy et al. Genome Research (1997) 7:441–456). All DNA sequencing and analysis were performed as descibed before, and P1 sequence contigs were analyzed using the BLAST sequence homology searching programs to identify those that contained the DMp53 gene or other coding regions. This analysis demonstrated that the DMp53 gene was divided into 8 exons and 7 introns. In addition, the BLAST analysis indicated the presence of two additional genes that flank the DMp53 gene; one exhibited homology to a human gene implicated in nephropathic cystinosis (labeled CTNS-like gene) and the second gene exhibited homology to a large family of oxidoreductases. Thus, we could operationally define the limits of the DMp53 gene as an 8,805 bp corresponding the DNA region lying between the putative CTNS-like and oxidoreductase-like genes.

Example 8

Analysis of p53 Nucleic Acid Sequences

Upon completion of cloning, the sequences were analyzed using the Pfam and Prosite programs, and by visual analysis and comparison with other p53 sequences. Regions of cDNA encoding the various domains of SEQ ID Nos 1–6 are depicted in Table I above. Additionally, Pfam predicted p53 similarity regions for the partial TRIB-Bp53 at amino acid residues 118–165 (SEQ ID NO:8) encoded by nucleotides 354–495 (SEQ ID NO:7), and for the partial HELIOp53 at amino acid residues 105–138 (SEQ ID NO:10) encoded by nucleotides 315–414 (SEQ ID NO:9).

Nucleotide and amino acid sequences for each of the p53 nucleic acid sequences and their encoded proteins were searched against all available nucleotide and amino acid sequences in the public databases, using BLAST (Altschul et al., supra). Tables 2–6 below summarize the results. The 5 most similar sequences are listed for each p53 gene.

TABLE 2

DMp53

| GI# | DESCRIPTION |
|---|---|
| DNA BLAST of SEQ ID NO: 1 | |
| 6664917 = C019980 | *Drosophila melanogaster*, *** SEQUENCING IN PROGRESS***, in ordered pieces |
| 5670489 = AC008200 | *Drosophila melanogaster* chromosome 3 clone BACR17P04 (D757) RPCI-98 17.P.4 map 94D–94E strain y; cn bw sp, ***SEQUENCING IN PROGRESS***, 70 unordered pieces. |

TABLE 2-continued

DMp53

| GI# | DESCRIPTION |
|---|---|
| 4419483 = AI516383 | *Drosophila melanogaster* cDNA clone LD42237 5prime, mRNA sequence |
| 4420516 = AI517416 | *Drosophila melanogaster* cDNA clone GH28349 5prime, mRNA sequence |
| 4419333 = AI516233 | *Drosophila melanogaster* cDNA clone LD42031 5prime, mRNA sequence |
| PROTEIN BLAST of SEQ ID NO: 2 | |
| 1244764 = AA98564 | p53 tumor suppressor homolog [*Loligo forbesi*] |
| 1244762 = AA98563 | p53 tumor suppressor homolog [*Loligo forbesi*] |
| 2828704 = AC31133 | tumor protein p53 [*Xiphophorus helleri*] |
| 2828706 = AC31134 | tumor protein p53 [*Xiphophorus maculatus*] |
| 3695098 = AC62643 | DN p63 beta [*Mus musculus*] |

TABLE 3

CPBp53

| GI# | DESCRIPTION |
|---|---|
| DNA BLAST of SEQ ID NO: 3 | |
| 6468070 = AC008132 | *Homo sapiens*, complete sequence Chromosome 22q11 PAC Clone pac995o6 In CES-DGCR Region |
| 4493931 = AL034556 | *Plasmodium falciparum* MAL3P5, complete sequence |
| 3738114 = AC004617 | *Homo sapiens* chromosome Y, clone 264,M,20, complete sequence |
| 4150930 = AC005083 | *Homo sapiens* BAC clone CTA-281G5 from 7p15–p21, complete sequence |
| 4006838 = AC006079 | *Homo sapiens* chromosome 17, clone hRPK.855_D_21 complete sequence |
| PROTEIN BLAST of SEQ ID NO: 4 | |
| 1244764 = AA98564 | p53 tumor suppressor homolog [*Loligo forbesi*] |
| 1244762 = AA98563 | p53 tumor suppressor homolog [*Loligo forbesi*] |
| 4530686 = AA03817 | unnamed protein product [unidentified] |
| 4803651 = CAA72225 | P73 splice variant [*Cercopithecus aethiops*] |
| 2370177 = CAA72219 | first splice variant [*Homo sapiens*] |

TABLE 4

TRIB-Ap53

| GI# | DESCRIPTION |
|---|---|
| DNA BLAST of SEQ ID NO: 5 | |
| 5877734 = AW024204 | wv01h01.x1 NCI_CGAP_Kid3 *Homo sapiens* cDNA clone IMAGE:2528305 3', mRNA sequence |
| 16555 = X65053 | *A. thaliana* mRNA for eukaryotic translation initiation factor 4A-2 |
| 6072979 = AW101398 | sd79d06.y1 Gm-c1009 Glycine max cDNA clone GENOME SYSTEMS CLONE ID: Gm-c1009-612 5', mRNA sequence |
| 6070492 = AW099879 | sd17g11.y2 Gm-c1012 Glycine max cDNA clone GENOME SYSTEMS CLONE ID: Gm-c1012-2013 5'; mRNA sequence |
| 4105775 = AF049919 | Petunia x hybrida PGP35 (PGP35) mRNA, complete cds. |

TABLE 4-continued

TRIB-Ap53

| GI# | DESCRIPTION |
|---|---|
| PROTEIN BLAST of SEQ ID NO:6 | |
| 1244764 = AAA98564 | p53 tumor suppressor homolog [*Loligo forbesi*] |
| 3273745 = AAC24830 | p53 homolog [*Homo sapiens*] |
| 1244762 = AAA98563 | p53 tumor suppressor homolog [*Loligo forbesi*] |
| 3695096 = AAC62642 | N p63 gamma [*Mus musculus*] |
| 3695080 = AAC62634 | DN p63 gamma [*Homo sapiens*] |

TABLE 5

TRIB-Bp53

| GI# | DESCRIPTION |
|---|---|
| DNA BLAST of SEQ ID NO: 7 | |
| 4689085 = AF043641 | *Barbus barbus* p73 mRNA, complete cds |
| 4530689 = A64588 | Sequence 7 from Patent WO9728186 |
| N/A | No further homologies |
| PROTEIN BLAST of SEQ ID NO: 8 | |
| 4689086 = AAD27752 | p73 [*Barbus barbus*] |
| 4530686 = CAA03817 | unnamed protein product [unidentified] |
| 4803651 = CAA72225 | P73 splice variant [*Cercopithecus aethiops*] |
| 4530690 = CAA03819 | unnamed protein product [unidentified] |
| 4530684 = CAA03816 | unnamed protein product [unidentified] |

TABLE 6

HELIO p53

| GI# | DESCRIPIION |
|---|---|
| DNA BLAST of SEQ ID NO: 9 | |
| N/A | No homologies found |
| PROTEIN BLAST of SEQ ID NO: 10 | |
| 2781308 = 1YCSA | Chain A, p53-53bp2 Complex |
| 1310770 = 1TSRA | Chain A, p53 Core Domain In Complex With Dna |
| 1310771 = 1TSRB | Chain B, p53 Core Domain In Complex With Dna |
| 1310772 = 1TSRC | Chain C, p53 Core Domain In Complex With Dna |
| 1310960 = 1TUPA | Chain A, Tumor Suppressor p53 Complexed With Dna |

BLAST analysis using each of the p53 amino acid sequences to find the number of amino acid residues as the shortest stretch of contiguous novel amino acids with respect to published sequences indicate the following: 7 amino acid residues for DMp53 and for TRIB-Ap53, 6 amino acid residues for CPBp53, and 5 amino acid residues for TRIB-Bp53 and HELIOp53.

BLAST results for each of the p53 amino acid sequences to find the number of amino acid residues as the shortest stretch of contiguous amino acids for which there are no sequences contained within public database sharing 100% sequence similarity indicate the following: 9 amino acid residues for DMp53, CPBp5, TRIB-Ap53, and TRIB-Bp53, and 6 amino acid residues for HELIOp53.

Example 9

Drosophila Genetics

Fly culture and crosses were performed according to standard procedures at 22–25° C. (Ashburner, supra). G1-DMp53 overexpression constructs were made by cloning a BclI HincII fragment spanning the DMp53 open reading frame into a vector (pExPress) containing glass multiple repeats upstream of a minimal heat shock promoter. The pExPress vector is an adapted version of the pGMR vector (Hay et al., Development (1994) 120:2121–2129) which contains an alpha tubulin 3' UTR for increased protein stabilization and a modified multiple cloning site. Standard P-element mediated germ line transformation was used to generate transgenic lines containing these constructs (Rubin and Spradling, supra). For X-irradiation experiments, third instar larvae in vials were exposed to 4,060 Rads of X-rays using a Faxitron X-ray cabinet system (Wheeling, Ill.).

Example 10

Whole-mount RNA in situ Hybridization, TUNEL, and Immunocytochemistry

In situ hybridization was performed using standard methods (Tautz and Pfeifle, Chrornosoma (1989) 98:81–85). DMp53 anti-sense RNA probe was generated by digesting DMp53 cDNA with EcoR1 and transcribing with T7 RNA polymerase. For immunocytochemistry, third instar larval eye and wing discs were dissected in PBS, fixed in 2% formaldehyde for 30 minutes at room temperature, permeabilized in PBS+0.5% Triton for 15 minutes at room temperature, blocked in PBS+5% goat serum, and incubated with primary antibody for two hours at room temperature or overnight at 4° C. Anti-phospho-histone staining used Anti-phospho-histone H3 Mitosis Marker (Upstate Biotechnology, Lake Placid, N.Y.) at a 1:500 dilution. Anti-DMp53 monoclonal antibody staining used hybridoma supernatant diluted 1:2. Goat anti-mouse or anti-rabbit secondary antibodies conjugated to; FTC or Texas Red (Jackson Immunoresearch, West Grove, Pa.) were used at a 1:200 dilution. Antibodies were diluted in PBS+5% goat serum. TUNEL assay was performed by using the Apoptag Direct kit (Oncor, Gaithersburg, Md.) per manufacturer's protocol with a 0.5% Triton/PBS permeabilization step. Discs were mounted in anti-fade reagent. (Molecular Probes, Eugene, Oreg.) and images were obtained on a Leica confocal microscope. BrDU staining was performed as described (de Nooij et al., Cell. (1996)87(7):1237–1247) and images were obtained on an Axioplan microscope (Zeiss, Thornwood, N.Y.).

Example 11

Generation of Anti-DMp53 Antibodies

Anti-DMp53 rabbit polyclonal (Josman Labs, Napa, Calif.) and mouse monoclonal antibodies (Antibody Solutions Inc., Palo Alto, Calif.) were generated by standard methods using a full-length DMp53 protein fused to glutathione-S-transferase (GST-DMp53) as antigen. Inclusion bodies of GST-DMp53 were purified by centrifugation using B-PER buffer (Pierce, Rockford; Ill.) and injected subcutaneously into rabbits and mice for immunization. The final boost for mouse monoclonal antibody production used intravenous injection of soluble GST-DMp53 produced by solubilization of GST-DMp53 in 6M GuHCl and dialysis into phosphate buffer containing 1M NaCl. Hybridoma supernatants were screened by ELISA using a soluble 6×HIS-tagged DMp53 protein bound to Ni-NTA coated plates (Qiagen, Valencia, Calif.) and an anti-mouse IgG Fc-fragment specific secondary antibody.

Example 12

Functional Analysis

The goal of this series of experiments was to compare and contrast the functions of the insect p53s to those of the human p53. The DMp53 was chosen to carry out this set of experiments, although any of the other insect p53s could be used as well.

p53 Involvement in the Cell Death Pathway

To determine whether DMp53 can serve the same functions in vivo as human p53, DMp53 was ectopically expressed in Drosophila larval eye discs using glass-responsive enhancer elements. The glass-DMp53 (gl-DMp53) transgene expresses DMp53 in all cells posterior to the morphogenetic furrow. During eye development, the morphogenetic furrow sweeps from the posterior to the anterior of the eye disc. Thus, gl-DMp53 larvae express DMp53 in a field of cells which expands from the posterior to the anterior of the eye disc during larval development.

Adult flies carrying the gl-DMp53 transgene were viable but had small, rough eyes with fused ommatidia (any of the numerous elements of the compound eye). TUNEL staining of gl-DMp53 eye discs showed that this phenotype was due, at least in part, to widespread apoptosis in cells expressing DMp53. Results were confirmed by the detection of apoptotic cells with acridine orange and Nile Blue. TUNEL-positive cells appeared within 15–25 cell diameters of the furrow. Given that the furrow moves approximately 10 cell diameters per hour, this indicated that the cells became apoptotic 2–3 hours after DMp53 was expressed. Surprisingly, co-expression of the baculovirus cell death inhibitor p35 did not block the cell death induced by DMp53 (Miller, J Cell Physiol (1997) 173(2):178–182; Ohtsubo et al., Nippon Rinsho (1996) 54(7):1907–1911). However, DMp53-induced apoptosis and the rough-eye phenotype in gl-DMp53 flies could be suppressed by co-expression of the human cyclin-dependent-kinase inhibitor p21. Because p21 overexpression blocks cells in the G1 phase of the cell cycle, this finding suggests that transit through the cell cycle sensitizes cells to DMp53-induced apoptosis. A similar effect of p21 overexpression on human p53-induced apoptosis has been described.

p53 Involvement in the Cell Cycle

In addition to its ability to affect cell death pathways, mammalian p53 can induce cell cycle arrest at the G1 and G2/M checkpoints. In the Drosophila eye disc, the second mitotic wave is a synchronous, final wave of cell division posterior to the morphogenetic furrow. This unique aspect of development provides a means to assay for similar effects of DMp53 on the cell. The transition of cells from G1 to S phase can be detected by BrdU incorporation. Eye discs-dissected from wild-type third instar larvae displayed a tight band of BrdU-staining cells corresponding to DNA replication in the cells of the second mitotic wave. This transition from G1 to S phase was unaffected by DMp53 overexpression from the gl-DMp53 transgene. In contrast, expression of human p21 or a Drosophila homologue, dacapo (de Nooij et al., Cell (1996) 87(7):1237–1247; Lane et al., Cell (1996) 87(7):1225–1235), under control of glass-responsive enhancer elements completely blocked DNA replication in the second mitotic wave. In mammalian cells, p53 induces a cell cycle block in G1 through transcriptional activation of the p21 gene. These results suggest that this function is not conserved in DMp53.

In wild-type eye discs, the second mitotic wave typically forms a distinct band of cells that stain with an anti-phospho-histone antibody. In gl-DMp53 larval eye discs, this band of cells was significantly broader and more diffuse, suggesting that DMp53 alters the entry into and/or duration of M phase.

p53 Response to DNA Damage

The following experiments were performed to determine whether loss of DMp53 function affected apoptosis or cell cycle arrest in response to DNA damage.

In order to examine the phenotype of tissues deficient in DMp53 function, dominant-negative alleles of DMp53 were generated. These mutations are analogous to the R175H (R155H in DMp53) and H179N (H159N in DMp53) mutations in human p53. These mutations in human p53 act as dominant-negative alleles, presumably because they cannot bind DNA but retain a functional tetramenization domain. Co-expression of DMp53 R155H with wild-type DMp53 suppressed the rough eye phenotype that normally results from wild type DMp53, overexpression, confirming that this mutant acts as a dominant-negative allele in vivo. Unlike wild type DMp53, overexpression of DMp53 R155H or H159N using the glass enhancer did not produce a visible phenotype, although subtle alterations in the bristles of the eye were revealed by scanning electron microscopy.

In mamnalian systems, p53-induced apoptosis plays a crucial role in preventing the propagation of damaged DNA. DNA damage also leads to apoptosis in Drosophila. To determine if this response requires the action of DMp53, dominant-negative DMp53 was expressed in the posterior compartment of the wing disc. Following X-irradiation, wing discs were dissected. TUNEL staining revealed apoptotic cells and anti-DMp53 antibody revealed the expression pattern of dominant-negative DMp53. Four hours after X-irradiation, wild type third instar larval wing discs showed widespread apoptosis. When the dominant-negative allele of DMp53 was expressed in the posterior compartment of the wing disc, apoptosis was blocked in the cells expressing DMp53. Thus, induction of apoptosis following X-irradiation requires the function of DMp53. This pro-apoptotic role for DMp53 appears to be limited to a specific response to cellular damage, because developmentally programmed cell death in the eye and other tissues is unaffected by expression of either dominant-negative DMp53 allele. The requirement for DMp53 in the apoptotic response to X-irradiation suggests that DMp53 may be activated by DNA damage. In mammals, p53 is activated primarily by stabilization of p53 protein.

Although DMp53 function is required for X-ray induced apoptosis, it does not appear to be necessary for the cell cycle arrest induced by the same dose of irradiation. In the absence of irradiation, a random pattern of mitosis was observed in 3rd instar wing discs of Drosophila. Upon irradiation, a cell cycle block occured in wild-type discs as evidenced by a significant decrease in anti-phospho-histone staining. The cell cycle block was unaffected by expression of dominant-negative DMp53 in the posterior of the wing disc. Several time points after X-irradiation were examined and all gave similar results, suggesting that both the onset and maintenance of the X-ray induced cell cycle arrest is independent of DMp53.

p53 in Normal Development

Similar to p53 in mice, DMp53 does not appear to be required for development because widespread expression of dominant-negative DMp53 in Drosophila had no significant effects on appearance, viability, or fertility. Interestingly, in situ hybridization of developing embryos revealed widespread early embryonic expression that became restricted to primordial germ cells in later embryonic stages. This expression pattern may indicate a crucial role for DMp53 in protecting the germ line, similar to the proposed role of mammalian p53 in protection against teratogens.

Example 13 p53 RNAi Experiments in Cell Culture

Stable Drosophila S2 cell lines expressing hemaglutinin epitope (HA) tagged p53, or vector control under the inducible metallothionen promoter were produced by transfection using pMTNV5-His (Invitrogen, Carlsbad, Calif.). Induction of DMp53 expression by addition of copper to the medium resulted in cell death via apoptosis. Apoptosis was measured by three different methods: a cell proliferation assay; FACS analysis of the cell population in which dead cells were detected by their contracted nuclei; and a DNA ladder assay. The ability to use RNAi in S2 cell lines allowed p53 regulation and function to be explored using this inducible cell-based p53 expression system.

Preparation of the dsRNA template: PCR primers containing an upstream T7 RNA polymerase binding site and downstream DMp53 gene sequences were designed such that sequences extending from nucleotides 128 to 1138 of the DMp53 cDNA sequence (SEQ ID NO:1) could be amplified in a manner that would allow the generation of a DMp53-derived dsRNA. PCR reactions were performed using EXPAND High Fidelity (Boehringer Mannheim, Indianapolis, Ind.) and the products were then purified.

DMp53 RNA was generated from the PCR template using the Promega Large Scale RNA Production System (Madison, Wis.) following manufacturer's protocols. Ethanol precipitation of RNA was performed and the RNA was annealed by a first incubation at 68° C. for 10 min, followed by a second incubation at 37° C. for 30 min. The resulting dsRNA was stored at −80° C.

RNAi experiment in tissue culture: RNAi was performed essentially as described previously. On day 1, cultures of Drosophila S2 cells were obtained that expressed pMT-HA-DMp53 expression plasmid and either 15 μg of DMp53 dsRNA or no RNA was added to the medium. On the second day, $CuSO_4$was added to final concentrations of either 0, 7, 70 or 700 μM to all cultures. On the fourth day, an alamarBlue (Alamar Biosciences Inc., Sacramento, Calif.) staining assay was performed to measure the number of live cells in each culture, by measuring fluorescence at 590 nm.

At 7 μM $CuSO_4$, there was no change in cell number from 0 μM $CuSO_4$ for RNAi treated or untreated cells. At 70 μM $CuSO_4$, there was no change in cell number from 0 μM $CuSO_4$ for the RNAi-treated category. However, the number of cells that were not treated with RNAi dropped by 30%. At 700 μM $CuSO_4$, the number of cells that were treated with RNAi dropped by 30% (as compared with 0 μM $CuSO_4$), while the number of cells that were not treated with RNAi dropped by 70%.

These experiments showed that p53 dsRNA rescued at least 70% of the cells in the p53 inducible category, since some cell loss might be attributable to copper toxicity. Results of these experiments demonstrate that DMp53 dsRNA rescues cells from apoptosis caused by inducing DMp53 overexpression. Thus, this experimental cell-based system represents a defined and unique way to study the mechanisms of p53 function and regulation.

What is claimed is:

1. An isolated nucleic acid sequence comprising SEQ ID NO:1.

2. An isolated nucleic acid sequence encoding a polypeptide with an amino acid sequence comprising SEQ ID NO:2.

* * * * *